United States Patent
Hamade et al.

(10) Patent No.: US 10,431,761 B2
(45) Date of Patent: Oct. 1, 2019

(54) LIGHT-EMITTING ELEMENT, LIGHT-EMITTING DEVICE, AUTHENTICATION DEVICE, AND ELECTRONIC APPARATUS

(71) Applicant: Seiko Epson Corporation, Tokyo (JP)

(72) Inventors: Yuiga Hamade, Fujimi-machi (JP); Tetsuji Fujita, Chino (JP)

(73) Assignee: Seiko Epson Corporation (JP)

( * ) Notice: Subject to any disclaimer, the term of this patent is extended or adjusted under 35 U.S.C. 154(b) by 359 days.

(21) Appl. No.: 15/322,999

(22) PCT Filed: Jun. 22, 2015

(86) PCT No.: PCT/JP2015/003105
§ 371 (c)(1),
(2) Date: Dec. 29, 2016

(87) PCT Pub. No.: WO2016/002159
PCT Pub. Date: Jan. 7, 2016

(65) Prior Publication Data
US 2017/0141337 A1 May 18, 2017

(30) Foreign Application Priority Data
Jul. 2, 2014 (JP) .................................. 2014-137110

(51) Int. Cl.
*H01L 51/50* (2006.01)
*C07D 513/04* (2006.01)
(Continued)

(52) U.S. Cl.
CPC ........ *H01L 51/5004* (2013.01); *C07D 513/04* (2013.01); *C09K 11/06* (2013.01);
(Continued)

(58) Field of Classification Search
CPC .................................................. H01L 51/5004
See application file for complete search history.

(56) References Cited

U.S. PATENT DOCUMENTS

| 6,680,131 B1 | 1/2004 | Ishibashi et al. |
| 7,361,796 B2 | 4/2008 | Ikeda et al. |

(Continued)

FOREIGN PATENT DOCUMENTS

| JP | 2000091073 A | 3/2000 |
| JP | 2001110570 A | 4/2001 |

(Continued)

OTHER PUBLICATIONS

EPO/Google English machine translation of Fujita et al. JP2012-2222448 (Year: 2012).*

(Continued)

*Primary Examiner* — Peter F Godenschwager
(74) *Attorney, Agent, or Firm* — Harness, Dickey & Pierce, P.L.C.

(57) ABSTRACT

To provide a light-emitting element which emits light in a near-infrared range and has high efficiency and long life, and a light-emitting device, an authentication device, and an electronic apparatus, each of which includes this light-emitting element.
A light-emitting element 1 of the invention includes an anode 3, a cathode 8, a light-emitting layer 5 which is provided between the anode 3 and the cathode 8 and emits light in a wavelength range of 700 nm or more by applying a current between the anode 3 and the cathode 8, and an electron transport layer 6 which is provided between the light-emitting layer 5 and the cathode 8, and includes a first electron transport layer 6b located on the cathode 8 side and a second electron transport layer 6a located on the light-emitting layer 5 side, wherein the first electron transport layer 6b contains a first anthracene-based compound, which (Continued)

has an anthracene skeleton and a nitrogen-containing heterocyclic skeleton, and has an average thickness of less than 8 nm, and the second electron transport layer 6a contains a second anthracene-based compound, which has an anthracene skeleton but does not have a heterocyclic skeleton.

8 Claims, 4 Drawing Sheets

(51) Int. Cl.
C09K 11/06 (2006.01)
H01L 51/00 (2006.01)
(52) U.S. Cl.
CPC ...... H01L 51/0052 (2013.01); H01L 51/0058 (2013.01); H01L 51/0059 (2013.01); H01L 51/0061 (2013.01); H01L 51/50 (2013.01); H01L 51/508 (2013.01); H01L 51/5012 (2013.01); H01L 51/5088 (2013.01); C09K 2211/1007 (2013.01); C09K 2211/1014 (2013.01); C09K 2211/1051 (2013.01); H01L 51/0071 (2013.01); H01L 2251/552 (2013.01); H01L 2251/558 (2013.01)

(56) References Cited

U.S. PATENT DOCUMENTS

| 7,867,629 | B2 | 1/2011 | Yamamoto et al. |
| 7,887,931 | B2 | 2/2011 | Cosimbescu et al. |
| 2007/0141393 | A1 | 6/2007 | Klubek et al. |
| 2010/0252823 | A1 | 10/2010 | Kambe et al. |
| 2011/0147716 | A1 | 6/2011 | Kondakova et al. |
| 2011/0284831 | A1 | 11/2011 | Kaiser et al. |
| 2012/0267615 | A1 | 10/2012 | Fujita et al. |
| 2013/0037784 | A1 | 2/2013 | Yamamoto et al. |
| 2015/0144897 | A1 | 5/2015 | Kang et al. |

FOREIGN PATENT DOCUMENTS

| JP | 2001335516 A | 12/2001 |
| JP | 2004002297 A | 1/2004 |
| JP | 2007511067 A | 4/2007 |
| JP | 2008141217 A | 6/2008 |
| JP | 2009521799 A | 6/2009 |
| JP | 2010245211 A | 10/2010 |
| JP | 2012142383 A | 7/2012 |
| JP | 2012519944 A | 8/2012 |
| JP | 2012204793 A | 10/2012 |
| JP | 2012-222248 A | 11/2012 |
| JP | 2012219078 A | 11/2012 |
| JP | 2013038247 A | 2/2013 |
| JP | 2013514665 A | 4/2013 |
| JP | 2014-082406 A | 5/2014 |
| JP | 2014216576 A | 11/2014 |
| WO | WO-2005042668 A1 | 5/2005 |
| WO | WO-2013180503 A1 | 12/2013 |
| WO | WO-201497711 A1 | 6/2014 |

OTHER PUBLICATIONS

Extended European Search Report for Application No. EP 15 81 5419 dated Apr. 5, 2018 (7 pages).

* cited by examiner

LIGHT-EMITTING ELEMENT, LIGHT-EMITTING DEVICE, AUTHENTICATION DEVICE, AND ELECTRONIC APPARATUS

CROSS-REFERENCE TO RELATED APPLICATIONS

This application is a U.S. National Phase Application under 35 U.S.C. 371 of International Application No. PCT/JP2015/003105, filed on Jun. 22, 2015 and published in Japanese as WO 2016/002159 on Jan. 7, 2016. This application claims priority to Japanese Patent Application No. 2014-137110, filed on Jul. 2, 2014. The entire disclosures of the above applications are incorporated herein by reference.

TECHNICAL FIELD

The present invention relates to a light-emitting element, a light-emitting device, an authentication device, and an electronic apparatus.

BACKGROUND ART

An organic electroluminescence element (so-called organic EL element) is a light-emitting element having a structure in which at least one layer of a luminous organic layer is interposed between an anode and a cathode. In such a light-emitting element, by applying an electric field between the cathode and the anode, an electron is injected into a light-emitting layer from the cathode side and also a hole is injected into the light-emitting layer from the anode side, and the electron and the hole are recombined in the light-emitting layer, whereby an exciton is generated, and the energy generated when this exciton is returned to a ground state is emitted as light.

As such a light-emitting element, there is known a light-emitting element which emits light in a long wavelength range exceeding 700 nm (see, for example, JP-A-2000-091073 and JP-A-2001-110570).

For example, in a light-emitting element disclosed in PTL 1 and PTL 2, by using a material in which an amine serving as an electron donor and a nitrile group serving as an electron acceptor are allowed to coexist as functional groups in the molecule as a dopant of a light-emitting layer, the emission wavelength is shifted to a longer wavelength.

However, in the related art, an element which has high efficiency and long life could not be realized although the element can be made to emit light in a long wavelength range (in a near-infrared range) exceeding 700 nm. In addition, the realization of a light-emitting element which emits light in a near-infrared range and has long life as, for example, a light source or the like for biometric authentication for authenticating an individual using biological information such as a vein or a fingerprint has been demanded.

Further, for the purpose of increasing the efficiency and the life of a light-emitting element, for example, as disclosed in JP-A-2004-2297, as an electron injection layer, a layer containing an azaindolizine-based material has been proposed. However, also in this case, it cannot be said that the efficiency and the life thereof are increased sufficiently to be used as the light source or the like for biometric authentication.

An object of the invention is to provide a light-emitting element which emits light in a near-infrared range and has high efficiency and long life, and a light-emitting device, an authentication device, and an electronic apparatus, each of which includes this light-emitting element.

SUMMARY

Such an object is achieved by the following invention.

A light-emitting element of the invention is characterized by including an anode, a cathode, a light-emitting layer which is provided between the anode and the cathode and emits light in a wavelength range of 700 nm or more by applying a current between the anode and the cathode, and an electron transport layer which is provided between the light-emitting layer and the cathode, and includes a first electron transport layer located on the cathode side and a second electron transport layer located on the light-emitting layer side, wherein the first electron transport layer contains a first anthracene-based compound, which has an anthracene skeleton and a nitrogen-containing heterocyclic skeleton, and has an average thickness of less than 8 nm, and the second electron transport layer contains a second anthracene-based compound, which has an anthracene skeleton but does not have a heterocyclic skeleton.

According to this, a light-emitting element which emits light in a near-infrared range and has high efficiency and long life can be provided.

In the light-emitting element of the invention, it is preferred that each of a difference between the HOMO of the first anthracene-based compound and the HOMO of the second anthracene-based compound and a difference between the LUMO of the first anthracene-based compound and the LUMO of the second anthracene-based compound is 0.2 eV or more.

According to this, while reducing holes coming out of the second electron transport layer to the first electron transport layer, electrons can be smoothly transported from the first electron transport layer to the second electron transport layer, and therefore, the efficiency of the light-emitting element is increased.

In the light-emitting element of the invention, it is preferred that the electron mobility of the second anthracene-based compound is larger than the electron mobility of the first anthracene-based compound.

According to this, electrons can be more smoothly transported from the first electron transport layer to the second electron transport layer.

In the light-emitting element of the invention, it is preferred that the average thickness of the second electron transport layer is 25 nm or more and 200 nm or less.

According to this, the second electron transport layer can be made to favorably exhibit a function as a block layer that prevents holes from reaching the first electron transport layer.

In the light-emitting element of the invention, it is preferred that the light-emitting layer is constituted by including a light-emitting material and a host material which holds the light-emitting material, and the light-emitting material, the host material, the first anthracene-based compound, and the second anthracene-based compound each have a glass transition temperature of 125° C. or higher.

According to this, even if the light-emitting element is used by applying a current between the anode and the cathode at a current density of about 500 A/cm$^2$ or more and 1000 A/cm$^2$ or less, fluidization of the light-emitting layer and the electron transport layer can be suppressed or prevented, and therefore, the decrease in the luminous efficiency of the light-emitting element due to this is suppressed or prevented.

In the light-emitting element of the invention, it is preferred that the light-emitting element includes a hole injection layer provided between the light-emitting layer and the anode, and the hole injection layer is constituted by including a material having a hole injection property and at least one of the first anthracene-based compound and the second anthracene-based compound.

According to this, even if an electron comes out of the light-emitting layer and the electron is injected into the hole injection layer, at least one of the first anthracene-based compound and the second anthracene-based compound can transport the electron, and therefore, the alteration or deterioration of a material having a hole injection property by the injected electron can be suppressed or prevented. As a result, the life of the light-emitting element can be extended.

It is preferred that the light-emitting element of the invention is used by applying a current between the anode and the cathode at a current density of 500 A/cm$^2$ or more and 1000 A/cm$^2$ or less.

The light-emitting element of the invention is preferably applied to such a use.

A light-emitting device of the invention is characterized by including the light-emitting element of the invention.

Such a light-emitting device can emit light in a near-infrared range. Further, the light-emitting device includes the light-emitting element which has high efficiency and long life, and therefore has excellent reliability.

An authentication device of the invention is characterized by including the light-emitting element of the invention.

Such an authentication device can perform biometric authentication using near-infrared light. Further, the authentication device includes the light-emitting element which has high efficiency and long life, and therefore has excellent reliability.

An electronic apparatus of the invention is characterized by including the light-emitting element of the invention.

Such an electronic apparatus includes the light-emitting element which has high efficiency and long life, and therefore has excellent reliability.

DETAILED DESCRIPTION

Hereinafter, a light-emitting element, a light-emitting device, an authentication device, and an electronic apparatus of the invention will be described with reference to preferred embodiments shown in the accompanying drawings.

Figure 1:
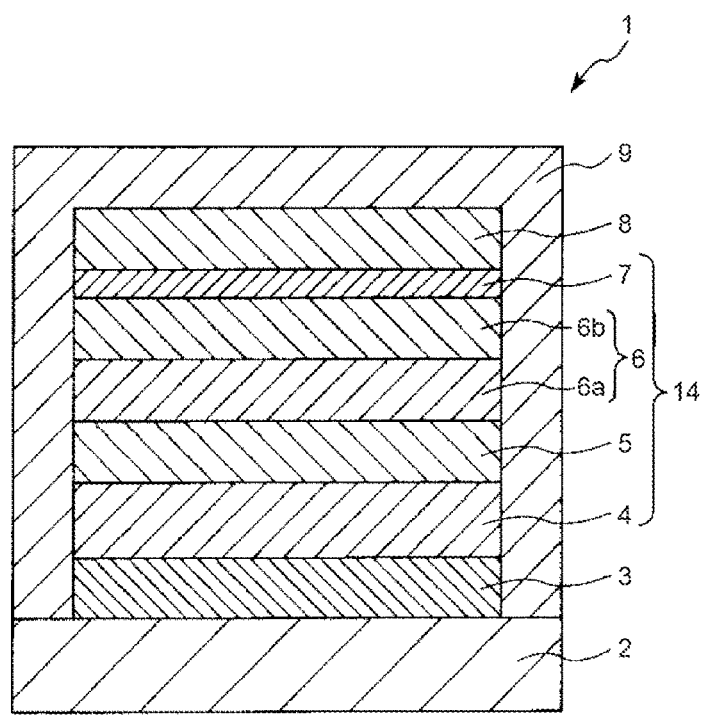
FIG. 1 is a cross-sectional view schematically showing a light-emitting element according to an embodiment of the invention.

FIG. 1 is a cross-sectional view schematically showing a light-emitting element according to an embodiment of the invention. Incidentally, hereinafter, for the sake of convenience of explanation, a description will be made by referring to the upper side and the lower side in FIG. 1 as "upper" and "lower", respectively.

A light-emitting element (electroluminescence element) 1 shown in FIG. 1 includes an anode 3, a hole injection layer 4, a light-emitting layer 5, an electron transport layer 6, an electron injection layer 7, and a cathode 8, which are stacked in this order. That is, in the light-emitting element 1, between the anode 3 and the cathode 8, a stacked body 14 in which the hole injection layer 4, the light-emitting layer 5, the electron transport layer 6, and the electron injection layer 7 are stacked in this order from the anode 3 side to the cathode 8 side is interposed.

Then, the entirety of the light-emitting element 1 is provided on a substrate 2 and sealed with a sealing member 9.

In such a light-emitting element 1, by applying a driving voltage to the anode 3 and the cathode 8, an electron is supplied (injected) to the light-emitting layer 5 from the cathode 8 side, and also a hole is supplied (injected) to the light-emitting layer 5 from the anode 3 side. Then, the hole and the electron are recombined in the light-emitting layer 5, and an exciton is generated by energy emitted at the time of this recombination, and when the exciton is returned to a ground state, energy (fluorescence or phosphorescence) is emitted (light emission). In this manner, the light-emitting element 1 emits light.

In particular, this light-emitting element 1 emits light in a near-infrared range such as a wavelength range of 700 nm or more by including a thiadiazole-based compound which is a compound represented by the following general formula (IRD1), a benzo-bis-thiadiazole-based compound which is a compound represented by the following general formula (IRD2), and a pyrromethene-based boron complex which is a compound represented by the following formula (IRD3), and the like as the light-emitting material as described below. Incidentally, the "near-infrared range" as used herein refers to a wavelength range of 700 nm or more and 1500 nm or less.

The substrate 2 supports the anode 3. The light-emitting element 1 of this embodiment is configured to extract light from the substrate 2 side (bottom emission type), and therefore, the substrate 2 and the anode 3 are each configured to be substantially transparent (colorless and transparent, colored and transparent, or semi-transparent).

Examples of the constituent material of the substrate 2 include resin materials such as polyethylene terephthalate, polyethylene naphthalate, polypropylene, a cycloolefin polymer, polyamide, polyether sulfone, polymethyl methacrylate, polycarbonate, and polyarylate, and glass materials such as quartz glass and soda glass, and among these, it is possible to use one type or two or more types in combination.

The average thickness of such a substrate 2 is not particularly limited, but is preferably from about 0.1 to 30 mm, more preferably from about 0.1 to 10 mm.

Incidentally, in the case where the light-emitting element 1 is configured to extract light from the side opposite to the substrate 2 (top emission type), both transparent substrate and non-transparent substrate can be used as the substrate 2.

Examples of the non-transparent substrate include a substrate constituted by a ceramic material such as alumina, a substrate having an oxide film (insulating film) formed on the surface of a metal substrate such as stainless steel, and a substrate constituted by a resin material.

Further, in such a light-emitting element 1, the distance between the anode 3 and the cathode 8 (that is, the average thickness of the stacked body 14) is preferably from 100 to 500 nm, more preferably from 100 to 300 nm, further more preferably from 100 to 250 nm. According to this, the driving voltage of the light-emitting element 1 can be easily and reliably made to fall within a practical range.

Hereinafter, the respective sections constituting the light-emitting element 1 will be sequentially described.

(Anode)

The anode 3 is an electrode which injects holes into the hole injection layer 4. As the constituent material of the anode 3, a material having a large work function and excellent electrical conductivity is preferably used.

Examples of the constituent material of the anode 3 include oxides such as ITO (Indium Tin Oxide), IZO (Indium Zinc Oxide), $In_3O_3$, $SnO_2$, Sb-containing $SnO_2$, and Al-containing ZnO, Au, Pt, Ag, Cu, and an alloy containing any of these metals, and among these, it is possible to use one type or two or more types in combination.

In particular, the anode 3 is preferably constituted by ITO. ITO is a material which is transparent, and also has a large work function and excellent electrical conductivity. According to this, holes can be efficiently injected from the anode 3 into the hole injection layer 4.

Further, it is preferred that the surface of the anode 3 on the hole injection layer 4 side (the upper surface in FIG. 1) is subjected to a plasma treatment. According to this, the chemical and mechanical stability of the joining surface of the anode 3 and the hole injection layer 4 can be increased. As a result, the hole injection property from the anode 3 into the hole injection layer 4 can be improved. Incidentally, such a plasma treatment will be described in detail in the description of the below-mentioned method for producing the light-emitting element 1.

The average thickness of such an anode 3 is not particularly limited, but is preferably from about 10 to 200 nm, more preferably from about 50 to 150 nm.

(Cathode)

On the other hand, the cathode 8 is an electrode which injects electrons into the electron transport layer 6 through the below-mentioned electron injection layer 7. As the constituent material of the cathode 8, a material having a small work function is preferably used.

Examples of the constituent material of the cathode 8 include Li, Mg, Ca, Sr, La, Ce, Er, Eu, Sc, Y, Yb, Ag, Cu, Al, Cs, Rb, and an alloy containing any of these metals, and among these, it is possible to use one type or two or more types in combination (for example, as a stacked body of a plurality of layers, a mixed layer of a plurality of types, or the like).

In particular, in the case where an alloy is used as the constituent material of the cathode 8, it is preferred to use an alloy containing a stable metal element such as Ag, Al, or Cu, specifically, an alloy such as MgAg, AlLi, or CuLi. By using such an alloy as the constituent material of the cathode 8, the electron injection efficiency and stability of the cathode 8 can be improved.

The average thickness of such a cathode 8 is not particularly limited, but is preferably from about 100 to 10000 nm, more preferably from about 100 to 500 nm.

Incidentally, since the light-emitting element 1 of this embodiment is a bottom emission type, a light transmission property is not particularly required for the cathode 8. Further, in the case where the light-emitting element 1 is a top emission type, since it is necessary that light be transmitted from the cathode 8 side, the average thickness of the cathode 8 is preferably from about 1 to 50 nm.

(Hole Injection Layer)

The hole injection layer 4 has a function to improve the efficiency of hole injection from the anode 3 (that is, has a hole injection property). According to this, the luminous efficiency of the light-emitting element 1 can be increased. Here, the hole injection layer 4 also has a function to transport holes injected from the anode 3 to the light-emitting layer 5 (that is, has a hole transport property). Therefore, since the hole injection layer 4 has a hole transport property as described above, it can also be said that the hole injection layer 4 is a hole transport layer. Incidentally, a hole transport layer constituted by a material different from that of the hole injection layer 4 (for example, an amine-based compound such as a benzidine derivative) may be separately provided between the hole injection layer 4 and the light-emitting layer 5.

This hole injection layer 4 contains a material having a hole injection property (a hole-injecting material).

The hole-injecting material to be contained in this hole injection layer 4 is not particularly limited, and examples thereof include copper phthalocyanine and amine-based materials such as 4,4',4''-tris(N,N-phenyl-3-methylphenylamino)triphenylamine (m-MTDATA) and N,N'-bis-(4-diphenylamino-phenyl)-N,N'-diphenyl-biphenyl-4-4'-diamine.

Above all, as the hole-injecting material to be contained in the hole injection layer 4, from the viewpoint of excellent hole injection property and hole transport property, it is preferred to use an amine-based material, and it is more preferred to use a diaminobenzene derivative, a benzidine derivative (a material having a benzidine skeleton), a triarylamine-based compound and a tetraarylamine-based compound having both of a "diaminobenzene" unit and a "benzidine" unit in the molecule (specifically, for example, compounds represented by the following formulae HIL1 to HIL27).

[Chem. 1]
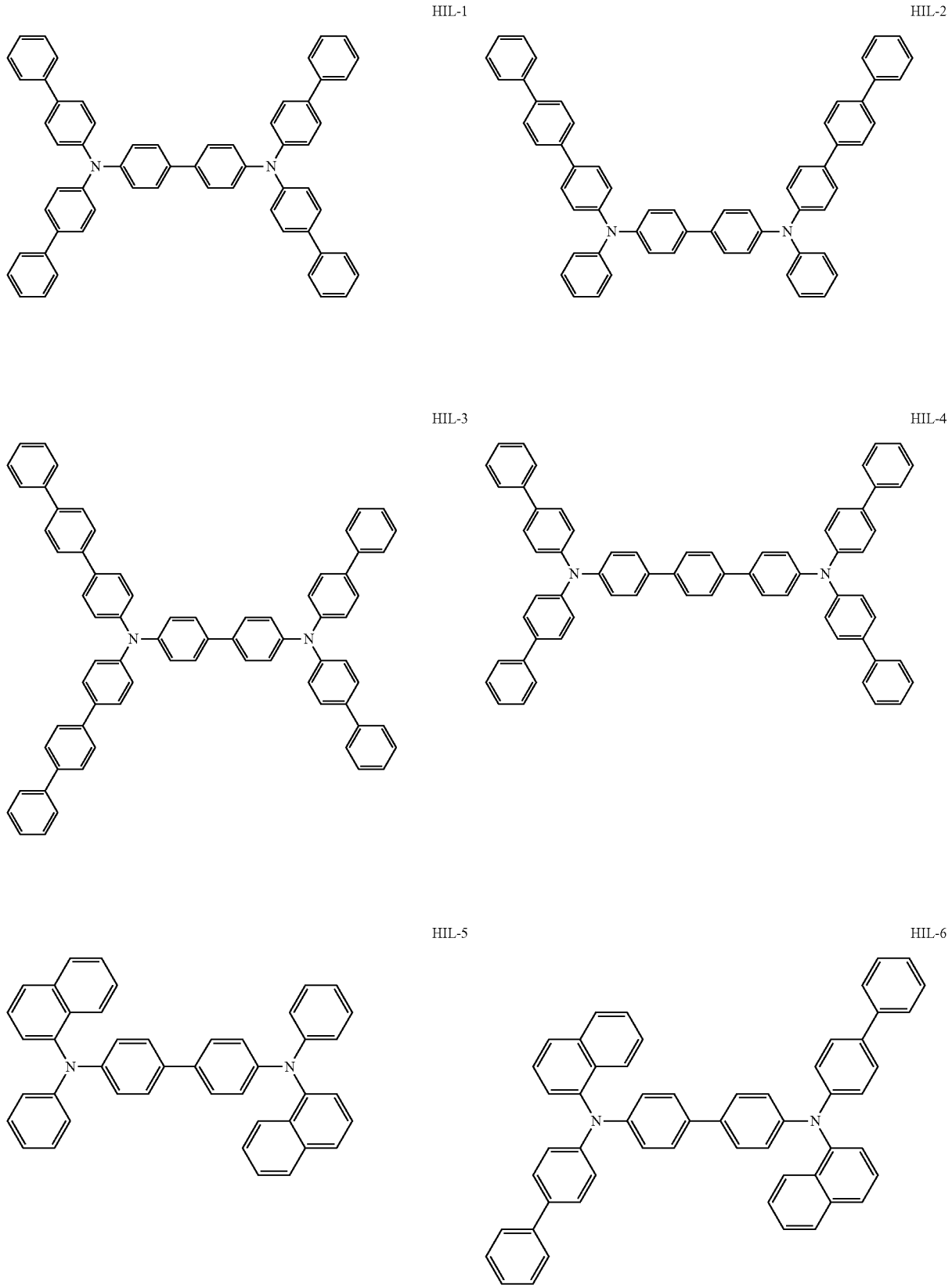

HIL-7
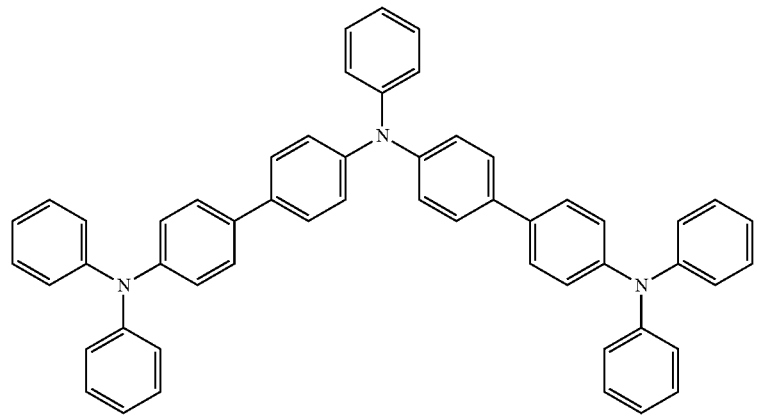
HIL-8
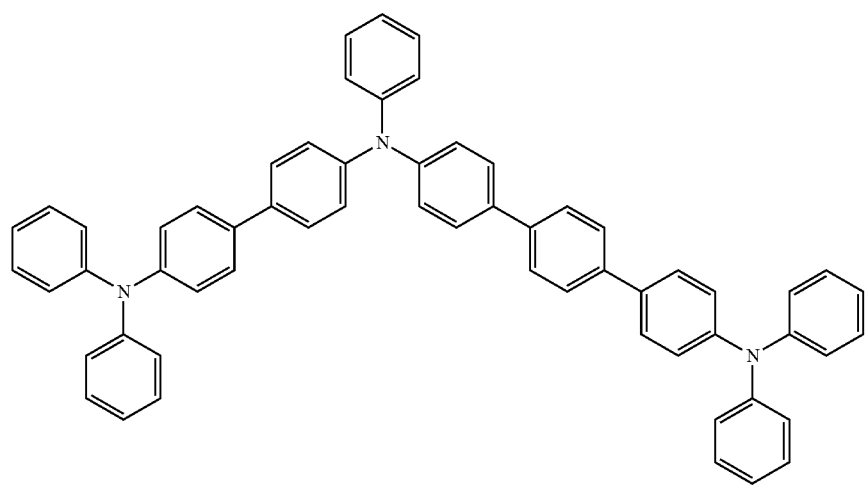
HIL-9
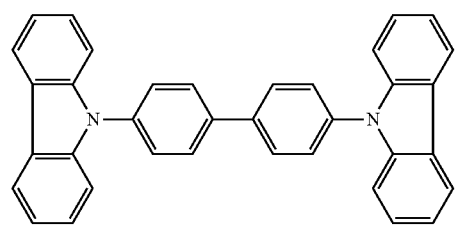
HIL-10
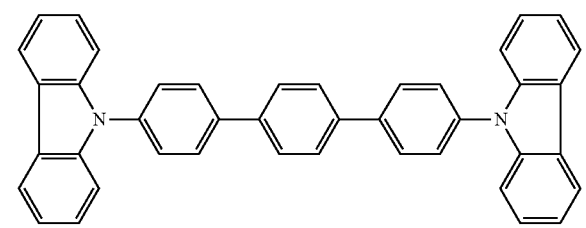
[Chem. 2]
HIL-11
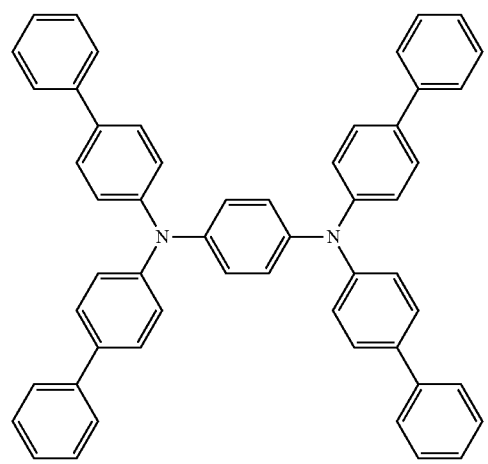
HIL-12
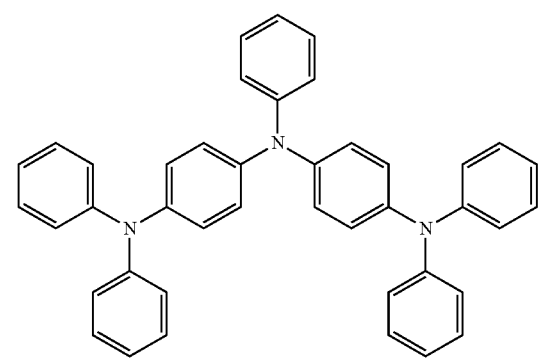

HIL-13
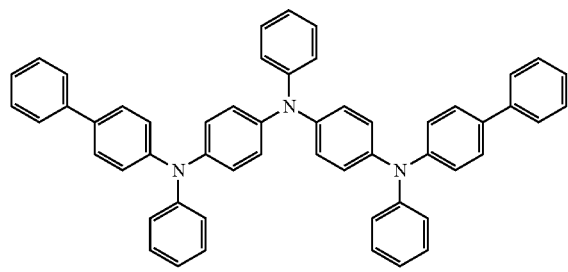
HIL-14
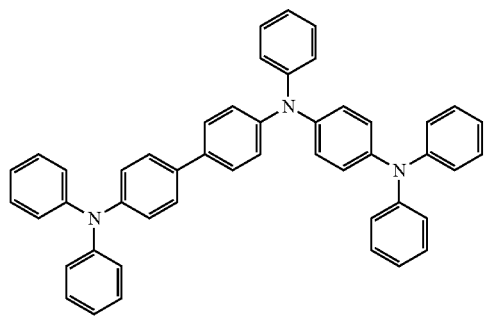
HIL-15
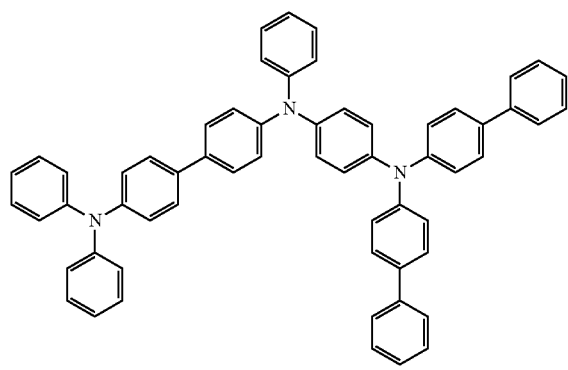
HIL-16
HIL-17
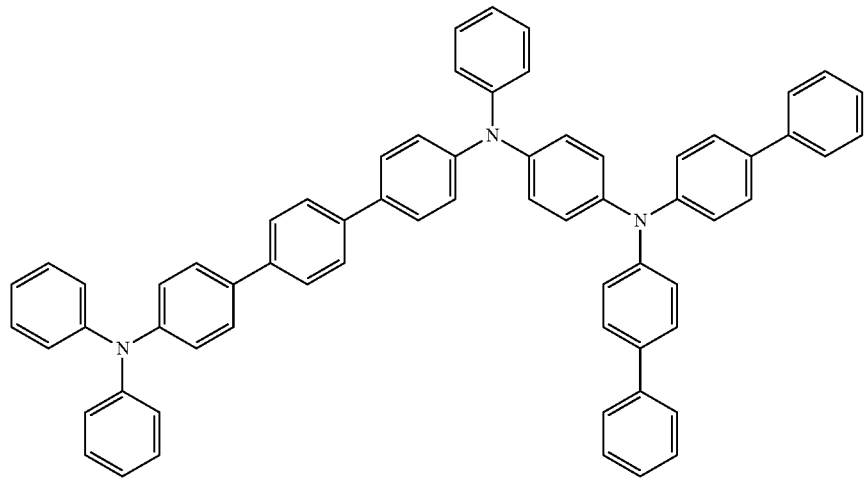
HIL-18
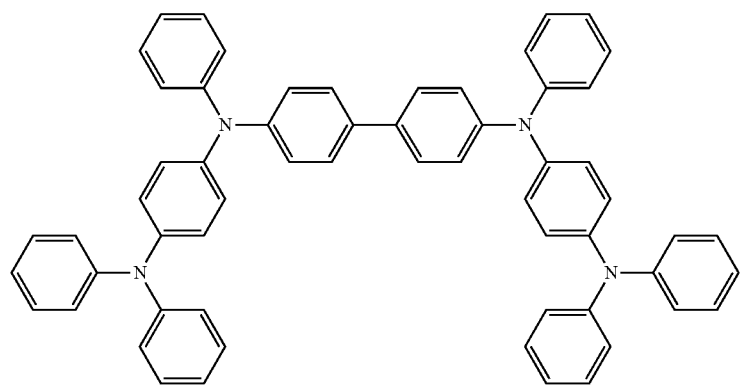

-continued
HIL-19
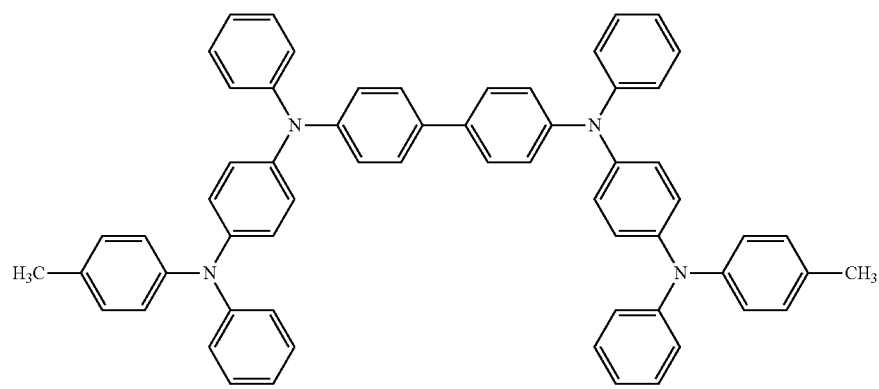
HIL-20
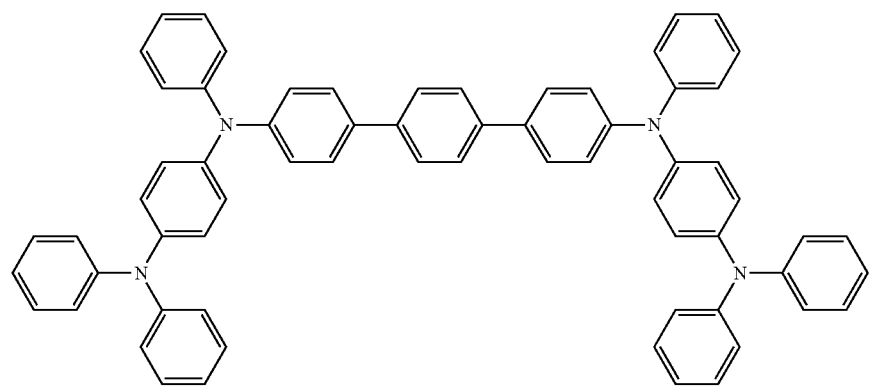
HIL-21
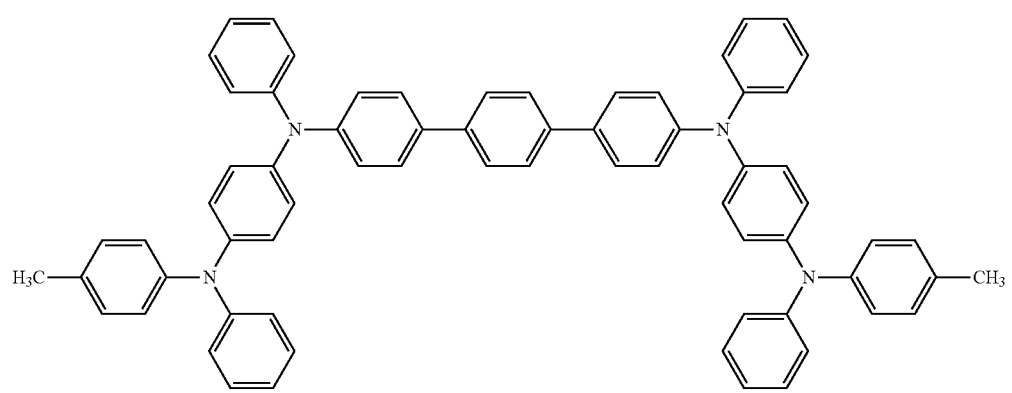

-continued
[Chem. 3]
HIL-22
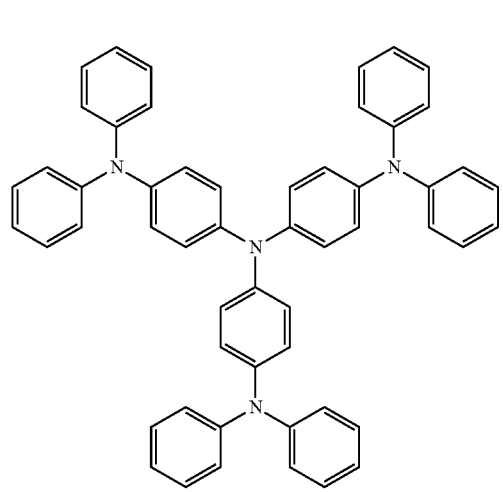
HIL-23
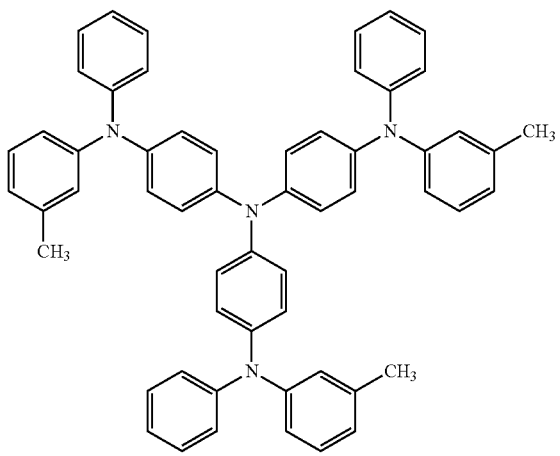
HIL-24
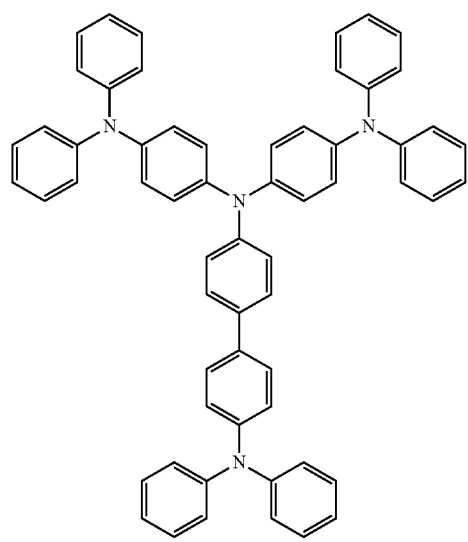
HIL-25
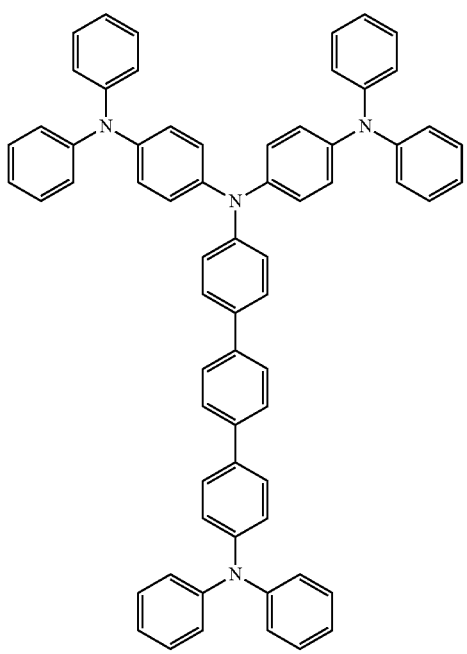

HIL-26

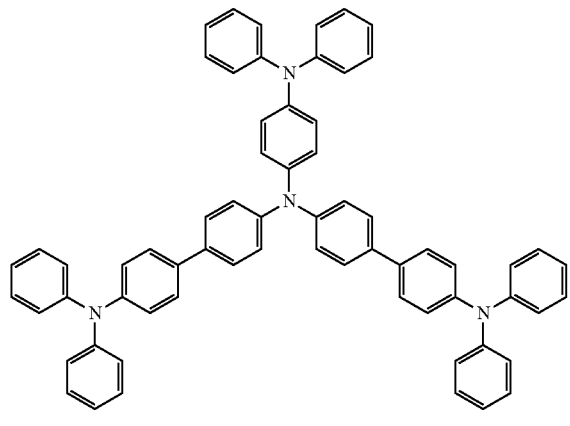

HIL-27

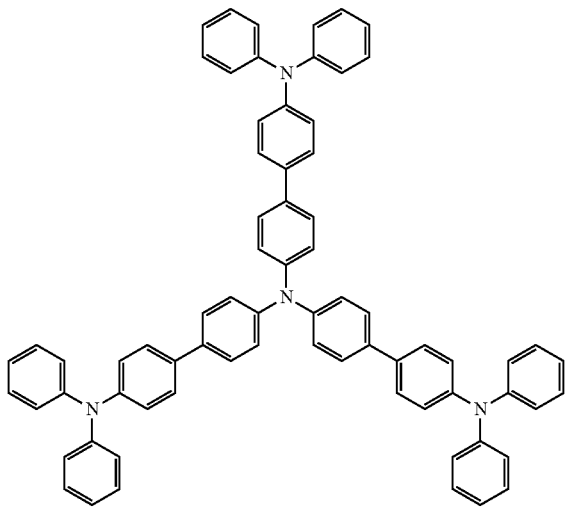

Further, it is preferred that a difference between the LUMO of the constituent material (the material having a hole injection property) of the hole injection layer 4 and the LUMO of a host material to be used in the light-emitting layer 5 is 0.5 eV or more. According to this, electrons coming out of the light-emitting layer 5 to the hole injection layer 4 are reduced, and thus, the luminous efficiency can be increased.

Further, the HOMO of the constituent material of the hole injection layer 4 is preferably 4.7 eV or more and 5.6 eV or less, and the LUMO of the constituent material of the hole injection layer 4 is preferably 2.2 eV or more and 3.0 eV or less.

Further, the constituent material (the material having a hole injection property) of the hole injection layer 4 preferably has a glass transition temperature (Tg) of 125° C. or higher. The light-emitting element 1 is used by being applied to, for example, a light-emitting element included in the below-mentioned authentication device, and in this case, it is used by applying a current between the anode and the cathode at a current density of 500 A/cm² or more and 1000 A/cm² or less. However, when a current is applied at such a current density, the temperature of the inside of the light-emitting element is raised by heat by the accumulation of heat, and due to this, each layer of the light-emitting element is fluidized, and as a result, a decrease in the luminous efficiency of the light-emitting element may be caused. On the other hand, by using a material having a Tg of 125° C. or higher as the constituent material of the hole injection layer 4, fluidization of the hole injection layer 4 can be suppressed or prevented, and therefore, the decrease in the luminous efficiency of the light-emitting element 1 due to this can be suppressed or prevented.

In addition, the hole injection layer 4 is preferably constituted by further including at least one of a first anthracene-based compound and a second anthracene-based compound contained in the below-mentioned electron transport layer 6 other than the material having a hole injection property (hole-injecting material). According to this, even if an electron comes out of the light-emitting layer 5 and the electron is injected into the hole injection layer 4, the electron can be transported by the first anthracene-based compound or the second anthracene-based compound, and therefore, alteration or deterioration of the material having a hole injection property due to the injected electron can be suppressed or prevented. As a result, the life of the light-emitting element 1 can be extended.

The average thickness of such a hole injection layer 4 is not particularly limited, but is preferably from about 5 to 90 nm, more preferably from about 10 to 70 nm.

(Light-Emitting Layer)

The light-emitting layer 5 emits light by applying a current between the anode 3 and the cathode 8 described above.

The light-emitting layer 5 is not particularly limited as long as it can emit light in a wavelength range of 700 nm or more (in a near-infrared range), but is constituted by including a light-emitting material which functions as a light-emitting dopant.

Examples of the light-emitting material include a thiadiazole-based compound which is a compound represented by the following general formula (IRD1) (hereinafter also simply referred to as "thiadiazole-based compound"), a benzo-bis-thiadiazole-based compound which is a compound represented by the following general formula (IRD2) (hereinafter also simply referred to as "benzo-bis-thiadiazole-based compound"), and a pyrromethene-based boron complex which is a compound represented by the following formula (IRD3) (hereinafter also simply referred to as "pyrromethene-based boron complex"), and among these, it is possible to use one type or two or more types in combination. According to this, the light-emitting layer 5 can be made to emit light in a wavelength range of 700 nm or more (in a near-infrared range).

[Chem. 4]

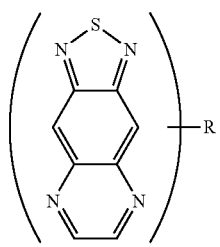

(IRD1)

[In the general formula (IRD1), R each independently represents an aryl group, an arylamino group, triarylamine, or a group containing at least one of the derivatives thereof.]

Examples of the group R in the general formula (IRD1) include an aryl group, an arylamino group, triarylamine, and derivatives thereof, and it is possible to use a group in which two or more types among these are combined. The light-emitting layer 5 containing the thiadiazole-based compound including such a group R as a light-emitting dopant can obtain light emission in a wavelength range of 700 nm or more (in a near-infrared range).

Specific examples of the thiadiazole-based compound including the group R as described above include compounds represented by the following formulae IRD1-1 to IRD1-12 and derivatives thereof.

[Chem. 5]

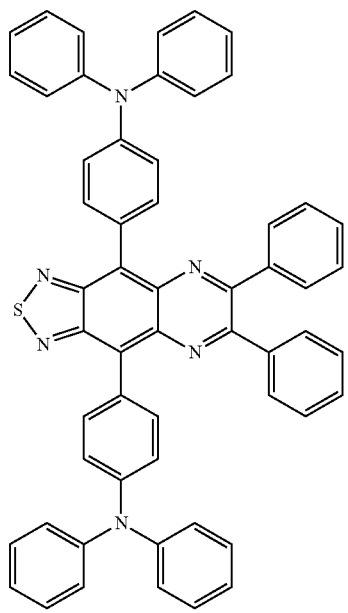

IRD1-2

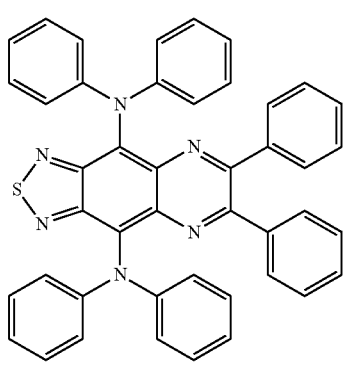

IRD1-3

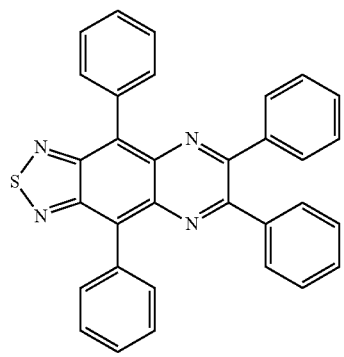

IRD1-1

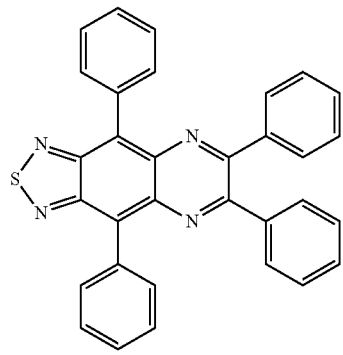

IRD1-4

IRD1-5
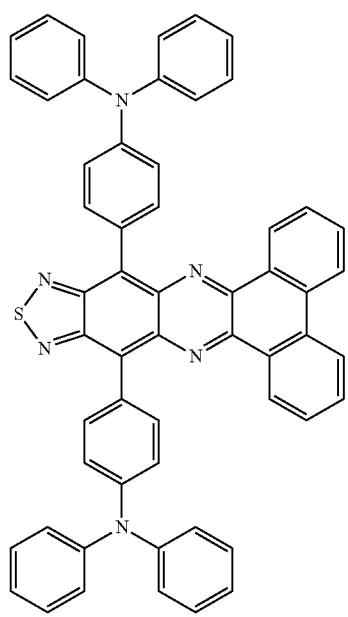
IRD1-6
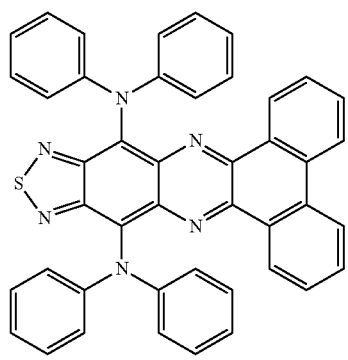
IRD1-7
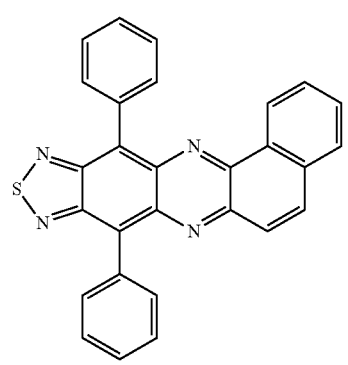
IRD1-8
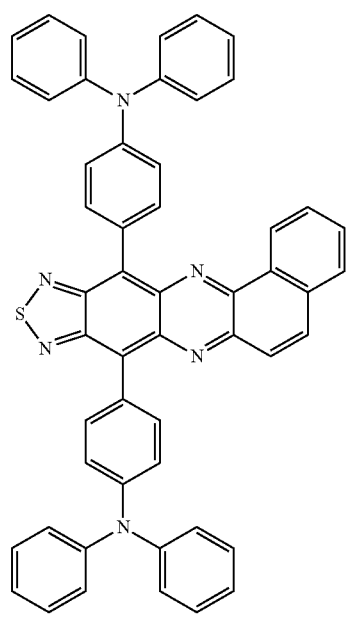
IRD1-9
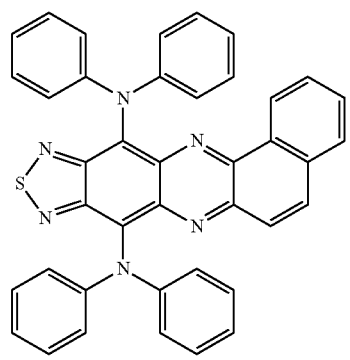
IRD1-10
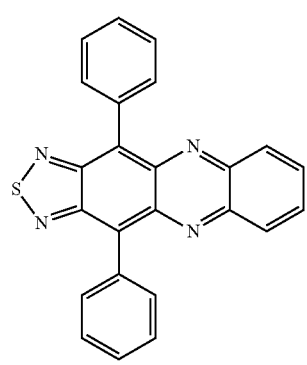

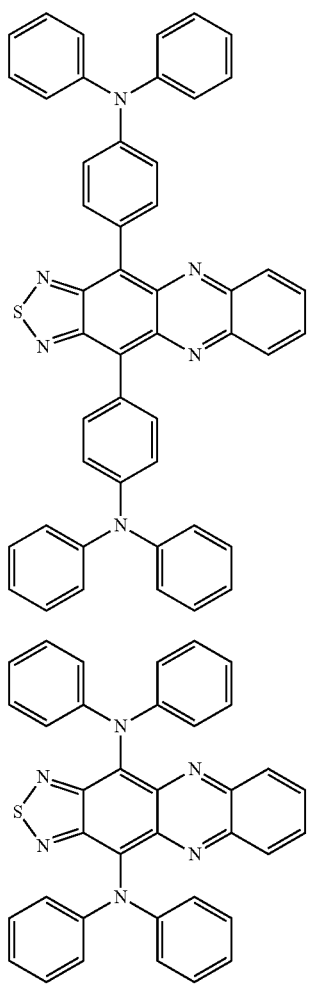

IRD1-11

IRD1-12

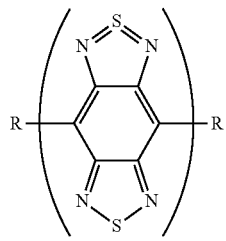

(IRD 2)

[In the general formula (IRD2), each R independently represents a phenyl group, a thiophenyl group, a furyl group, or a group containing at least one of the derivatives thereof.]

Each group R in the general formula (IRD2) is not particularly limited as long as it is a phenyl group, a thiophenyl group, a furyl group, or a group containing at least one of the derivatives thereof, however, for example, a group which contains a phenyl group, a thiophenyl group (thiophene group), a furyl group (furan group), an oxazole group, and an oxadiazole group or the like is exemplified, and the group R is preferably a group in which two or more types among these are combined. According to this, the light-emitting layer 5 containing the benzo-bis-thiadiazole-based compound including such a group R as a light-emitting dopant obtains light emission in a wavelength range of 700 nm or more (in a near-infrared range), particularly obtains light emission in a wavelength range of 850 nm or more and 1500 nm or less, which can be said to be a longer wavelength range.

Specific examples of the benzo-bis-thiadiazole-based compound including the group R as described above include compounds represented by the following formulae IRD2-1 to IRD2-21 and derivatives thereof.

[Chem. 7]

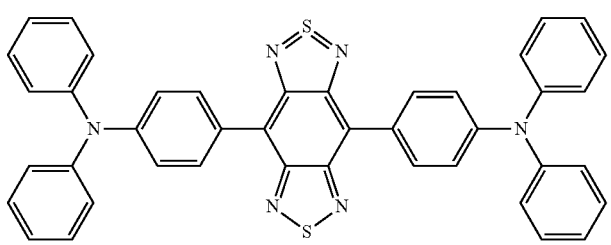

IRD2-1

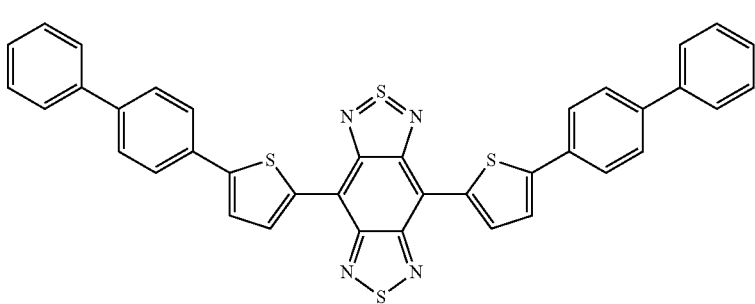

IRD2-2

-continued
IRD2-3
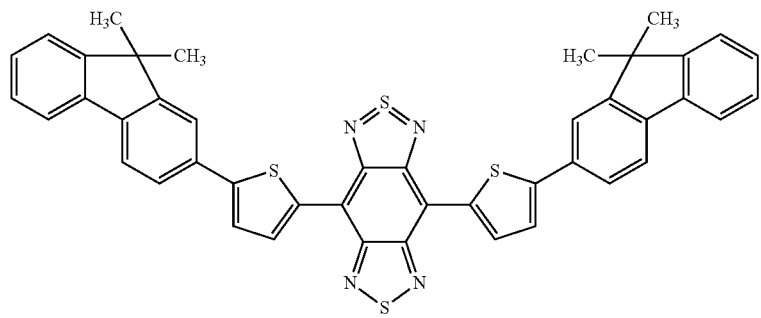
IRD2-4
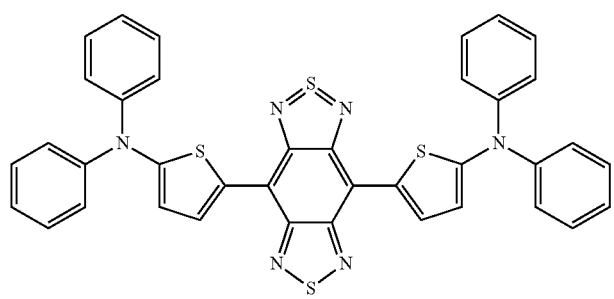
IRD2-5
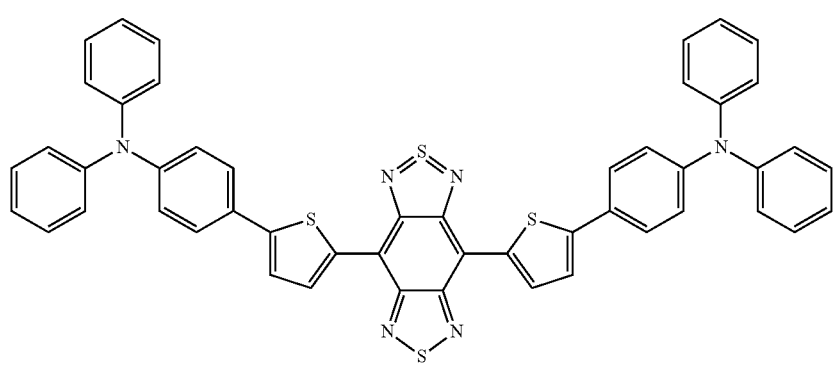
[Chem. 8]
IRD2-6
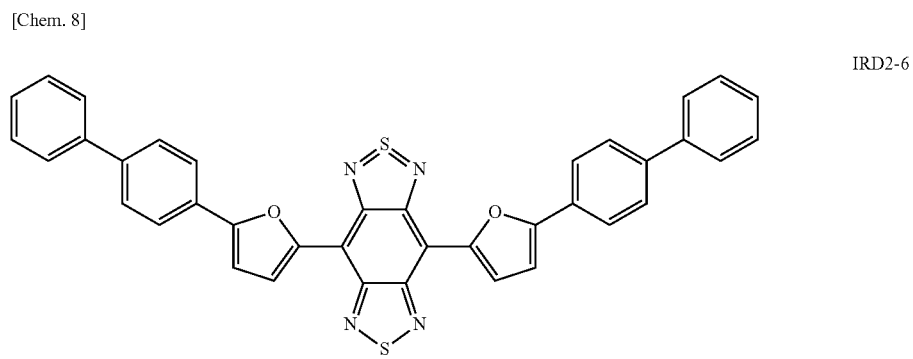
IRD2-7
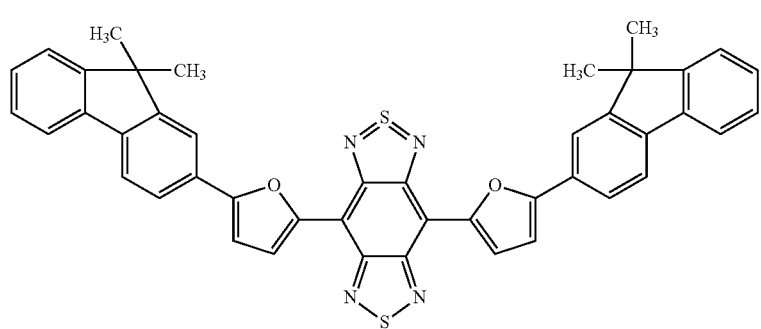

IRD2-8
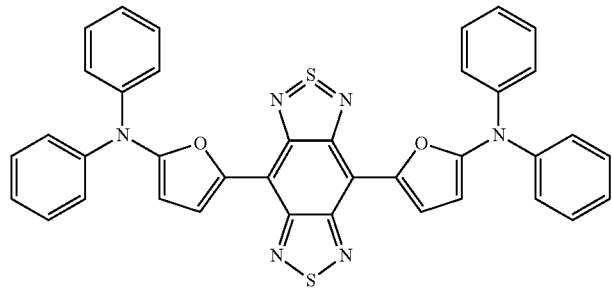
IRD2-9
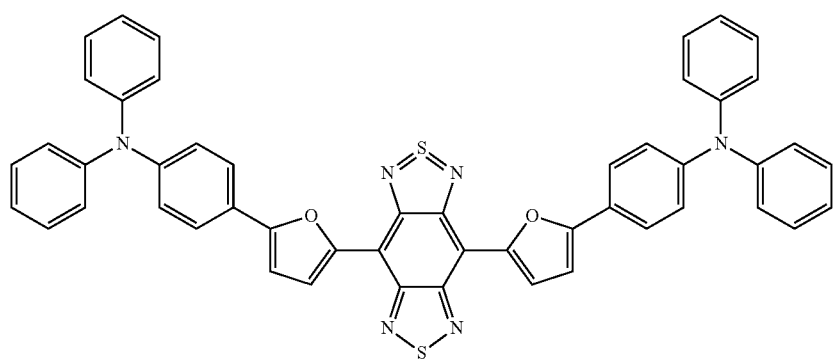
IRD2-10
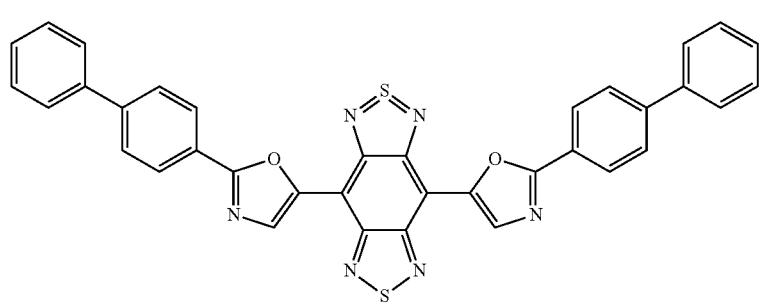
IRD2-11
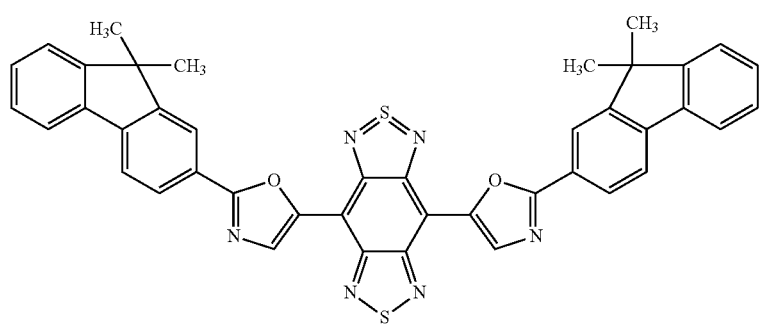
IRD2-12
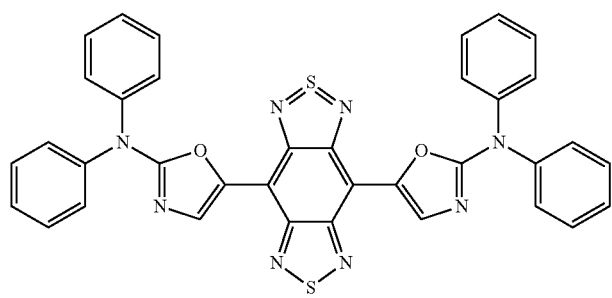

-continued
IRD2-13
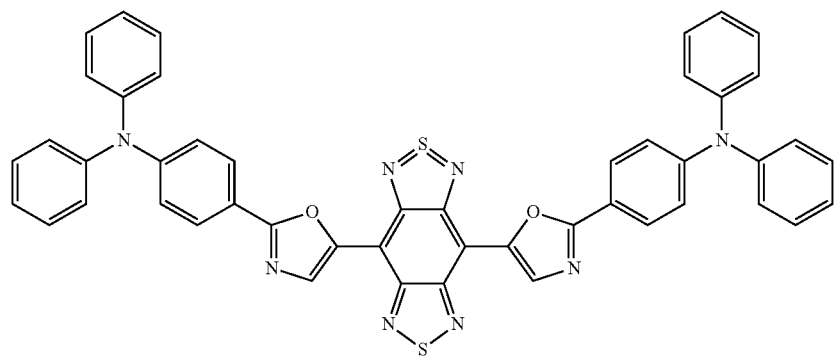
[Chem. 9]
IRD2-14
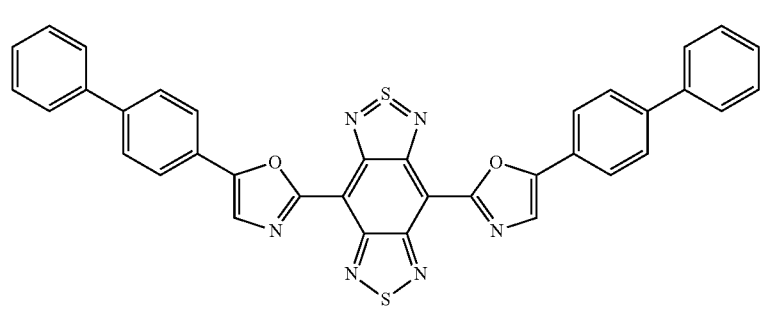
IRD2-15
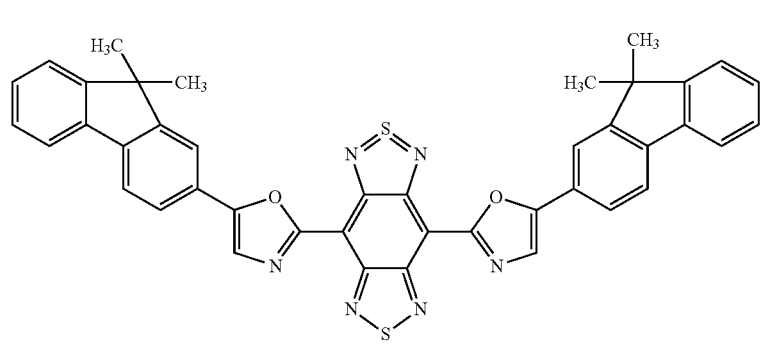
IRD2-16
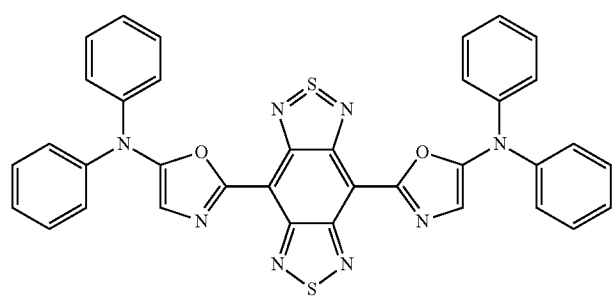

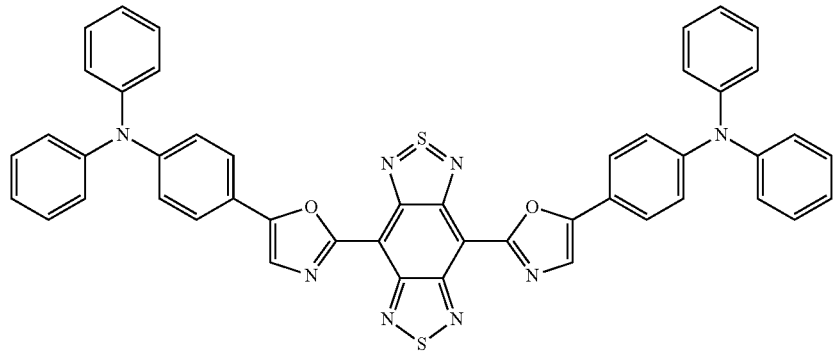
IRD2-17
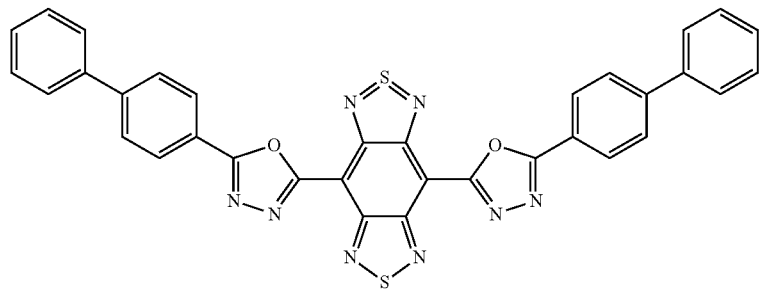
IRD2-18
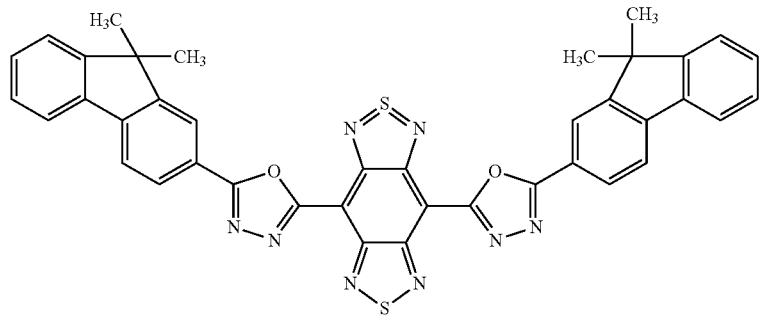
IRD2-19
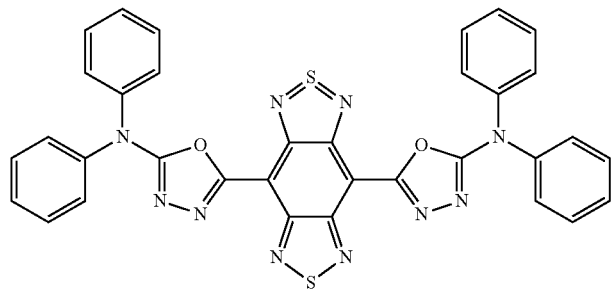
IRD2-20
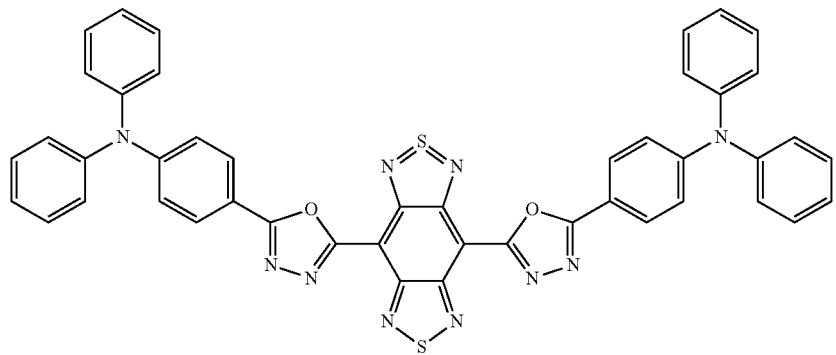
IRD2-21

[Chem. 10]

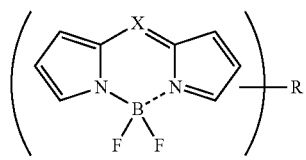

(IRD3)

[In the formula (IRD3), X represents a carbon atom to which hydrogen is attached or a nitrogen atom, and R represents a hydrogen atom, an alkyl group, an aryl group which may have a substituent, an allyl group, an alkoxy group, or a heterocyclic group.]

Here, the heterocyclic group to be used as R in the formula (IRD3) is not particularly limited, however, it is preferred to use a 5-membered heterocyclic group such as pyrrole, furan, or thiophene, or a 6-membered heterocyclic group such as pyridine.

The light-emitting layer 5 containing such a pyrromethene-based boron complex can obtain light emission in a wavelength range of 700 nm or more (in a near-infrared range).

Further, the light-emitting material to be used in the light-emitting layer 5 may be any as long as it is a compound represented by the above formula (IRD3) and can emit light in a near-infrared range, however, specific examples thereof include compounds represented by the following formulae IRD3-1 to IRD3-5 and derivatives thereof.

[Chem. 11]

IRD-3-1

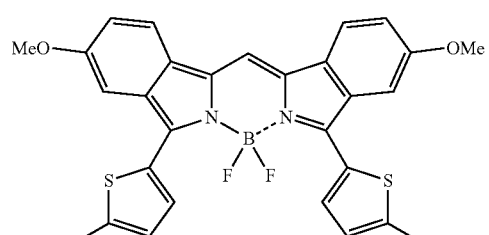

IRD-3-2

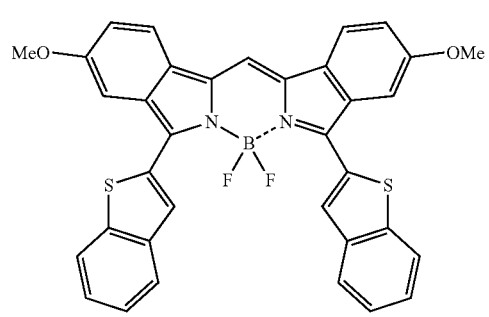

IRD 3-3

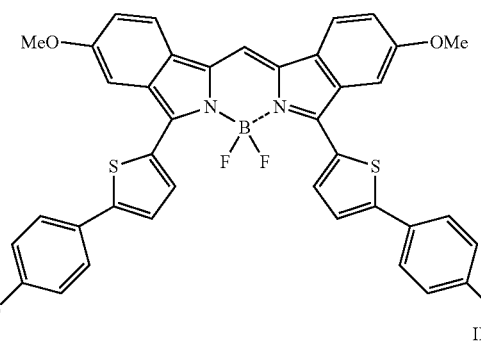

IRD 3-4

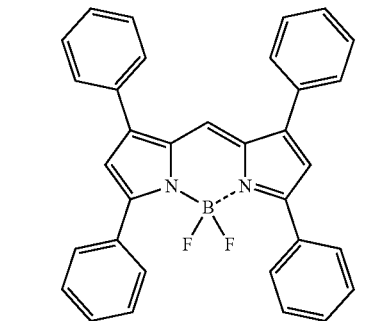

IRD 3-5

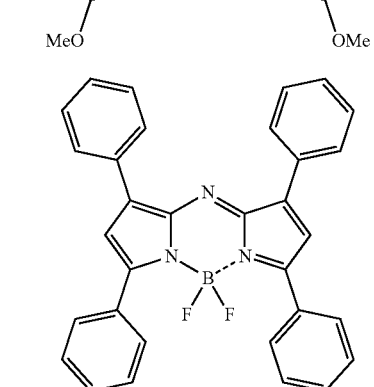

Incidentally, the light-emitting layer 5 may contain a light-emitting material (any of various types of fluorescent materials and various types of phosphorescent materials) other than the above-mentioned light-emitting material.

Further, the light-emitting layer 5 is constituted by including, in addition to the light-emitting material as described above, a host material to which this light-emitting material is added (held) as a guest material (dopant). This host material has a function to recombine a hole and an electron to generate an exciton, and also to transfer the energy of the exciton (Forster-transfer or Dexter-transfer) to the light-emitting material to excite the light-emitting material. Due to this, the luminous efficiency of the light-emitting element 1 can be increased. Such a host material can be used by, for example, doping the light-emitting material which is a guest material as a dopant into the host material.

The host material to be used in the light-emitting layer 5 is not particularly limited, but is particularly preferably an anthracene-based material which is a compound represented by the following formula IRH-1.

[Chem. 12]

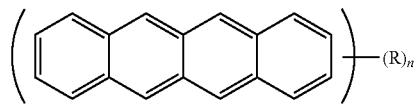

IRH-1

[In the formula IRH-1, n represents a natural number of 1 to 12, and R each independently represents a hydrogen atom, an alkyl group, an aryl group which may have a substituent, or an arylamino group.]

The various types of compounds (the benzo-bis-thiadiazole-based compounds, and the like) exemplified as the light-emitting material as described above have high polarity (large polarization), and therefore, in the case where such a compound is used as the light-emitting material, when the concentration thereof in the light-emitting layer is high, concentration quenching which is a phenomenon in which luminous efficiency is decreased due to the interaction between the molecules of the light-emitting material is likely to occur.

On the other hand, the tetracene-based material has low polarity (small polarization). Therefore, by using the tetracene-based material as the host material, the interaction between the molecules of the light-emitting material as described above is reduced, and therefore, the concentration quenching property can be reduced.

On the other hand, for example, in the case where Alq$_3$ having high polarity (large polarization) is used as the host material, the polarity of both of the host material and the light-emitting material is high (the polarization is large), and therefore, the interaction between the molecules of the light-emitting material is likely to occur, and thus, the concentration quenching property is increased.

Further, an anthracene-based material which is an acene-based material in the same manner as the tetracene-based material has an effect of reducing the concentration quenching property in the case where it is used as the host material, however, the luminous efficiency is decreased as compared with the case where the tetracene-based material is used as the host material. It is considered to be because when the anthracene-based material is used as the host material, the energy transfer from the host material to the light-emitting material is not sufficient, and the probability that an electron injected into the LUMO of the host material penetrates toward the anode side is high. In view of this, it cannot be said that the anthracene-based material is a suitable host material. Incidentally, such a phenomenon occurs similarly also in the case of a pentacene-based material other than the anthracene-based material.

For this reason, by using the tetracene-based material (acene-based material) as the host material, the luminous efficiency of the light-emitting element 1 can be increased, and therefore, the tetracene-based material is favorably used as the host material.

Further, the tetracene-based material has excellent resistance to electrons and holes. In addition, the tetracene-based material also has excellent thermal stability. Due to this, the life of the light-emitting element 1 can be extended. Further, since the tetracene-based material has excellent thermal stability, in the case where the light-emitting layer is formed using a gas phase deposition method, the decomposition of the host material due to heat during deposition can be prevented. Due to this, the light-emitting layer having excellent film quality can be formed. As a result, also from this point of view, the luminous efficiency of the light-emitting element 1 can be increased and also the life thereof can be extended.

In addition, the tetracene-based material hardly emits light itself, and therefore, it is also possible to prevent the host material from adversely affecting the emission spectrum of the light-emitting element 1.

Further, the tetracene-based material to be used as the host material is not particularly limited as long as it is represented by the above formula IRH-1 and also can exhibit the function as the host material as described above, however, it is preferred to use a compound represented by the following formula IRH-2, and it is more preferred to use a compound represented by the following formula IRH-3.

[Chem. 13]

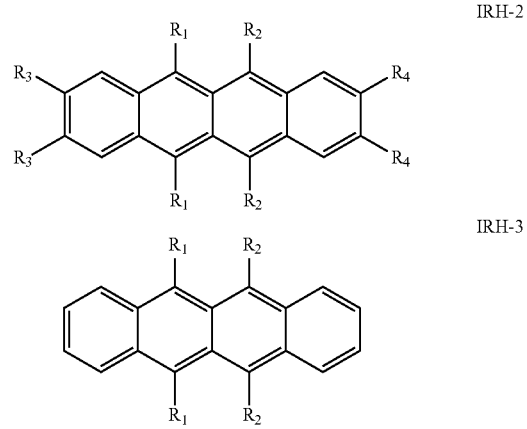

[In the formulae IRH-2 and IRH-3, $R_1$ to $R_4$ each independently represent a hydrogen atom, an alkyl group, an aryl group which may have a substituent, or an arylamino group. Further, $R_1$ to $R_4$ may be the same as or different from one another.]

Further, the tetracene-based material to be used as the host material is preferably constituted by a carbon atom and a hydrogen atom. According to this, the polarity of the host material is decreased, and thus, an undesirable interaction between the host material and the light-emitting material can be prevented from occurring. Due to this, the luminous efficiency of the light-emitting element 1 can be increased. In addition, the resistance of the host material to electrons and holes can be increased. As a result, the life of the light-emitting element 1 can be extended.

Specifically, as the tetracene-based material, for example, it is preferred to use compounds represented by the following formulae H-1 to H-27.

[Chem. 14]
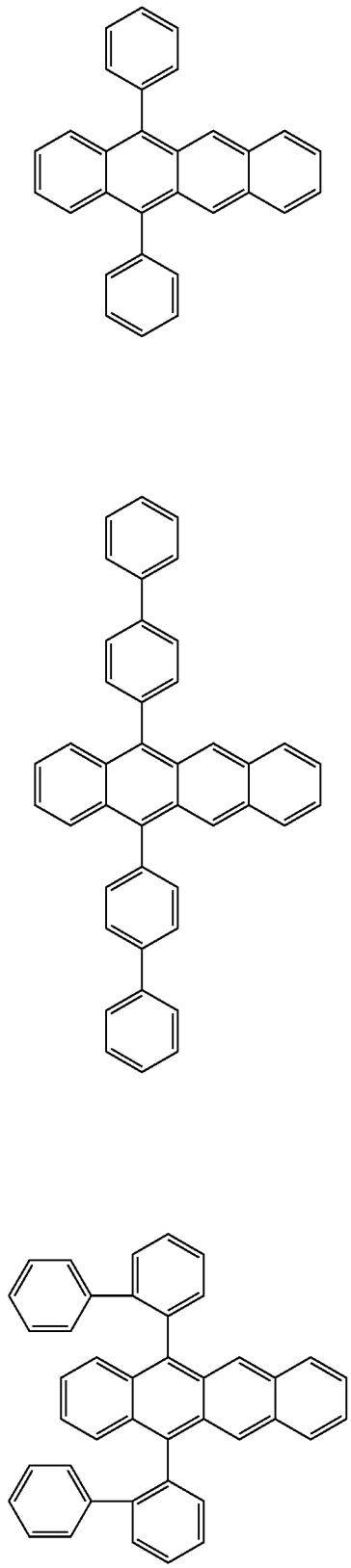
H-1
H-2
H-3
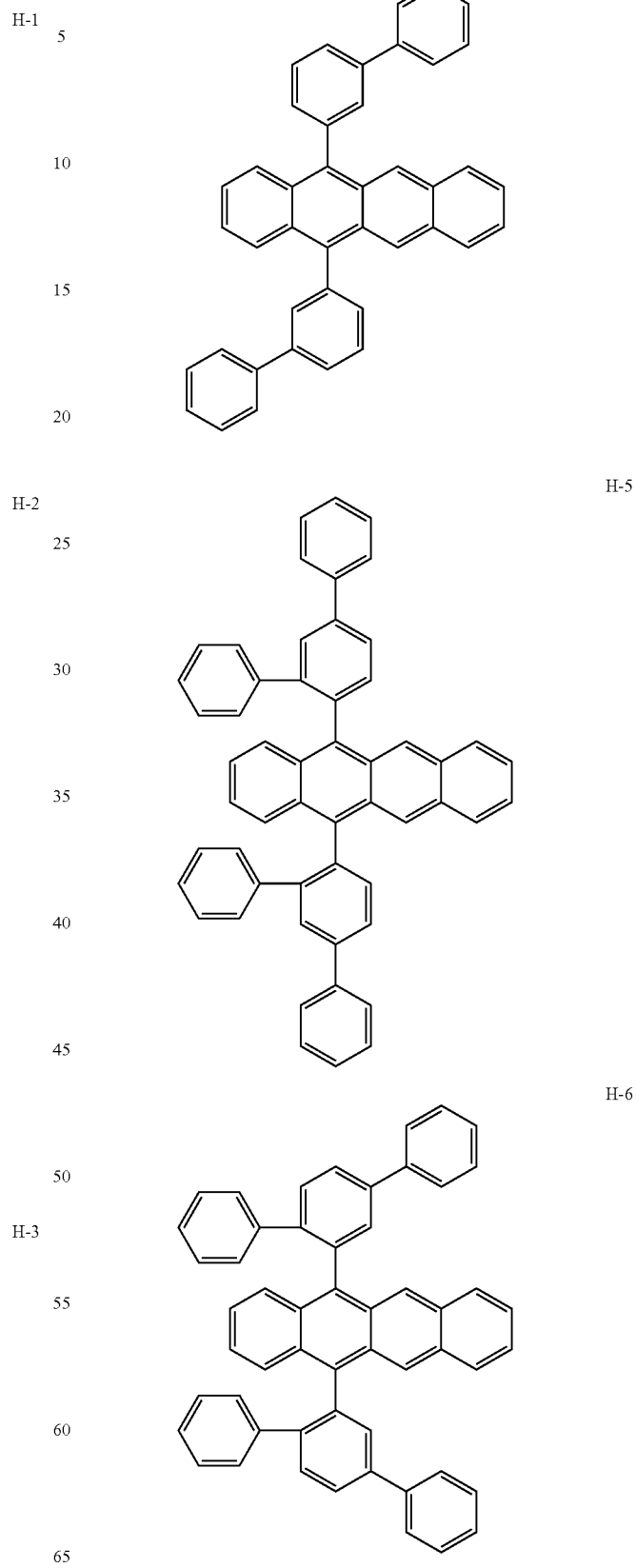
H-4
H-5
H-6

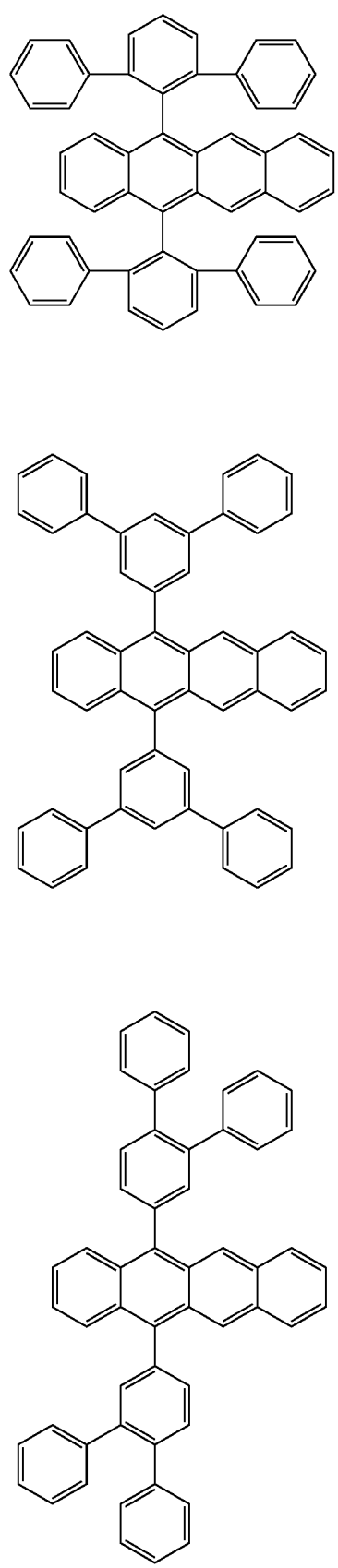
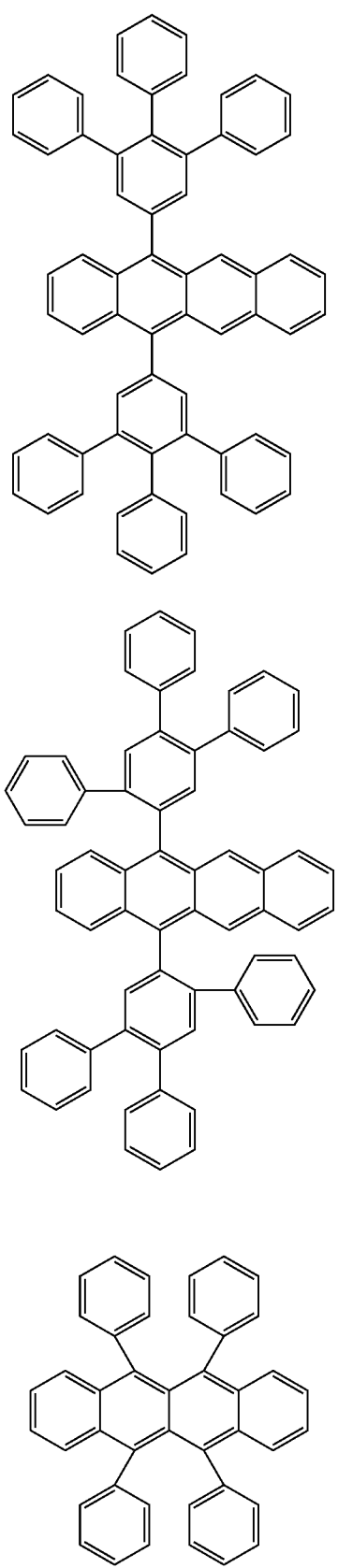
[Chem. 15]

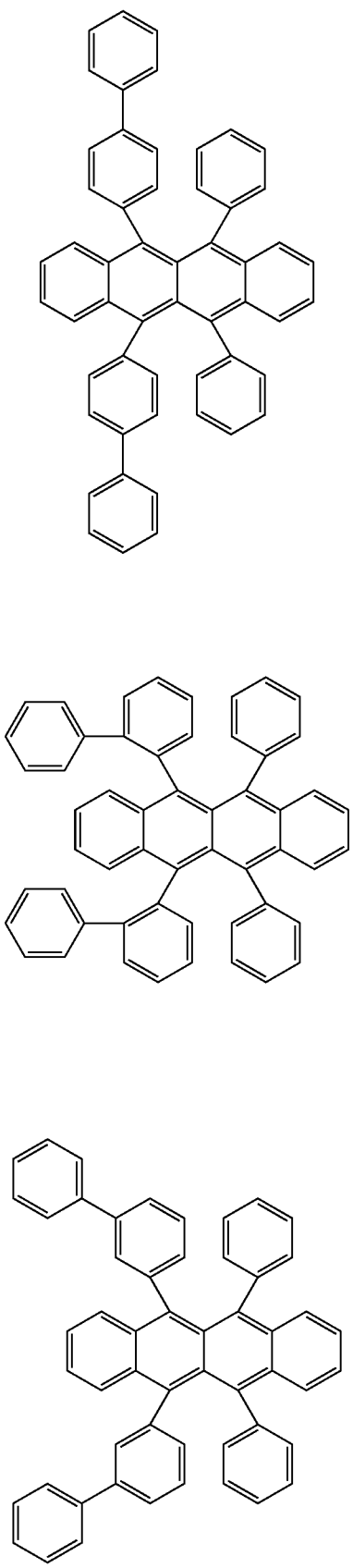
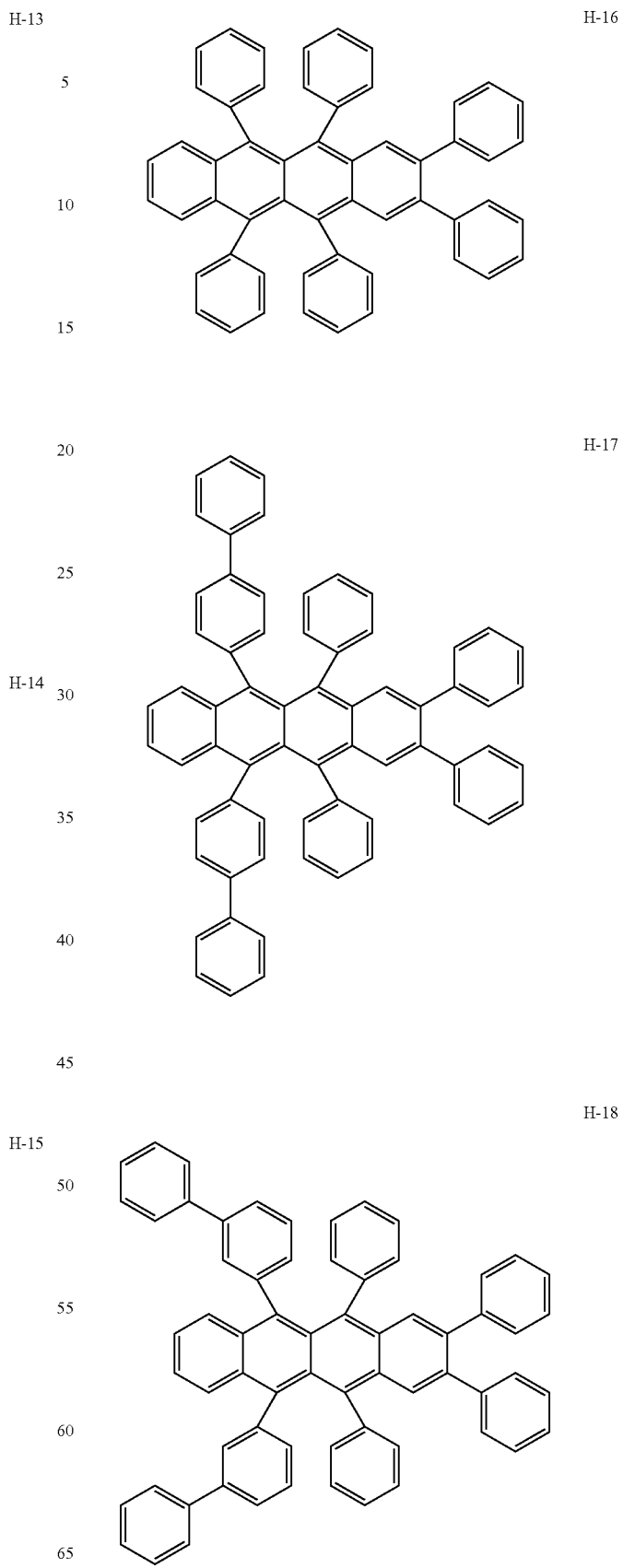

H-19
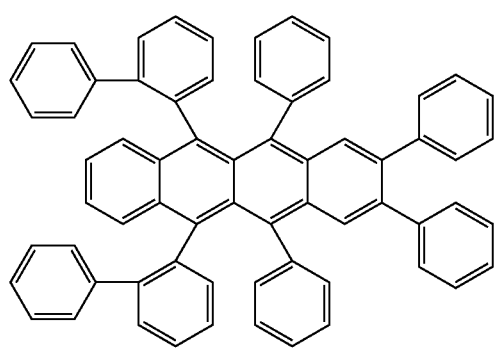
H-20
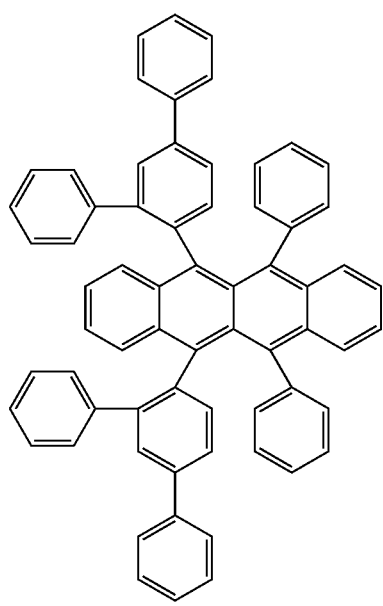
H-21
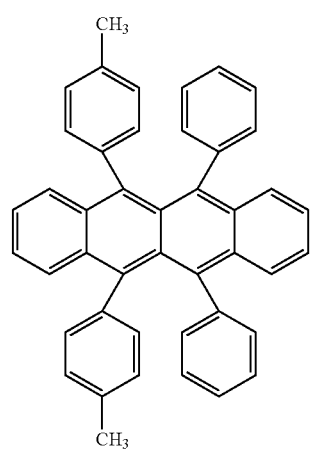
H-22
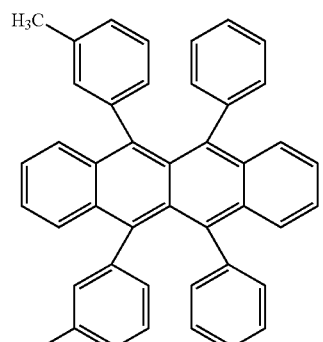
H-23
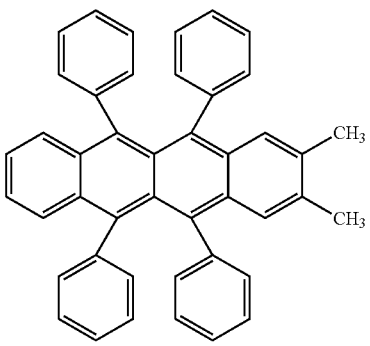
H-24

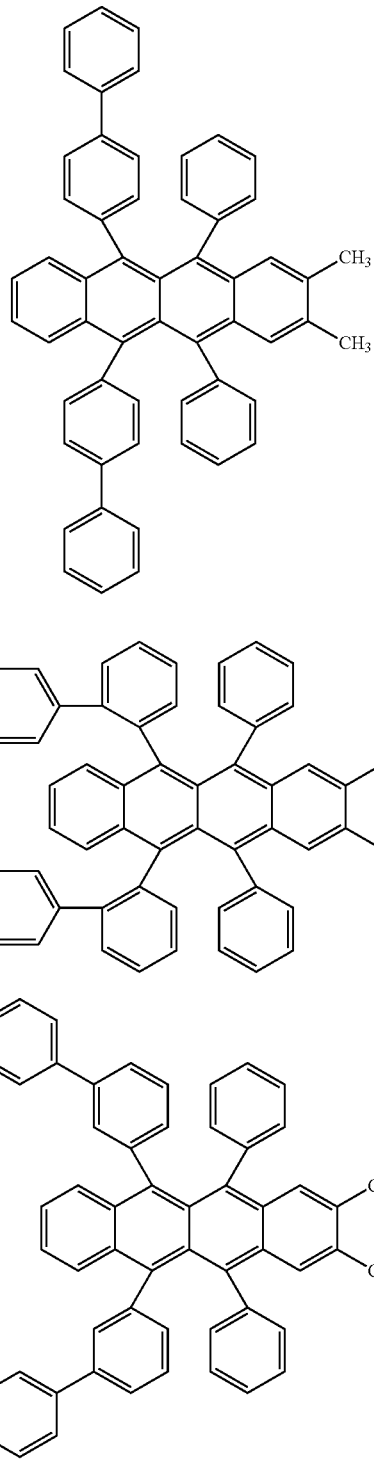

H-25

H-26

H-27

Further, the HOMO of the host material to be used in the light-emitting layer 5 is preferably 5.0 eV or more and 5.8 eV or less, and the LUMO of the constituent material of the hole injection layer 4 is preferably 2.5 eV or more and 3.6 eV or less.

The content (doping amount) of the light-emitting material in the light-emitting layer 5 containing such a light-emitting material and a host material is preferably 0.5 wt % or more and 5.0 wt % or less, more preferably 0.75 wt % or more and 2.0 wt % or less, further more preferably 1.0 wt % or more and 2.0 wt % or less. According to this, an excellent balance between the luminous efficiency and the life of the light-emitting element 1 can be achieved.

Further, it is preferred that the light-emitting material and the host material each have a glass transition temperature (Tg) of 125° C. or higher. According to this, even if the light-emitting element 1 is used by applying a current between the anode 3 and the cathode 8 at a current density of about 500 A/cm$^2$ or more and 1000 A/cm$^2$ or less, fluidization of the light-emitting layer 5 can be suppressed or prevented, and therefore, the decrease in the luminous efficiency of the light-emitting element 1 due to this can be suppressed or prevented.

Further, the average thickness of the light-emitting layer 5 is preferably 10 nm or more and 50 nm or less, more preferably from 25 nm or more and 50 nm or less. According to this, while suppressing the driving voltage of the light-emitting element 1, the life of the light-emitting element 1 can be extended.

(Electron Transport Layer)

The electron transport layer 6 is provided between the light-emitting layer 5 and the electron injection layer 7, and has a function to transport electrons injected from the cathode 8 through the electron injection layer 7 to the light-emitting layer 5.

In this invention, as shown in FIG. 1, this electron transport layer 6 includes the first electron transport layer 6b located on the cathode 8 side and the second electron transport layer 6a located on the light-emitting layer 5 side. That is, the electron transport layer 6 includes the first electron transport layer 6b and the second electron transport layer 6a provided between the first electron transport layer 6b and the light-emitting layer 5.

<First Electron Transport Layer>

The first electron transport layer 6b contains a first anthracene-based compound, which has an anthracene skeleton and a nitrogen-containing heterocyclic skeleton, and has an average thickness of less than 8 nm.

Here, the compound having an anthracene skeleton is a compound having an excellent electron transport property. Further, the compound having a nitrogen-containing heterocyclic skeleton is a compound having an excellent property of electron injection from the cathode 8 through the electron injection layer 7. Due to this, by using the first anthracene-based compound, which has an anthracene skeleton and a nitrogen-containing heterocyclic skeleton, as the constituent material of the first electron transport layer 6b provided in contact with the electron injection layer 7, the first electron transport layer 6b has both of an excellent electron transport property and an excellent property of electron injection from the cathode 8 through the electron injection layer 7.

Further, the average thickness of the first electron transport layer 6b is set thin such that it is less than 8 nm.

In the first electron transport layer 6b, the first anthracene-based compound, which has a nitrogen-containing heterocyclic skeleton, is used as the constituent material thereof, and the first anthracene-based compound shows crystallinity because of having such a nitrogen-containing heterocyclic skeleton. Due to this, when the light-emitting element 1 is used by repeatedly applying a current between the anode 3 and the cathode 8 at a current density of about 500 A/cm$^2$ or more and 1000 A/cm$^2$ or less, the first anthracene-based compound shows a tendency to crystallize in the first electron transport layer 6b. However, in the invention, the average thickness of the first electron transport layer 6b is set thin such that it is less than 8 nm, and therefore, the alteration or deterioration of the first electron transport layer 6b due to crystallization of the first anthracene-based compound can be suppressed, and as a result, the life of the light-emitting element 1 is extended.

Further, a hole comes out of the second electron transport layer 6a and even if the hole is injected into the first electron transport layer 6b, since the thickness of the first electron transport layer 6b is thin, the hole further comes out of the first electron transport layer 6b and disappears in the electron injection layer 7 or the cathode 8. Due to this, also from this point of view, the alteration or deterioration of the first electron transport layer 6b can be suppressed, and as a result, the life of the light-emitting element 1 is extended.

Incidentally, the average thickness of the first electron transport layer 6b may be less than 8 nm, but is particularly preferably 3 nm or more and 5 nm or less. According to this, while exhibiting the function as the first electron transport layer 6b, an effect obtained by setting the film thickness of the first electron transport layer 6b thin can be more remarkably exhibited.

Further, the nitrogen-containing heterocyclic skeleton is not particularly limited as long as it has a nitrogen atom in a heterocyclic ring, however, examples thereof include an azaindolizine skeleton, an oxadiazole skeleton, a pyridine skeleton, a pyrimidine skeleton, a quinoxaline skeleton, and a phenanthroline skeleton such as 2,9-dimethyl-4,7-diphenyl-1,10-phenanthroline (BCP), and above all, an azaindolizine skeleton is preferred. The azaindolizine skeleton is a skeleton having low affinity for a metal material. Therefore, the decrease in the electron transport property and the electron injection property of the first electron transport layer 6b due to the incorporation of an alkali metal, an alkaline earth metal, or the like contained in the electron injection layer 7 in contact with the first electron transport layer 6b can be suppressed or prevented.

Accordingly, as the first anthracene-based compound, an azaindolizine-based compound having both of an anthracene skeleton and an azaindolizine skeleton in the molecule (hereinafter also simply referred to as "azaindolizine-based compound") is preferably used. According to this, electrons can be efficiently transported and injected into the second electron transport layer 6a over a long period of time. As a result, the luminous efficiency of the light-emitting element 1 can be increased.

In the azaindolizine-based compound, the number of azaindolizine skeletons and the number of anthracene skeletons contained in one molecule are both preferably one or two. According to this, electrons can be more efficiently transported and injected into the second electron transport layer 6a over a long period of time. As a result, the luminous efficiency of the light-emitting element 1 can be further increased.

Examples of the azaindolizine-based compound include compounds represented by the following general formula ETL1, and more specific examples thereof include compounds represented by the following formulae ETL1-1 to ETL1-24, compounds represented by the following formulae ETL1-25 to ETL1-36, and compounds represented by the following formulae ETL1-37 to ETL1-56.

[Chem. 16]

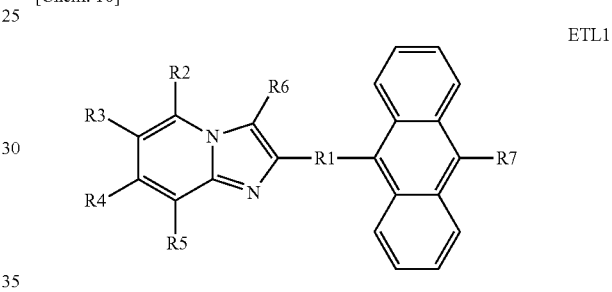

[In the formula ETL1, R1 to R7 each independently represent a hydrogen atom, an alkyl group, an aryl group which may have a substituent, or an arylamino group. Further, R1 to R7 may be the same as or different from one another.]

[Chem. 17]

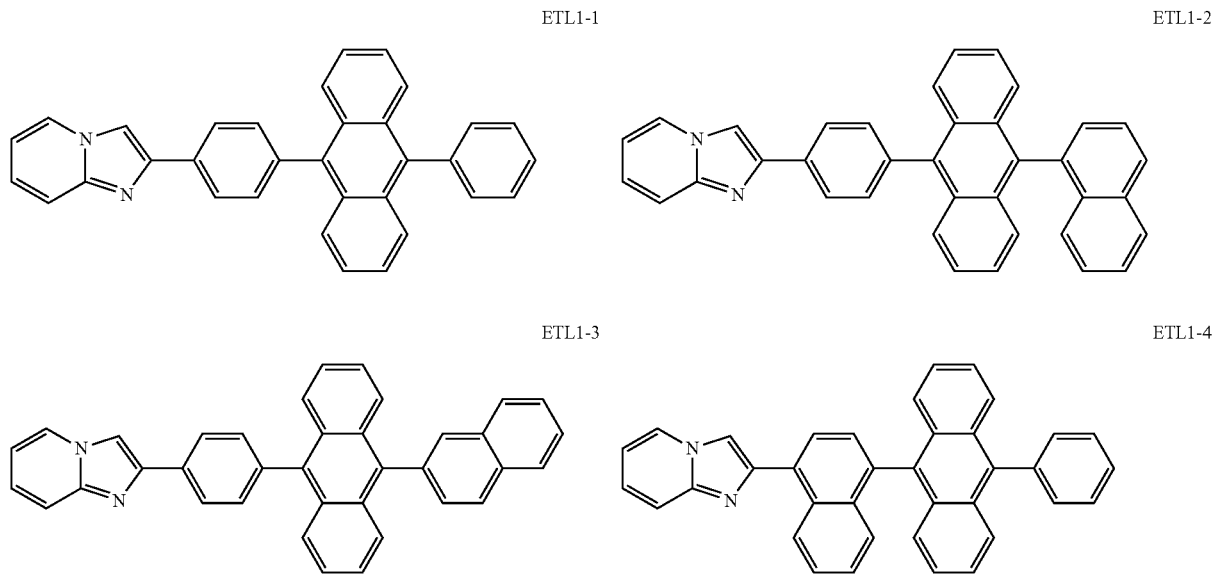

-continued
ETL1-5 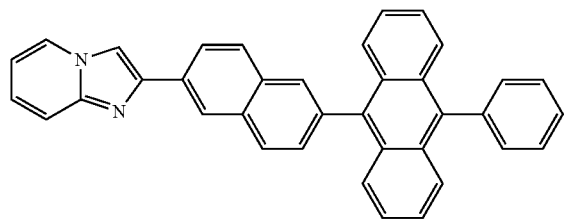
ETL1-6 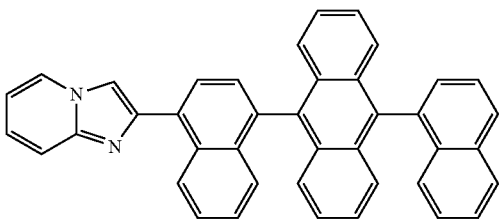
ETL1-7 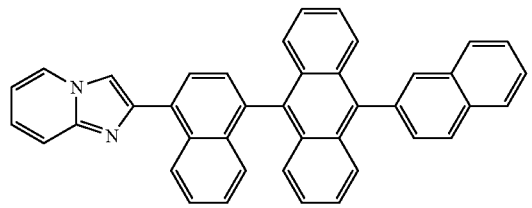
ETL1-8 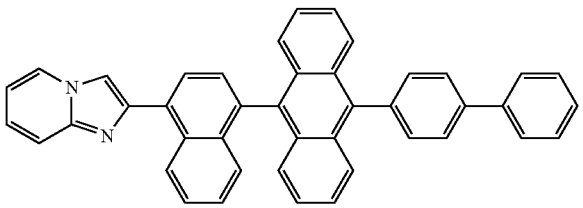
ETL1-9 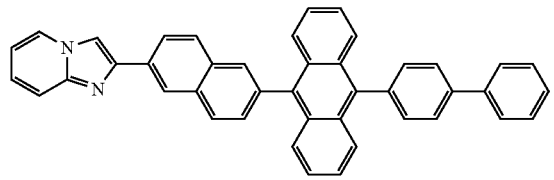
ETL1-10 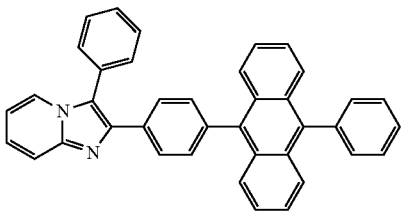
ETL1-11 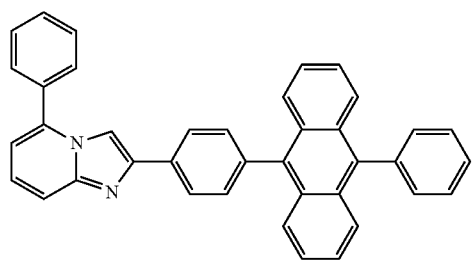
ETL1-12 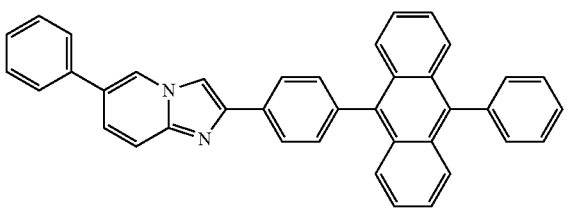
ETL1-13 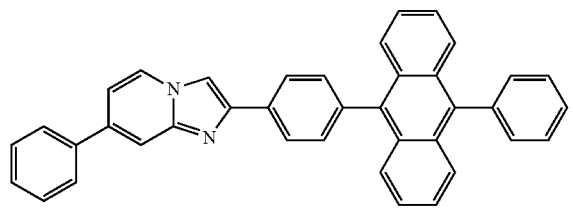
ETL1-14 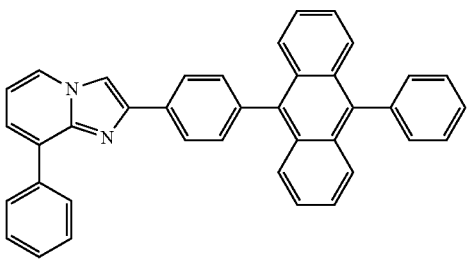
ETL1-15 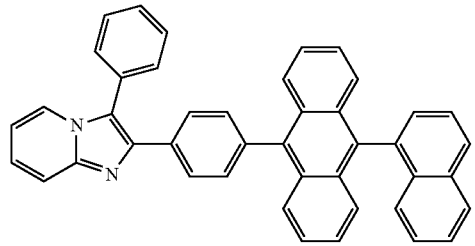
ETL1-16 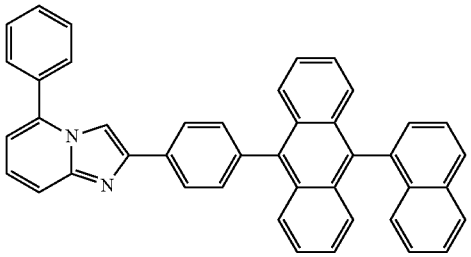

-continued
ETL1-17
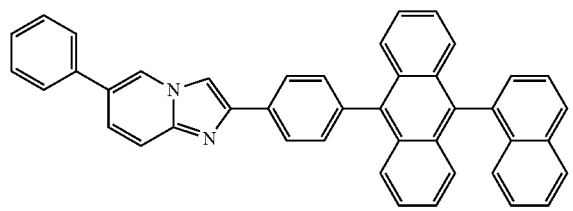
ETL1-18
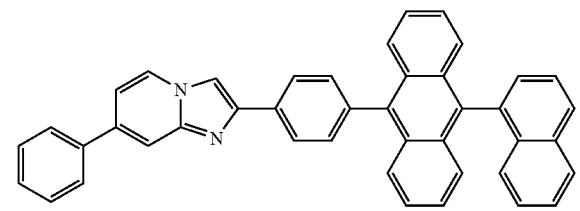
ETL1-19
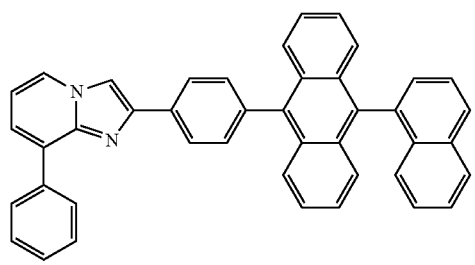
ETL1-20
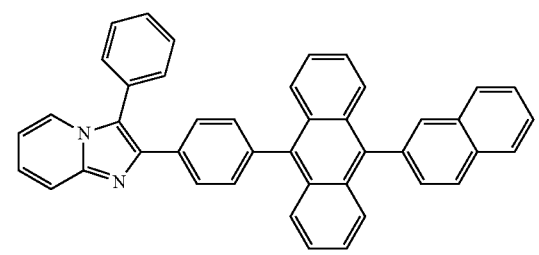
ETL1-21
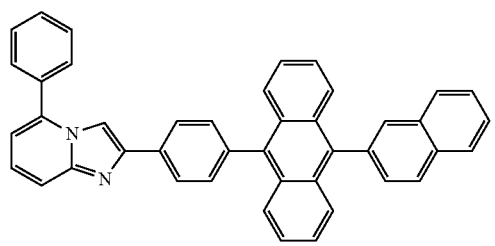
ETL1-22
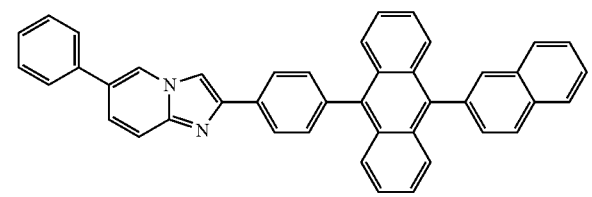
ETL1-23
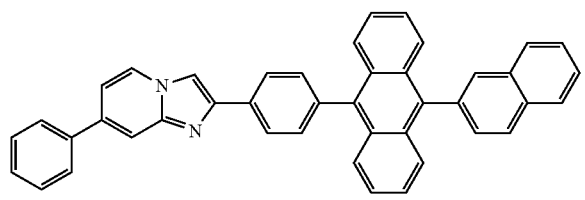
ETL1-24
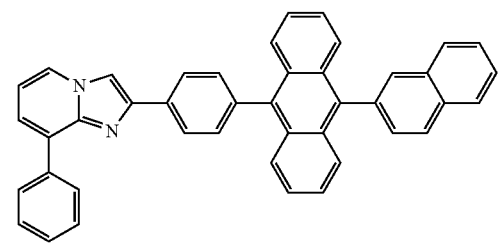
[Chem. 18]
ETL1-25
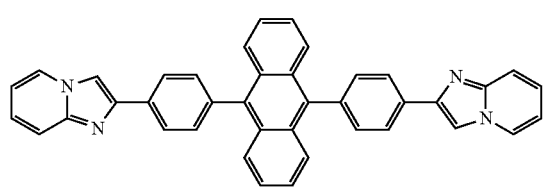
ETL1-26
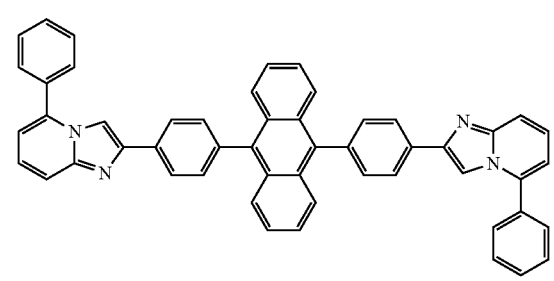

-continued
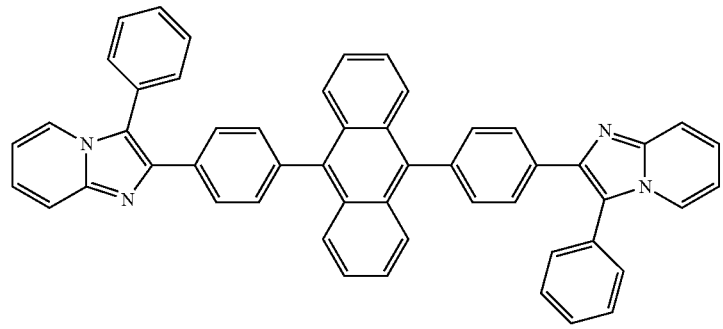
ETL1-27
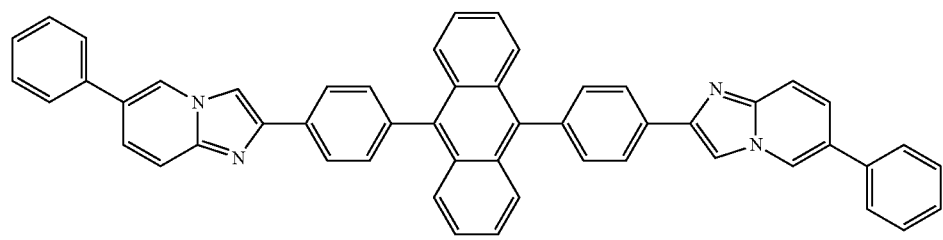
ETL1-28
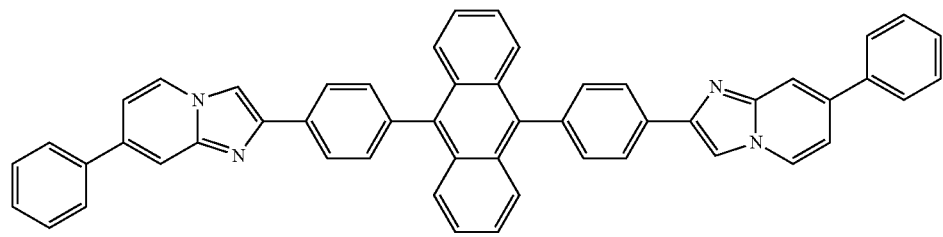
ETL1-29
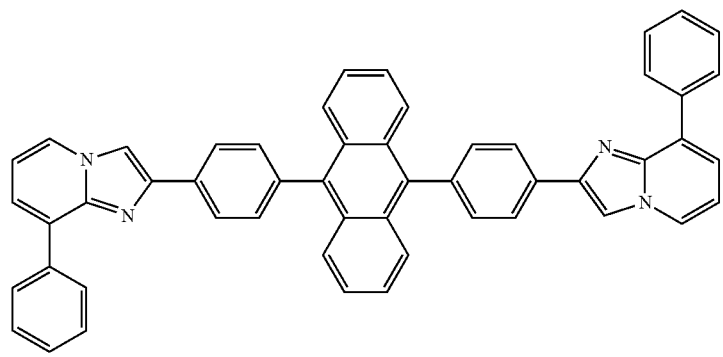
ETL1-30
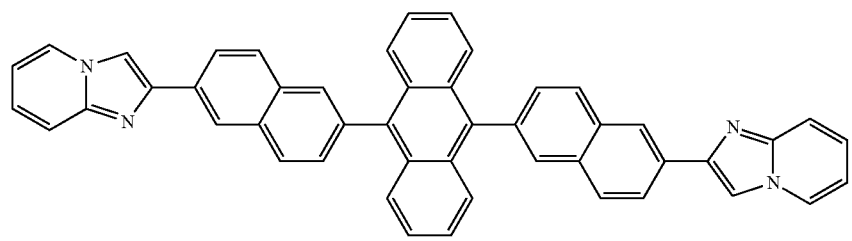
ETL1-31

ETL1-32
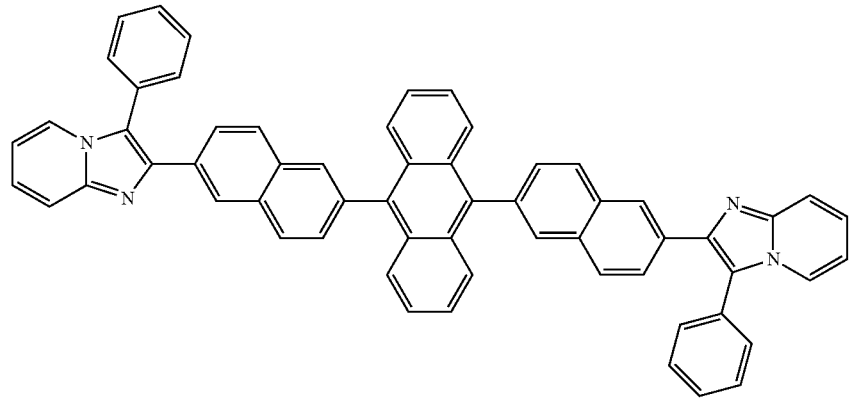
ETL1-33
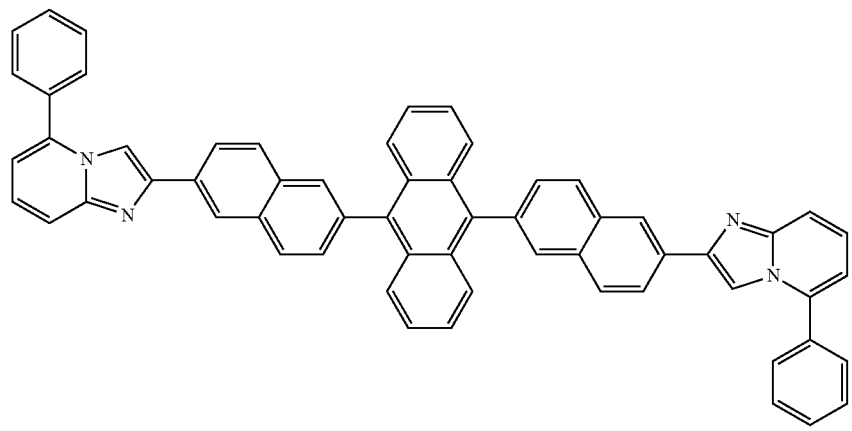
ETL1-34
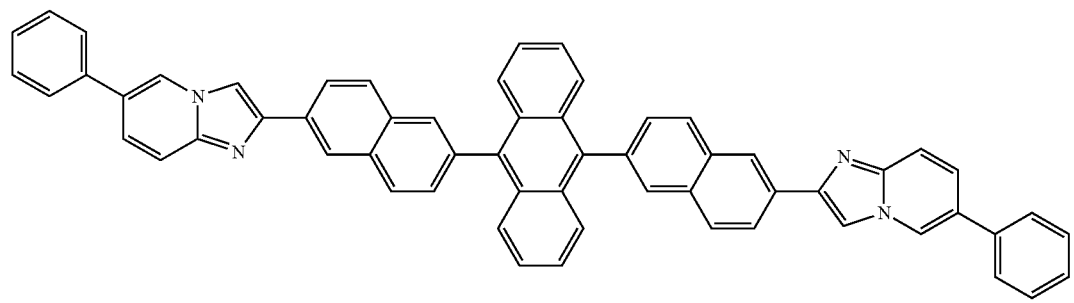
ETL1-35
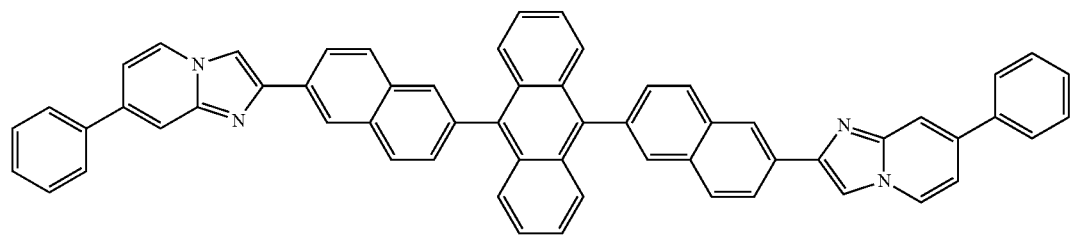

ETL1-36
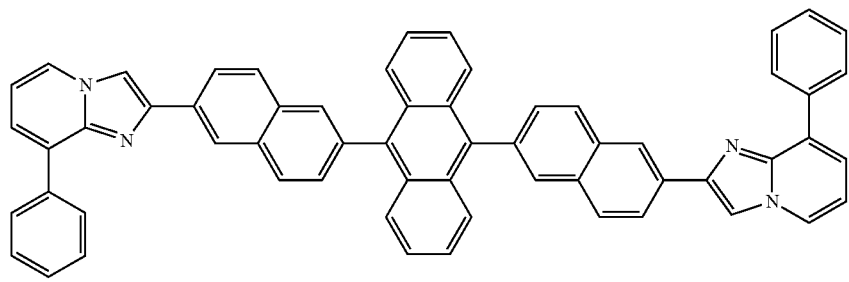
[Chem. 19]
ETL1-37 ETL1-38
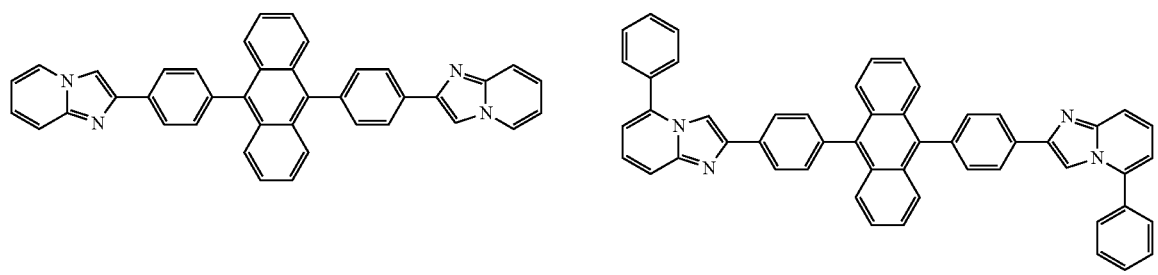
ETL1-39
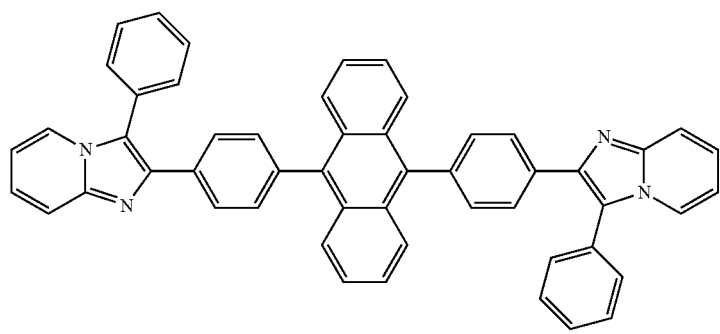
ETL1-40
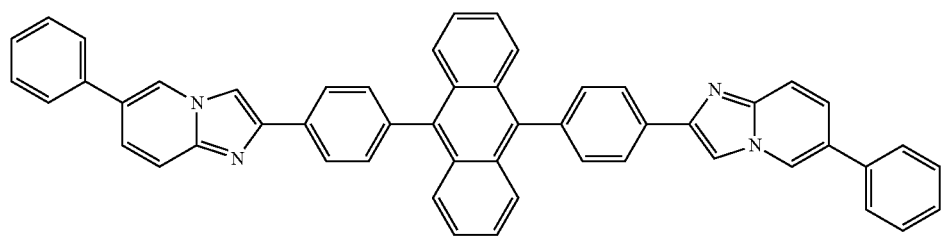
ETL1-41 ETL1-42
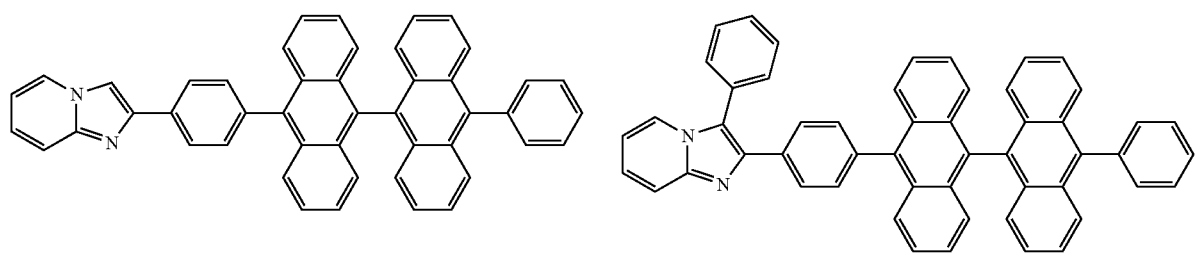

-continued
ETL1-43
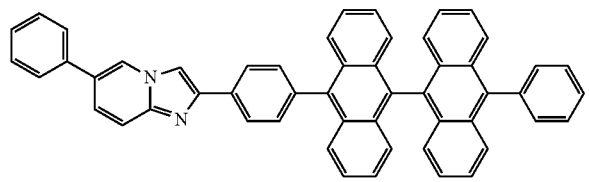
ETL1-44
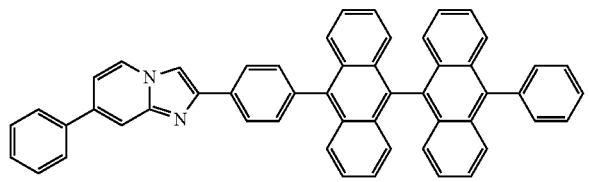
ETL1-45
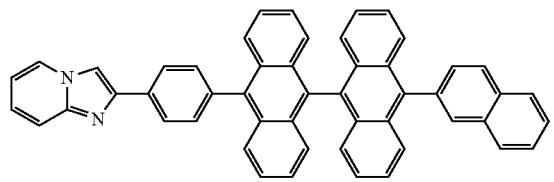
ETL1-46
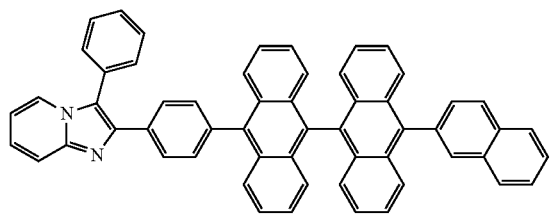
ETL1-47
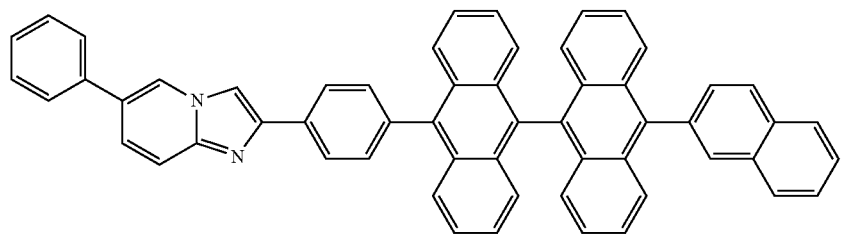
ETL1-48
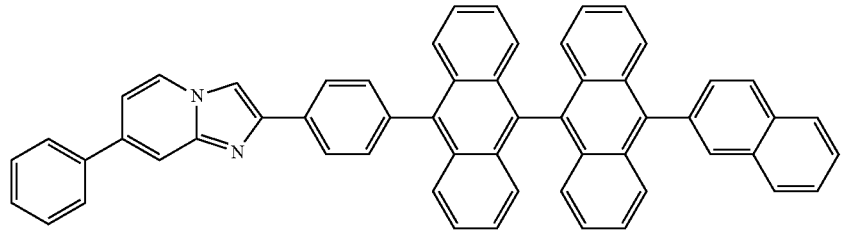
ETL1-49
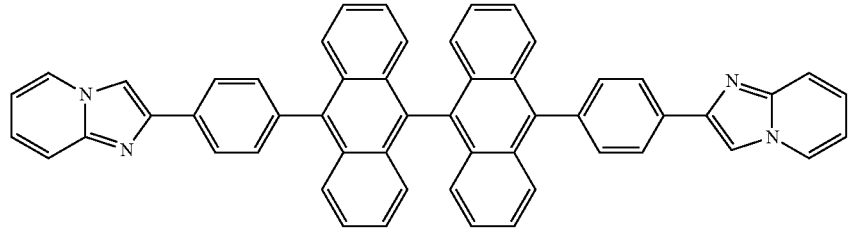
ETL1-50
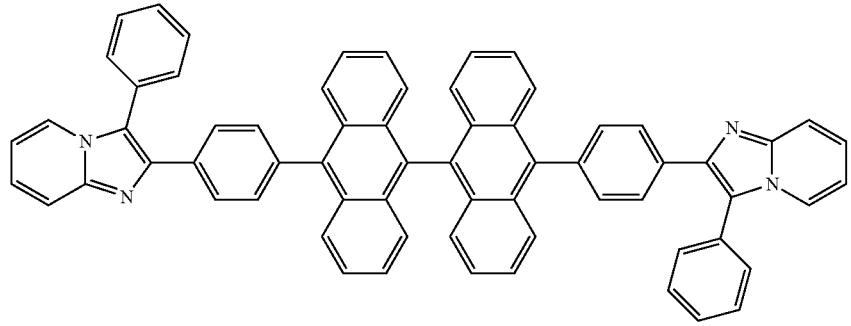

ETL1-51
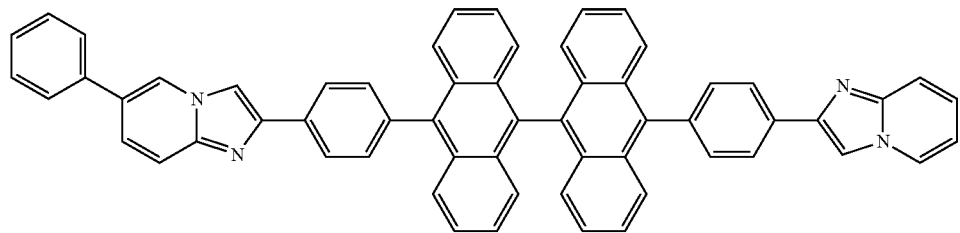
ETL1-52
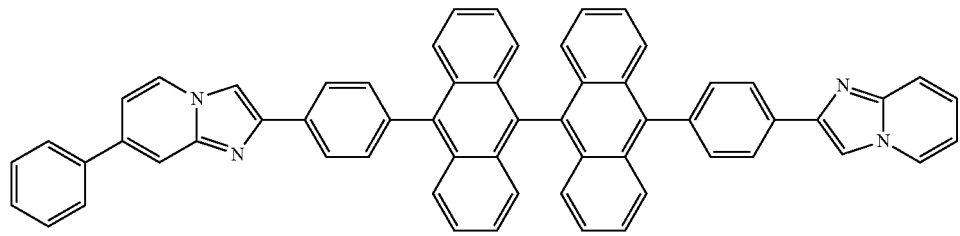
ETL1-53
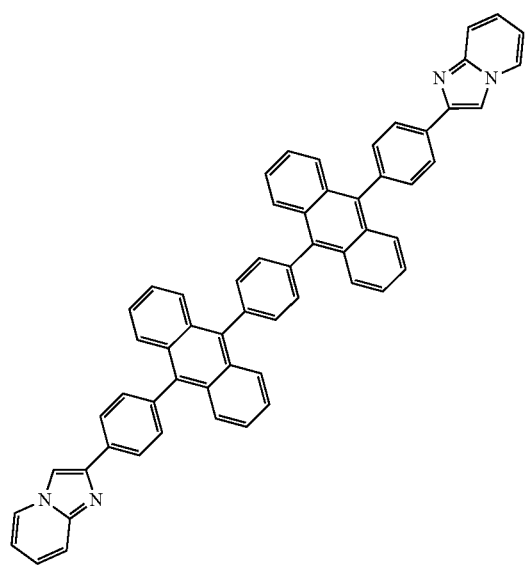
ETL1-54
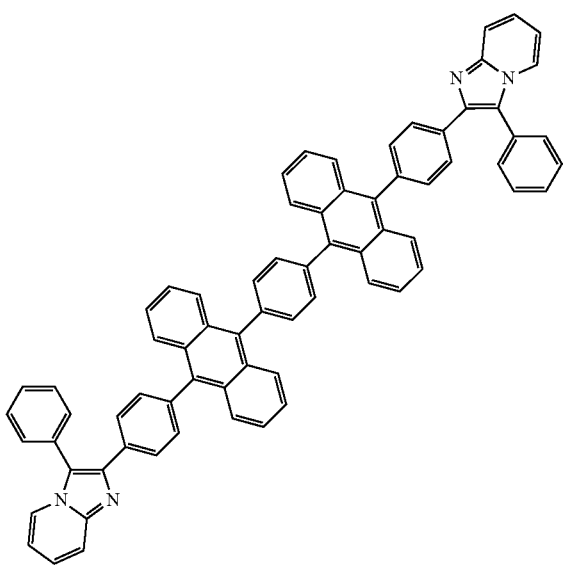

-continued

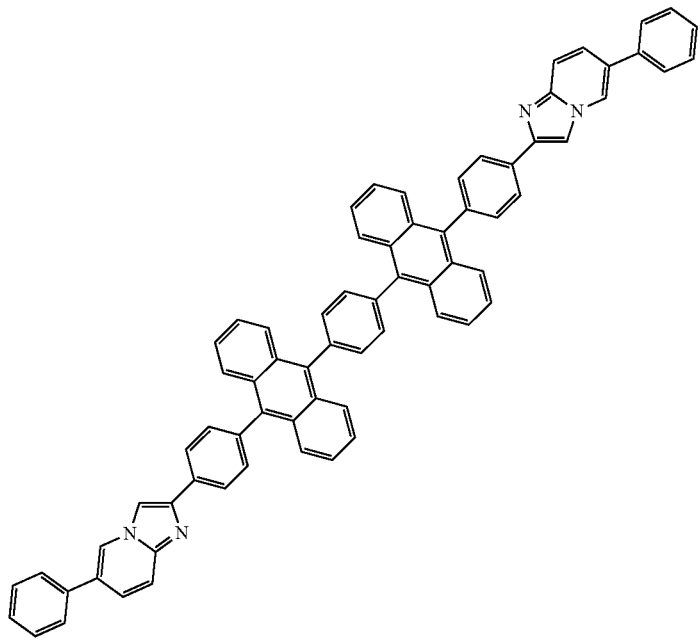

ETL1-55

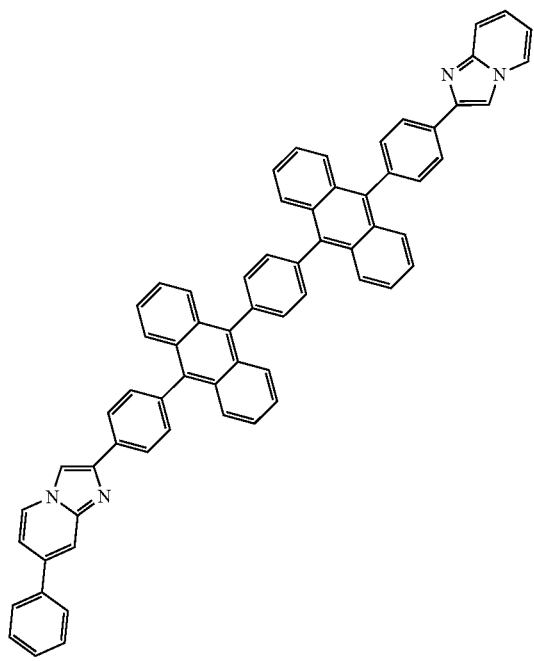

ETL1-56

Incidentally, such an azaindolizine-based compound has an excellent electron transport property and an excellent electron injection property as described above, and the reason for this is considered to be as follows.

The entire molecule of the azaindolizine-based compound having an azaindolizine skeleton and an anthracene skeleton in the molecule as described above is connected by a Π-conjugated system, and therefore, the electron cloud is spread across the entire molecule.

Then, the portion of the azaindolizine skeleton of the azaindolizine-based compound has a function to receive an electron and a function to send the received electron to the portion of the anthracene skeleton. On the other hand, the portion of the anthracene skeleton of the azaindolizine-based compound has a function to receive an electron from the portion of the azaindolizine skeleton and a function to transfer the received electron to a layer adjacent to the first electron transport layer 6b on the anode 3 side, that is, to the second electron transport layer 6a.

To be more specific, the portion of the azaindolizine skeleton of the azaindolizine-based compound includes two nitrogen atoms, and one of the nitrogen atoms (on the side near the portion of the anthracene skeleton) has an $sp^2$ hybrid orbital, and the other nitrogen atom (on the side far from the portion of the anthracene skeleton) has an $sp^3$ hybrid orbital. The nitrogen atom with an $sp^2$ hybrid orbital forms a portion of the conjugated system of the azaindolizine-based compound molecule and also has higher electronegativity than a carbon atom, and thus more strongly attracts an electron, and therefore functions as a portion that receives an electron. On the other hand, the nitrogen atom with an $sp^3$ hybrid orbital is not a normal conjugated system but has a non-covalent electron pair, and therefore, the electron of the nitrogen atom functions as a portion that sends an electron toward the conjugated system of the azaindolizine-based compound molecule.

On the other hand, the portion of the anthracene skeleton of the azaindolizine-based compound is electrically neutral, and therefore can easily receive an electron from the portion of the azaindolizine skeleton. Further, the portion of the anthracene skeleton of the azaindolizine-based compound has a large orbital overlap with the second anthracene-based compound which is the constituent material of the second electron transport layer 6a, and therefore can easily transfer an electron to the second anthracene-based material.

Further, such an azaindolizine-based compound has excellent electron transport property and electron injection property as described above, and therefore, as a result, the driving voltage of the light-emitting element 1 can be decreased.

Further, the portion of the azaindolizine skeleton is stable even if the nitrogen atom with an $sp^2$ hybrid orbital is reduced and also is stable even if the nitrogen atom with an $sp^3$ hybrid orbital is oxidized. Due to this, such an azaindolizine-based compound has high stability against electrons and holes. As a result, the life of the light-emitting element 1 can be extended.

<Second Electron Transport Layer>

The second electron transport layer 6a contains a second anthracene-based compound, which has an anthracene skeleton but does not have a heterocyclic skeleton. In other words, the second electron transport layer 6a contains a second anthracene-based compound, which has an anthracene skeleton in the molecule and is constituted by a carbon atom and a hydrogen atom.

The compound having an anthracene skeleton is a compound having an excellent electron transport property. Further, by using the second anthracene-based compound which does not have a heterocyclic skeleton, the second electron transport layer shows relatively strong resistance to oxidation and reduction due to transfer of holes, and therefore alteration or deterioration due to holes can be suppressed.

Here, the light-emitting material included in the light-emitting layer 5 is a material with a small band gap, and therefore, the difference in the HOMO and LUMO levels between the light-emitting material and the host material is increased. In particular, it is considered that when a thiadiazole-based compound or a benzo-bis-thiadiazole-based compound having a skeleton with a strong electron-withdrawing property is used as the light-emitting material, an electron is easily trapped in the light-emitting material in the light-emitting layer because of the energy level, and the electron transfer is limited, and therefore, carriers which move in the light-emitting layer 5 are mostly holes. As a result, the number of holes penetrating from the light-emitting layer 5 to the electron transport layer 6 tends to increase.

Due to this, for example, when a compound having a nitrogen-containing heterocyclic skeleton is used in the electron transport layer provided in contact with the light-emitting layer 5, since this compound has low durability against holes, deterioration is caused due to holes penetrating from the light-emitting layer 5, and as a result, a problem that the life of the light-emitting element is shortened occurs.

On the other hand, in the invention, the second electron transport layer 6a provided in contact with the light-emitting layer 5 contains a second anthracene-based compound, which has an anthracene skeleton but does not have a heterocyclic skeleton, and therefore, the alteration or deterioration of the second electron transport layer 6a due to holes penetrating from the light-emitting layer 5 can be suppressed or prevented.

Then, this second electron transport layer 6a functions as a block layer that prevents holes from reaching the first electron transport layer 6b, and therefore, the alteration or deterioration of the first electron transport layer 6b containing the first anthracene-based compound, which has a nitrogen-containing heterocyclic skeleton, due to holes can be suppressed or prevented.

Incidentally, the average thickness of the second electron transport layer 6a slightly varies also depending on the type of the light-emitting material contained in the light-emitting layer 5, but is preferably 25 nm or more and 200 nm or less, more preferably 50 nm or more and 150 nm or less. According to this, the second electron transport layer 6a can be made to favorably exhibit a function as the block layer that prevents holes from reaching the first electron transport layer 6b.

Further, the second anthracene-based compound may be any as long as it is a compound represented by the following formula ETL2, but is preferably a compound represented by the following formula ETL2-A, the following formula ETL2-B, the following formula ETL2-C, or the following formula ETL2-D, and more specifically, it is preferably, for example, a compound represented by any of the following formulae ETL2-1 to ETL2-56.

[Chem. 20]

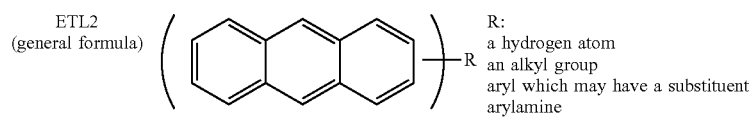

ETL2 (general formula)

R:
a hydrogen atom
an alkyl group
aryl which may have a substituent
arylamine

-continued

[Chem. 20]

| | | |
|---|---|---|
| ETL2-A | 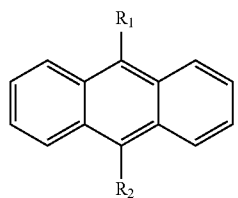 | $R_1$ and $R_2$ may be the same or different;<br>a hydrogen atom<br>an alkyl group<br>aryl which may have a substituent<br>arylamine |
| ETL2-B | 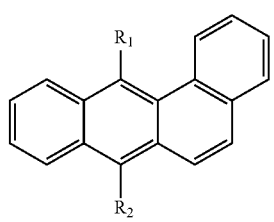 | $R_1$ and $R_2$ may be the same or different;<br>a hydrogen atom<br>an alkyl group<br>aryl which may have a substituent<br>arylamine |
| ETL2-C | 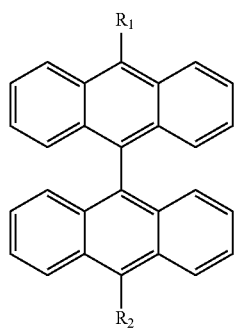 | $R_1$ and $R_2$ may be the same or different;<br>a hydrogen atom<br>an alkyl group<br>aryl which may have a substituent<br>arylamine |
| ETL2-D | 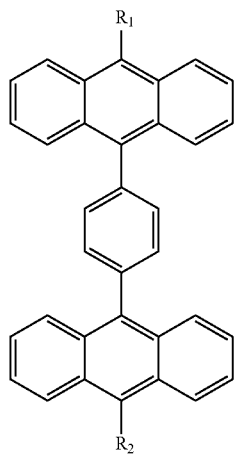 | $R_1$ and $R_2$ may be the same or different;<br>a hydrogen atom<br>an alkyl group<br>aryl which may have a substituent<br>arylamine |

[Chem. 21]
ETL2-1
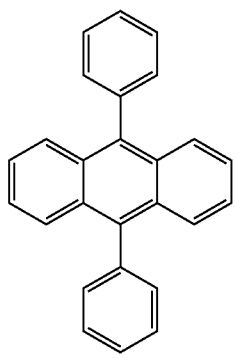
ETL2-2
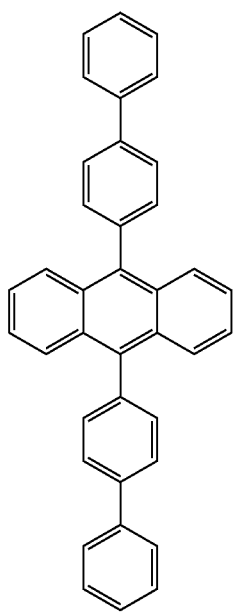
ETL2-3
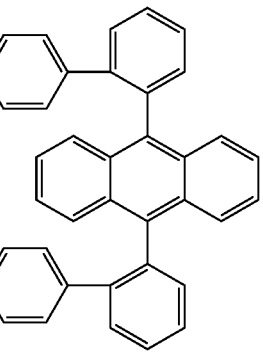
ETL2-4
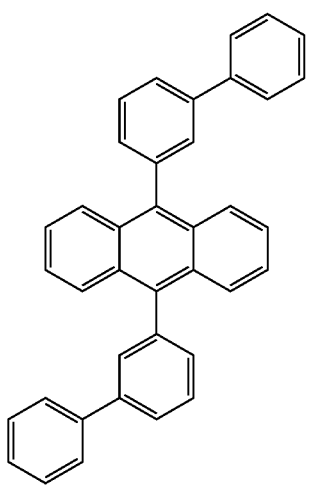
ETL2-5
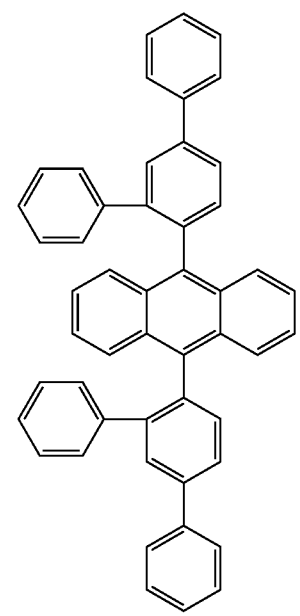
ETL2-6
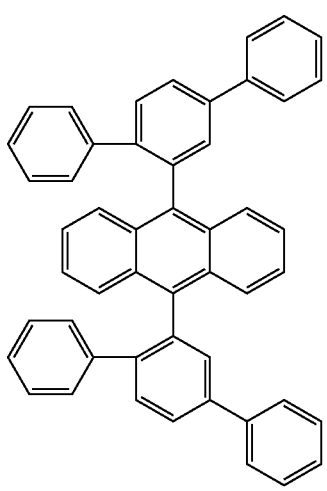

ETL2-7
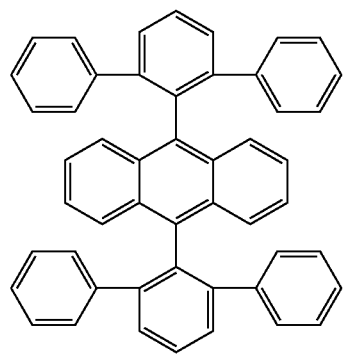
ETL2-8
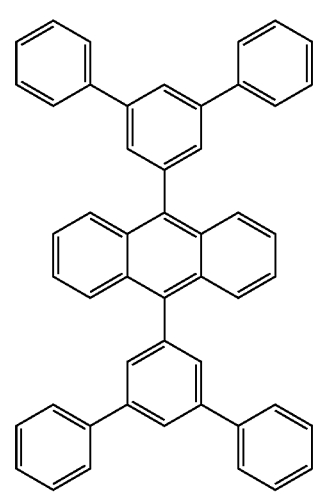
ETL2-9
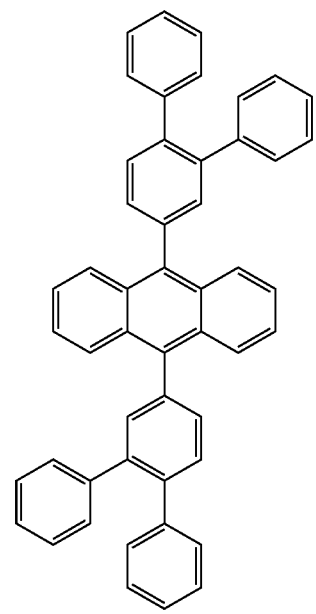
ETL2-10
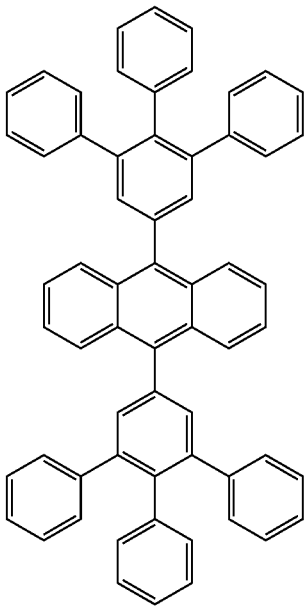
ETL2-11
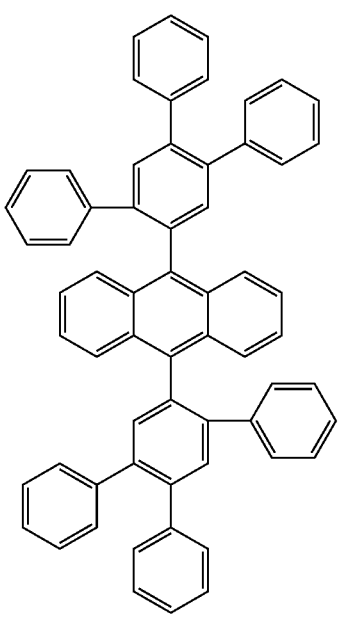
ETL2-12
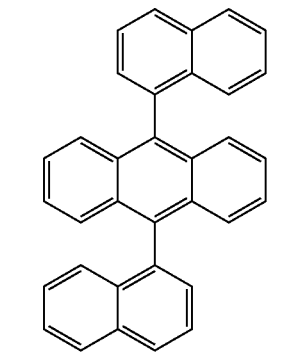

ETL2-713
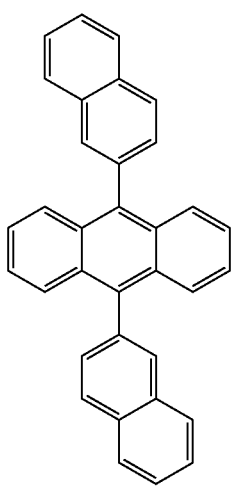
ETL2-14
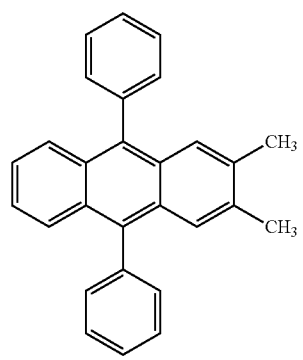
ETL2-15
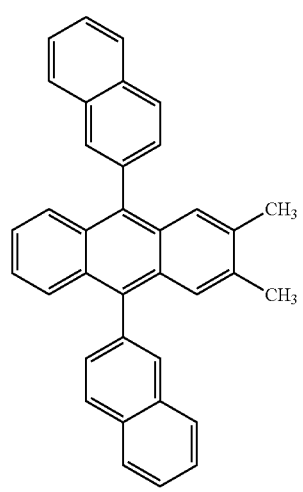
[Chem. 22]
ETL2-16
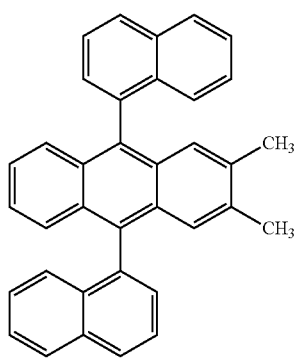
ETL2-17
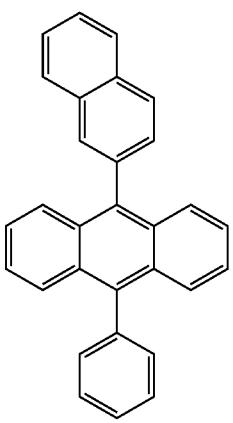
ETL2-18
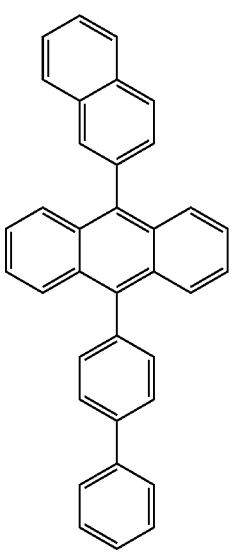

ETL2-19
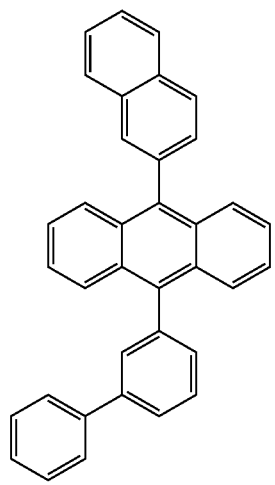
ETL2-20
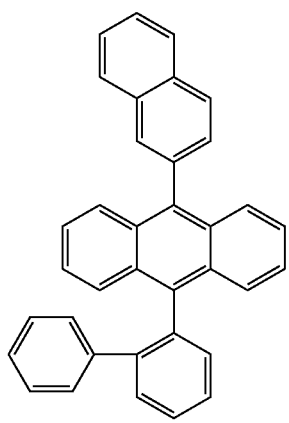
ETL2-21
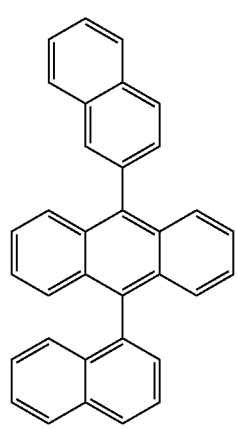
ETL2-22
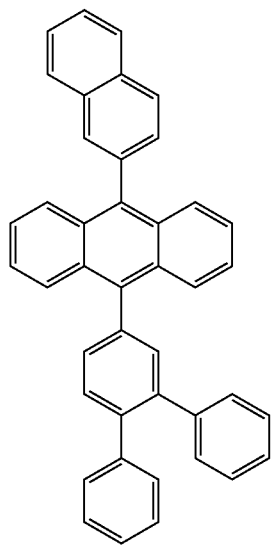
ETL2-23
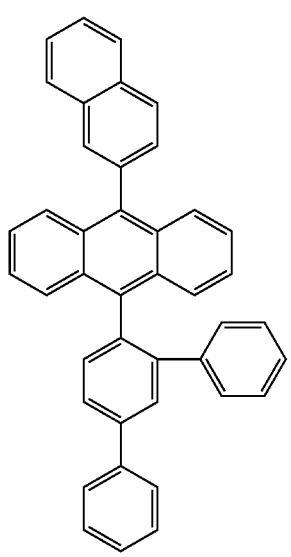
ETL2-24
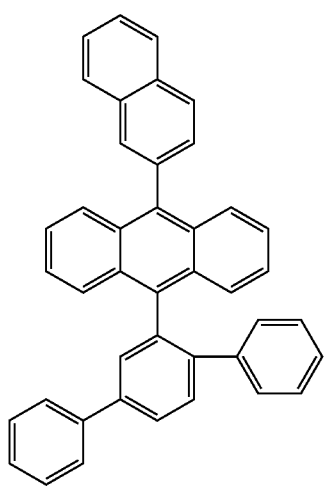

ETL2-25
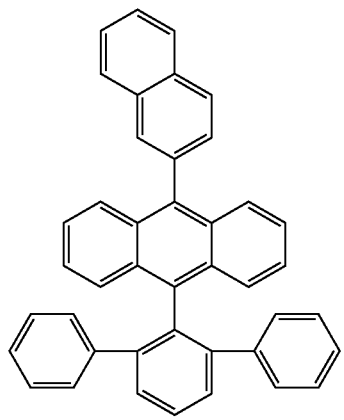
ETL2-26
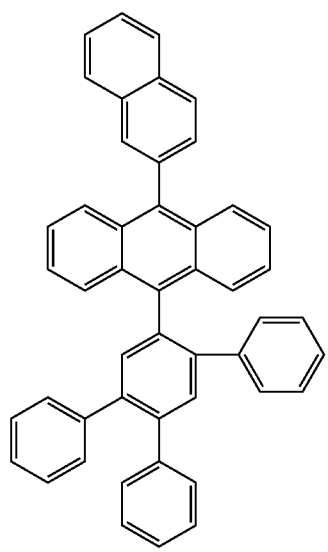
ETL2-27
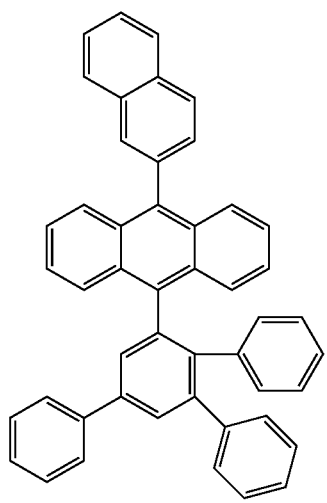
ETL2-28
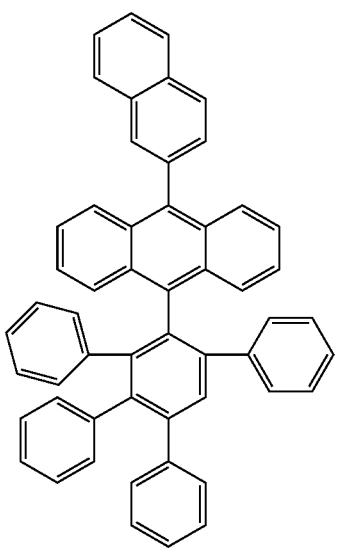
ETL2-29
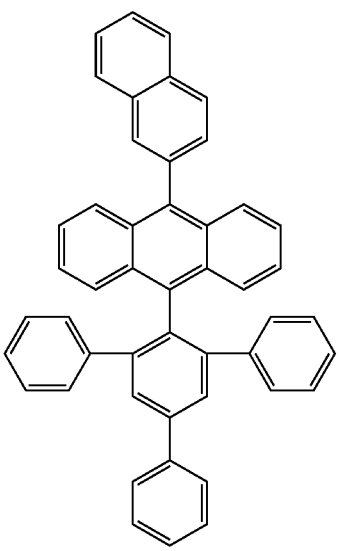

ETL2-30
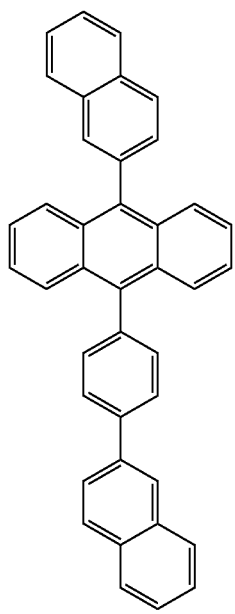
ETL2-31
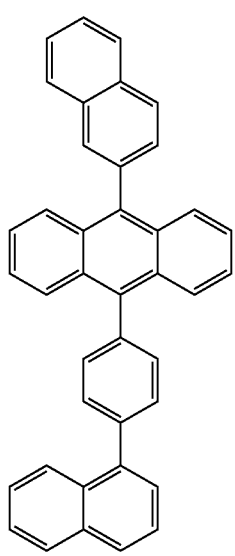
ETL2-32
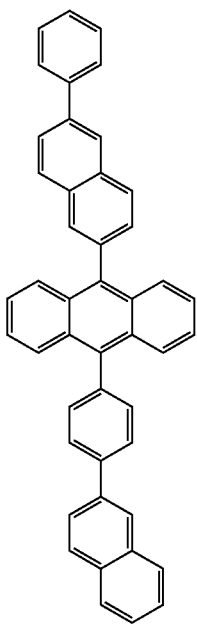
ETL2-33
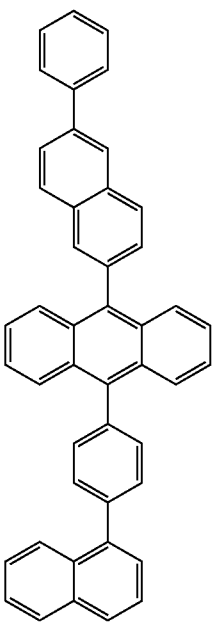

ETL2-34
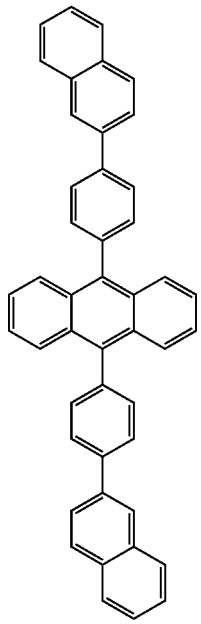
ETL2-36
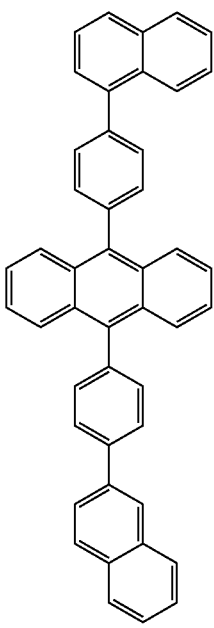
[Chem. 23]
ETL2-37
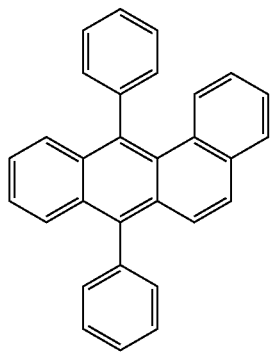
ETL2-35
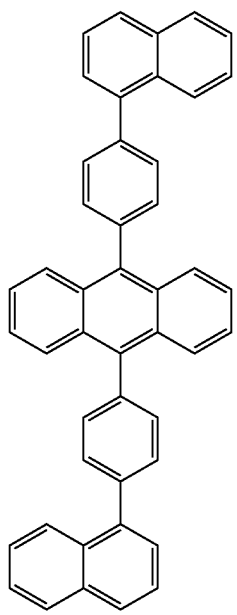
ETL2-38
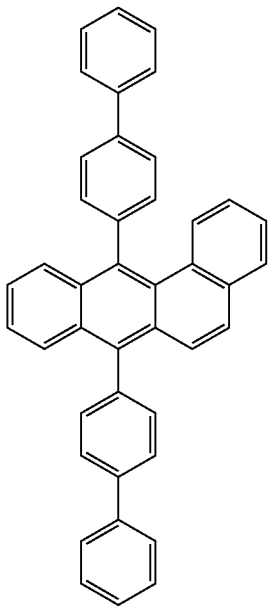

ETL2-39
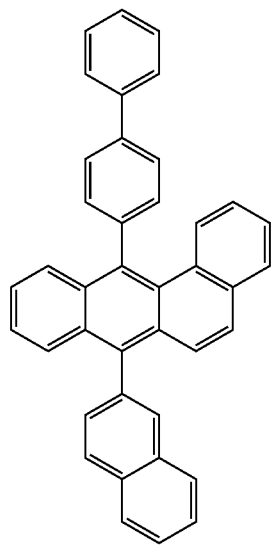
ETL2-40
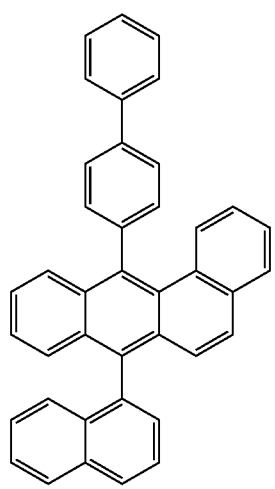
ETL2-41
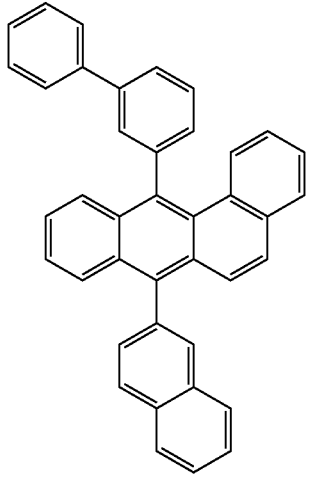
ETL2-42
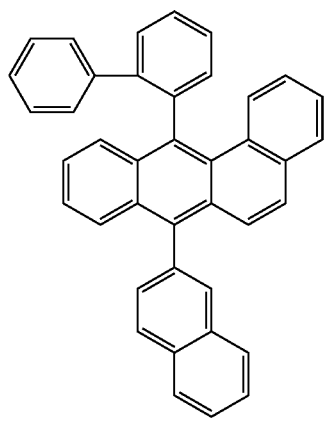
ETL2-43
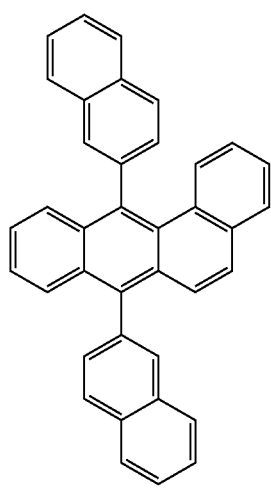
ETL2-44
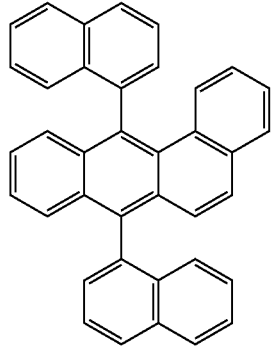

ETL2-45
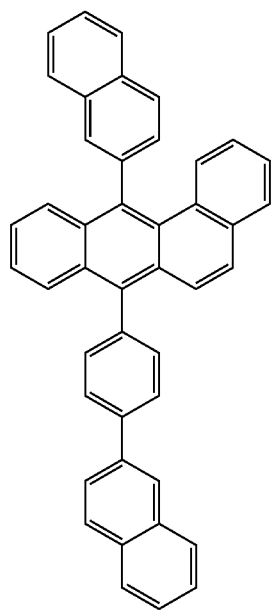
ETL2-46
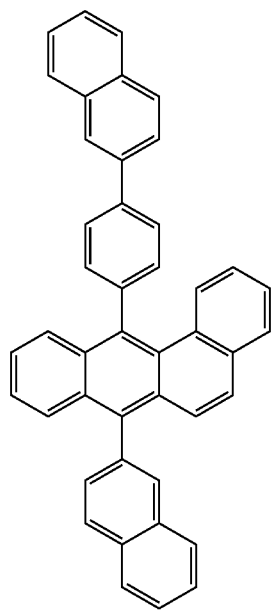
ETL2-47
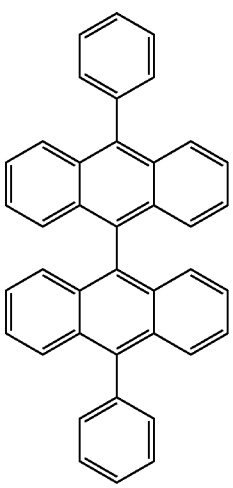
ETL2-48
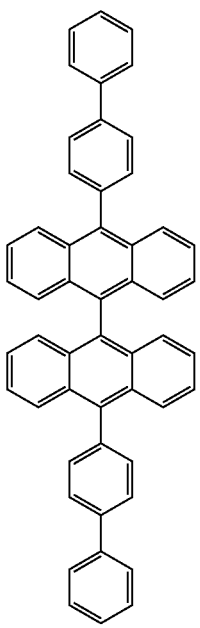

ETL2-49
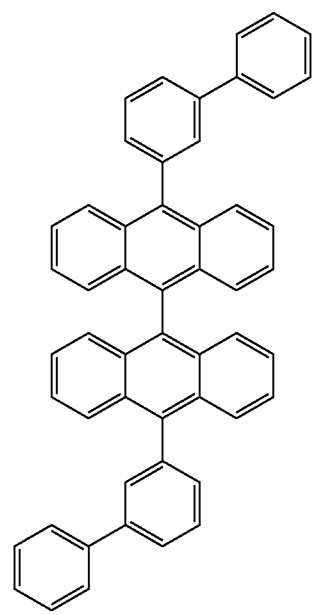
ETL2-51
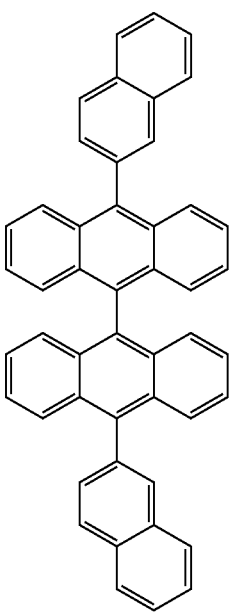
ETL2-50
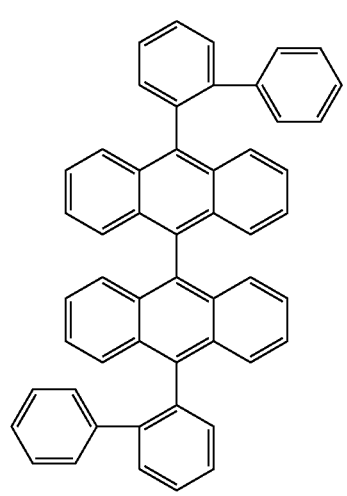
ETL2-52
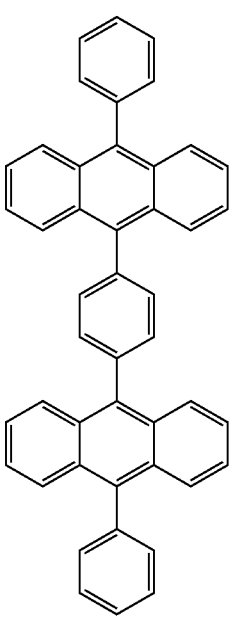

ETL2-53

ETL2-54

ETL2-55

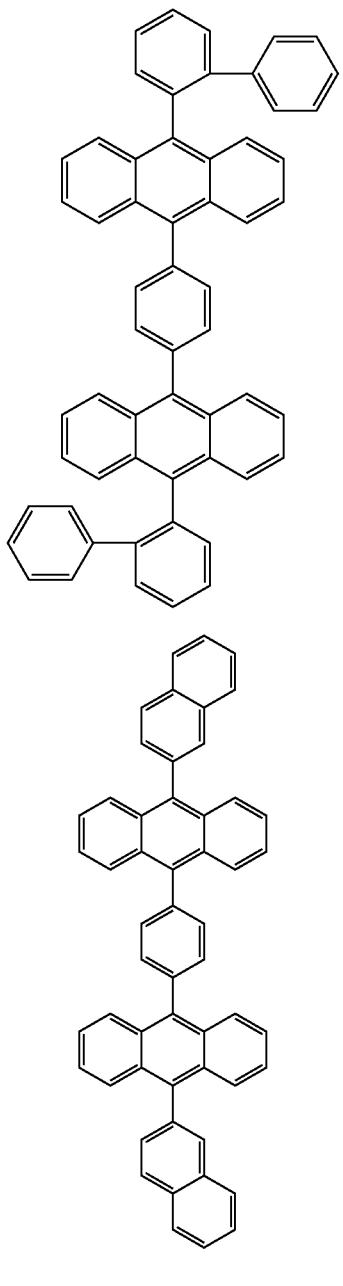

ETL2-56

Further, a difference between the HOMO of the constituent material (the second anthracene-based material) of the second electron transport layer 6a and the HOMO of the host material to be used in the light-emitting layer 5 is preferably 0.2 eV or more. According to this, holes coming out of the light-emitting layer 5 to the electron transport layer 6 are reduced, and thus, the luminous efficiency can be increased.

Further, a difference between the HOMO of the constituent material (the second anthracene-based material) of the second electron transport layer 6a and the HOMO of the constituent material (the first anthracene-based material) of the first electron transport layer 6b is preferably 0.2 eV or more, and also a difference between the LUMO of the constituent material (the second anthracene-based material) of the second electron transport layer 6a and the LUMO of the constituent material (the first anthracene-based material)

of the first electron transport layer 6b is preferably 0.2 eV or more. According to this, while reducing holes coming out of the second electron transport layer 6a to the first electron transport layer 6b, electrons can be smoothly transported from the first electron transport layer 6b to the second electron transport layer 6a, and therefore, the efficiency of the light-emitting element 1 is increased.

Also, it is preferred that the electron mobility of the constituent material (the second anthracene-based material) of the second electron transport layer 6a is larger than the electron mobility of the constituent material (the first anthracene-based material) of the first electron transport layer 6b. According to this, electrons can be smoothly transported from the first electron transport layer 6b to the second electron transport layer 6a.

Further, the HOMO of the constituent material (the second anthracene-based compound) of the second electron transport layer 6a is preferably 5.5 eV or more and 6.0 eV or less, and the LUMO of the constituent material of the second electron transport layer 6a is preferably 2.5 eV or more and 3.0 eV or less.

In addition, the HOMO of the constituent material (the first anthracene-based compound) of the first electron transport layer 6b is preferably 5.8 eV or more and 6.5 eV or less, and the LUMO of the constituent material of the first electron transport layer 6b is preferably 2.8 eV or more and 3.5 eV or less.

Further, it is preferred that the first anthracene-based compound and the second anthracene-based compound each have a glass transition temperature (Tg) of 125° C. or higher. According to this, even if the light-emitting element 1 is used by applying a current between the anode 3 and the cathode 8 at a current density of about 500 A/cm$^2$ or more and 1000 A/cm$^2$ or less, fluidization of the electron transport layer 6 (the first electron transport layer 6b and the second electron transport layer 6a) can be suppressed or prevented, and therefore, the decrease in the luminous efficiency of the light-emitting element 1 due to this is suppressed or prevented.

(Electron Injection Layer)

The electron injection layer 7 has a function to improve the efficiency of electron injection from the cathode 8.

Examples of the constituent material (electron-injecting material) of the electron injection layer 7 include various types of inorganic insulating materials and various types of inorganic semiconductor materials.

Examples of such an inorganic insulating material include alkali metal chalcogenides (oxides, sulfides, selenides, and tellurides), alkaline earth metal chalcogenides, alkali metal halides, and alkaline earth metal halides, and among these, it is possible to use one type or two or more types in combination. By constituting the electron injection layer 7 by such a material as a main material, the electron injection property can be further improved. In particular, an alkali metal compound (such as an alkali metal chalcogenide or an alkali metal halide) has a very small work function, and by constituting the electron injection layer 7 by using the compound, the light-emitting element 1 can have high luminance.

Examples of the alkali metal chalcogenide include $Li_2O$, LiO, $Na_2S$, $Na_2Se$, and NaO.

Examples of the alkaline earth metal chalcogenide include CaO, BaO, SrO, BeO, BaS, MgO, and CaSe.

Examples of the alkali metal halide include CsF, LiF, NaF, KF, LiCl, KCl, and NaCl.

Examples of the alkaline earth metal halide include $CaF_2$, $BaF_2$, $SrF_2$, $MgF_2$, and $BeF_2$.

Further, examples of the inorganic semiconductor material include oxides, nitrides, and oxynitrides containing at least one element selected from Li, Na, Ba, Ca, Sr, Yb, Al, Ga, In, Cd, Mg, Si, Ta, Sb, and Zn, and among these, it is possible to use one type or two or more types in combination.

The average thickness of the electron injection layer 7 is not particularly limited, but is preferably from about 0.1 to 1000 nm, more preferably from about 0.2 to 100 nm, further more preferably from about 0.2 to 50 nm.

Incidentally, the electron injection layer 7 may be omitted depending on the constituent material, thickness, or the like of the cathode 8 and the electron transport layer 6.

(Sealing Member)

The sealing member 9 is provided so as to cover the anode 3, the stacked body 14, and the cathode 8, and has a function to hermetically seal these members and block oxygen and moisture. By providing the sealing member 9, an effect of improvement of the reliability of the light-emitting element 1, prevention of the alteration or deterioration (improvement of the durability) of the light-emitting element 1, or the like is obtained.

Examples of the constituent material of the sealing member 9 include Al, Au, Cr, Nb, Ta, Ti, an alloy containing any of these metals, silicon oxide, and various types of resin materials. Incidentally, in the case where a material having electrical conductivity is used as the constituent material of the sealing member 9, in order to prevent a short circuit, it is preferred to provide an insulating film as needed between the sealing member 9 and each of the anode 3, the stacked body 14, and the cathode 8.

Further, the sealing member 9 may be formed into a flat plate shape and made to face the substrate 2, and a space therebetween may be sealed with, for example, a sealant such as a thermosetting resin.

According to the light-emitting element 1 configured as described above, a benzo-bis-thiadiazole-based compound is used as the light-emitting material of the light-emitting layer 5, and also a tetracene-based material is used as the host material of the light-emitting layer 5, and therefore, light emission in a near-infrared range can be achieved, and also the efficiency and life thereof can be increased.

The light-emitting element 1 as described above can be produced, for example, as follows.

[1] First, a substrate 2 is prepared and an anode 3 is formed on the substrate 2.

The anode 3 can be formed by using, for example, a dry plating method such as a chemical vapor deposition (CVD) method such as plasma CVD or thermal CVD, or vacuum vapor deposition, a wet plating method such as electroplating, a thermal spraying method, a sol-gel method, an MOD method, metal foil joining, or the like.

[2] Subsequently, a hole injection layer 4 is formed on the anode 3.

The hole injection layer 4 is preferably formed by, for example, a gas phase process using a dry plating method such as a CVD method, vacuum vapor deposition, or sputtering, or the like.

Incidentally, the hole injection layer 4 can also be formed by, for example, supplying a hole injection layer-forming material prepared by dissolving a hole-injecting material in a solvent or dispersing a hole-injecting material in a dispersion medium onto the anode 3, followed by drying (removal of the solvent or removal of the dispersion medium).

As the method for supplying the hole injection layer-forming material, for example, any of various coating methods such as a spin coating method, a roll coating method, and an ink jet printing method can also be used. The hole injection layer 4 can be relatively easily formed by using such a coating method.

Examples of the solvent or the dispersion medium to be used in the preparation of the hole injection layer-forming material include various types of inorganic solvents, various types of organic solvents, and mixed solvents containing any of these solvents.

Incidentally, the drying can be performed by, for example, leaving the material to stand in an atmosphere at atmospheric pressure or reduced pressure, by a heating treatment, by spraying an inert gas, or the like.

Further, prior to this step, the upper surface of the anode 3 may be subjected to an oxygen plasma treatment. By doing this, lyophilicity can be imparted to the upper surface of the anode 3, an organic substance adhered to the upper surface of the anode 3 can be removed (washed off), the work function in the vicinity of the upper surface of the anode 3 can be adjusted, and so on.

Here, the conditions for the oxygen plasma treatment are preferably, for example, as follows: the plasma power is from about 100 to 800 W, the oxygen gas flow rate is from about 50 to 100 mL/min, the speed of conveying a member to be treated (anode 3) is from about 0.5 to 10 mm/sec, and the temperature of the substrate 2 is from about 70 to 90° C.

[3] Subsequently, a light-emitting layer 5 is formed on the hole injection layer 4.

The light-emitting layer 5 can be formed by, for example, a gas phase process using a dry plating method such as vacuum vapor deposition, or the like.

[4] Subsequently, an electron transport layer 6 (a first electron transport layer 6b and a second electron transport layer 6a) is formed on the light-emitting layer 5.

It is preferred that the electron transport layer 6 (the first electron transport layer 6b and the second electron transport layer 6a) is formed by, for example, a gas phase process using a dry plating method such as vacuum vapor deposition, or the like.

Incidentally, the electron transport layer 6 can also be formed by, for example, supplying an electron transport layer-forming material prepared by dissolving an electron-transporting material in a solvent or dispersing an electron-transporting material in a dispersion medium onto the light-emitting layer 5, followed by drying (removal of the solvent or removal of the dispersion medium).

[5] Subsequently, an electron injection layer 7 is formed on the electron transport layer 6.

In the case where an inorganic material is used as the constituent material of the electron injection layer 7, the electron injection layer 7 can be formed by using, for example, a gas phase process using a dry plating method such as a CVD method, vacuum vapor deposition, or sputtering, or the like, coating and firing of an inorganic fine particle ink, or the like.

[6] Subsequently, a cathode 8 is formed on the electron injection layer 7.

The cathode 8 can be formed by using, for example, a vacuum vapor deposition method, a sputtering method, metal foil joining, coating and firing of a metal fine particle ink, or the like.

The light-emitting element 1 is obtained through the steps as described above.

Finally, a sealing member 9 is placed thereon so as to cover the obtained light-emitting element 1 and joined to the substrate 2.

(Light-Emitting Device)

Next, an embodiment of the light-emitting device of the invention will be described.

Figure 2:
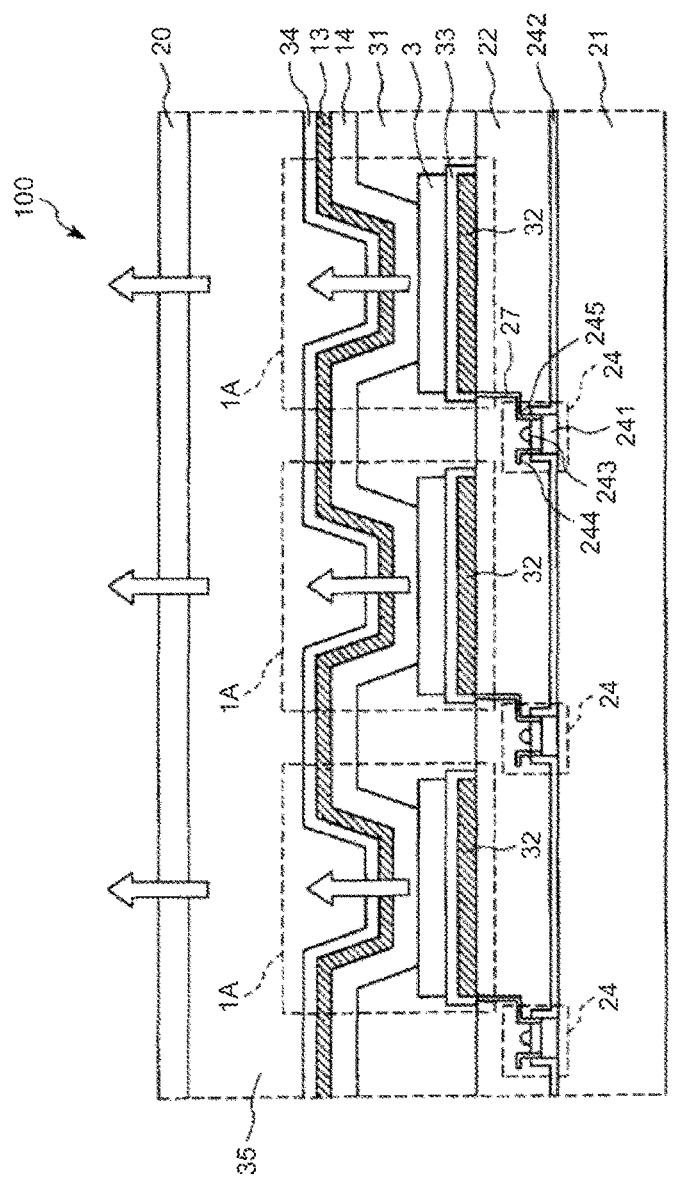
FIG. 2 is a longitudinal cross-sectional view showing an embodiment of a display device to which a light-emitting device of the invention is applied.

FIG. 2 is a longitudinal cross-sectional view showing an embodiment of a display device to which the light-emitting device of the invention is applied.

A display device 100 shown in FIG. 2 includes a substrate 21, a plurality of light-emitting elements 1A, and a plurality of driving transistors 24 for driving the respective light-emitting elements 1A. Here, the display device 100 is a display panel having a top emission structure.

On the substrate 21, the plurality of driving transistors 24 are provided, and a planarization layer 22 constituted by an insulating material is formed so as to cover these driving transistors 24.

Each driving transistor 24 includes a semiconductor layer 241 composed of silicon, a gate insulating layer 242 formed on the semiconductor layer 241, a gate electrode 243 formed on the gate insulating layer 242, a source electrode 244, and a drain electrode 245.

On the planarization layer, the light-emitting elements 1A are provided corresponding to the respective driving transistors 24.

In the light-emitting element 1A, on the planarization layer 22, a reflective film 32, an anticorrosive film 33, an anode 3, a stacked body (an organic EL light-emitting section) 14, a cathode 13, and a cathode cover 34 are stacked in this order. In this embodiment, the anode 3 of each light-emitting element 1A constitutes a pixel electrode and is electrically connected to the drain electrode 245 of each driving transistor 24 through an electrically conductive section (wiring) 27. Further, the cathode 13 of each light-emitting element 1A acts as a common electrode.

The light-emitting element 1A in FIG. 2 emits light in a near-infrared range, and the light-emitting element 1 of the invention described above is applied.

Between the adjacent light-emitting elements 1A, a partition wall 31 is provided. Further, on the light-emitting elements 1A, an epoxy layer 35 constituted by an epoxy resin is formed so as to cover the light-emitting elements 1A.

Then, on the epoxy layer 35, a sealing substrate 20 is provided so as to cover the epoxy layer 35.

The display device 100 as described above can be used as, for example, a near-infrared display for military purposes or the like.

According to such a display device 100, light in a near-infrared range can be emitted. Further, since the display device 100 includes the light-emitting element 1A with high efficiency and long life, and therefore has excellent reliability.

(Authentication Device)

Next, an embodiment of the authentication device of the invention will be described.

Figure 3:
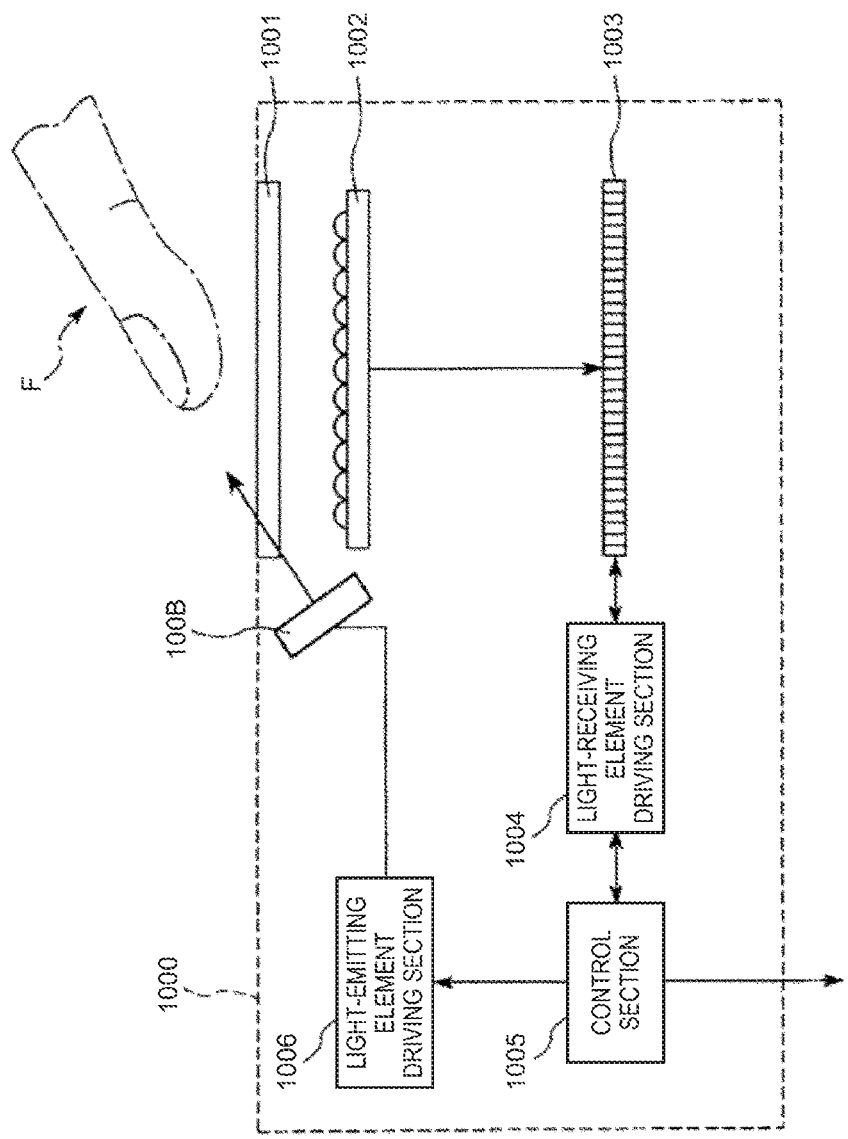
FIG. 3 is a view showing an embodiment of an authentication device of the invention.

FIG. 3 is a view showing an embodiment of the authentication device of the invention.

An authentication device 1000 shown in FIG. 3 is a biometric authentication device which authenticates an individual using the biological information of a living body F (in this embodiment, a fingertip).

The authentication device 1000 includes a light source 100B, a cover glass 1001, a microlens array 1002, a light-receiving element group 1003, a light-emitting element driving section 1006, a light-receiving element driving section 1004, and a control section 1005.

The light source 100B includes a plurality of light-emitting elements 1 described above, and irradiates light in a near-infrared range onto the living body F which is the objet to be imaged. For example, the light-emitting elements 1 of the light source 100B are arranged along the outer circumference of the cover glass 1001.

The light-emitting element to be used in the light source 100B is generally used by applying a current at a current density of about 500 A/cm$^2$ or more and 1000 A/cm$^2$ or less, and the light-emitting element 1 of the invention with increased efficiency and extended life is favorably used as such a light-emitting element.

The cover glass 1001 is a part which the living body F comes into contact with or comes close to.

The microlens array 1002 is provided on the side opposite to the side of the cover glass 1001 which the living body F comes into contact with or comes close to. This microlens array 1002 is constituted by a plurality of microlenses arranged in a matrix.

The light-receiving element group 1003 is provided on the side opposite to the cover glass 1001 with respect to the microlens array 1002. The light-receiving element group 1003 is constituted by a plurality of light-receiving elements provided in a matrix corresponding to the plurality of microlenses of the microlens array 1002. As each light-receiving element of the light-receiving element group 1003, for example, a CCD (Charge Coupled Device), a CMOS, or the like can be used.

The light-emitting element driving section 1006 is a driving circuit which drives the light source 100B.

The light-receiving element driving section 1004 is a driving circuit which drives the light-receiving element group 1003.

The control section 1005 is, for example, an MPU, and has a function to control the driving of the light-emitting element driving section 1006 and the light-receiving element driving section 1004.

Further, the control section 1005 has a function to perform authentication of the living body F by comparison between the light reception result of the light-receiving element group 1003 and the previously stored biometric authentication information.

For example, the control section 1005 forms an image pattern (for example, a vein pattern) associated with the living body F based on the light reception result of the light-receiving element group 1003. Then, the control section 1005 compares the formed image pattern and the image pattern previously stored as the biometric authentication information, and performs authentication (for example, vein authentication) of the living body F based on the comparison result.

According to such an authentication device 1000, biometric authentication can be performed using near-infrared light. Further, the authentication device 1000 includes the light-emitting element 1 with high efficiency and long life, and therefore has excellent reliability.

Such an authentication device 1000 can be incorporated into various types of electronic apparatuses.

(Electronic Apparatus)

Figure 4:
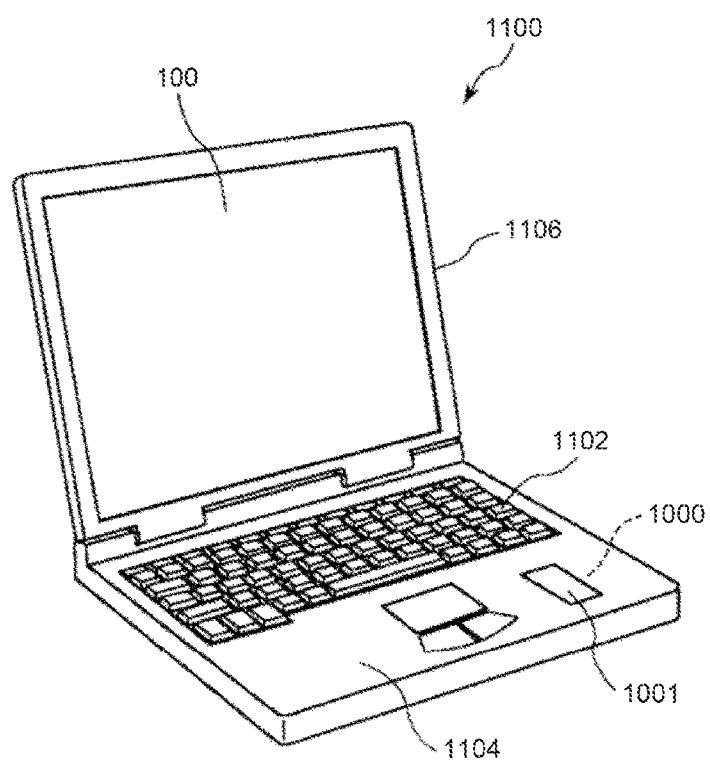
FIG. 4 is a perspective view showing the configuration of a mobile-type (or notebook-type) personal computer to which an electronic apparatus of the invention is applied.

FIG. 4 is a perspective view showing the configuration of a mobile-type (or notebook-type) personal computer to which an electronic apparatus of the invention is applied.

In this drawing, a personal computer 1100 is configured to include a main body 1104 provided with a keyboard 1102 and a display unit 1106 provided with a display section, and the display unit 1106 is supported rotatably with respect to the main body 1104 through a hinge structure.

In the personal computer 1100, the main body 1104 is provided with the above-mentioned authentication device 1000.

According to such a personal computer 1100, the light-emitting element 1 which has high efficiency and long life is included, and therefore, it has excellent reliability.

Incidentally, the electronic apparatus of the invention can not only be applied to the personal computer (mobile-type personal computer) shown in FIG. 4, but also be applied to, for example, a mobile phone, a digital still camera, a television, a video camera, a view finder-type or monitor direct view-type video tape recorder, a laptop-type personal computer, a car navigation device, a pager, an electronic organizer (including an electronic organizer with a communication function), an electronic dictionary, an electronic calculator, an electronic gaming machine, a word processor, a workstation, a videophone, a security television monitor, electronic binoculars, a POS terminal, an apparatus provided with a touch panel (for example, a cash dispenser in financial institutions and an automatic ticket vending machine), a medical apparatus (for example, an electronic thermometer, a sphygmomanometer, a blood glucose meter, a sphygmometer, a plethysmograph, an electrocardiographic device, an ultrasonic diagnostic device, or a display device for an endoscope), a fish finder, various types of measurement apparatuses, meters and gauges (for example, meters and gauges for vehicles, aircrafts, and ships), a flight simulator, other various types of monitors, a projection-type display device such as a projector, and the like.

Hereinabove, the light-emitting element, the light-emitting device, the authentication device, and the electronic apparatus of the invention have been described with reference to the embodiments shown in the drawings, however, the invention is not limited thereto.

For example, the light-emitting element and the light-emitting device of the invention each may be used as a light source for lighting.

EXAMPLES

Next, specific examples of the invention will be described.

1. Production of Light-Emitting Material (Production of IRD1-2)

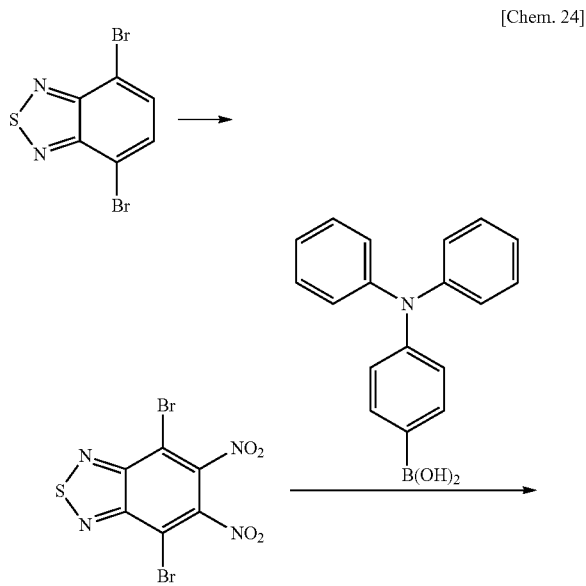

[Chem. 24]

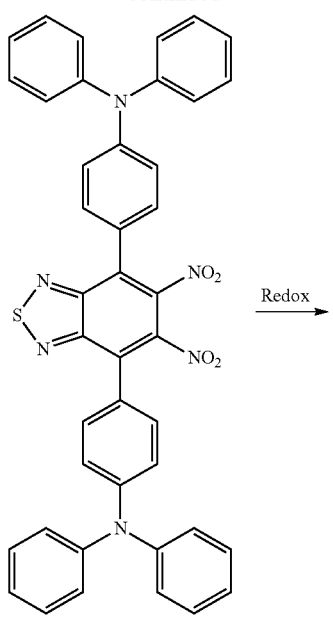

Redox →

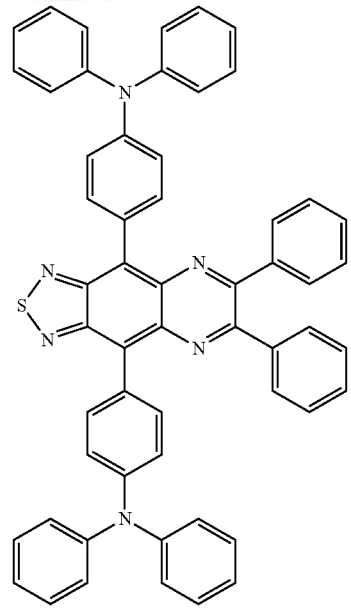 [SMILES: c1ccc(-c2nc3c(-c4ccc(N(c5ccccc5)c5ccccc5)cc4)c4nsnc4c(-c4ccc(N(c5ccccc5)c5ccccc5)cc4)c3nc2-c2ccccc2)cc1]

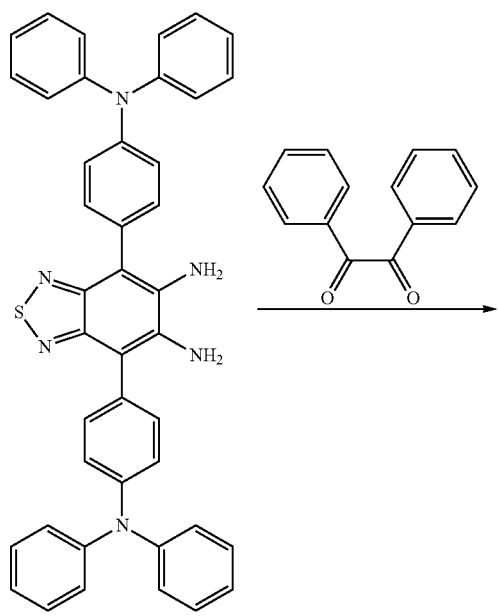

Synthesis (A1-1)

In a 5-L flask, 1500 mL of fuming nitric acid was placed and cooled. Thereto, 1500 mL of sulfuric acid was added in divided portions such that the temperature was maintained at 10 to 50° C. Further, 150 g of a compound (a) which is dibromobenzothiadiazole as a starting material was added thereto in small portions over 1 hour. At this time, the temperature of the solution was maintained at 5° C. or lower. After the addition of the total amount, a reaction was allowed to proceed for 20 hours at room temperature (25° C.). After the reaction, the reaction mixture was poured into 3 kg of ice, followed by stirring overnight. Thereafter, the mixture was filtered, followed by washing with methanol and heptane.

The residue after filtration was thermally dissolved in 200 mL of toluene, and the resulting solution was gradually cooled to room temperature and then filtered. The resulting residue was washed with a small amount of toluene, and then dried under reduced pressure.

By doing this, 60 g of a compound (b) (4,7-dibromo-5,6-dinitro-benzo[1,2,5]thiadiazole) with an HPLC purity of 95% was obtained.

Synthesis (A1-2)

In an Ar atmosphere, in a 5-L flask, 30 g of the compound (b) which is the obtained dibromo compound, 160 g of a triphenylamine boronic acid compound, 2500 mL of toluene, and a 2 M aqueous solution of cesium carbonate (152 g/234 mL of distilled water) were placed, and a reaction was allowed to proceed overnight at 90° C. After the reaction, filtration, liquid separation, and concentration were performed, and 52 g of the resulting crude material was separated using a silica gel column (5 kg of $SiO_2$), whereby a red-purple solid was obtained.

By doing this, 6 g of a compound (c) (5,6-dinitro-4,7-diphenyl-benzo[1,2,5]thiadiazole) with an HPLC purity of 96% was obtained.

Synthesis (A1-3)

In an Ar atmosphere, in a 1-L flask, 6 g of the compound (c) which is the obtained dinitro compound, 7 g of reduced iron, and 600 mL of acetic acid were placed, and a reaction was allowed to proceed at 80° C. for 4 hours, and then the mixture was cooled to room temperature. After the reaction, the reaction mixture was poured into 1.5 L of ion exchanged water, and then, 1.5 L of ethyl acetate was further added thereto. After the addition, a solid was deposited, and therefore, 1 L of tetrahydrofuran and 300 g of sodium chloride were added thereto, and liquid separation was performed. The aqueous layer was reextracted with 1 L of tetrahydrofuran, followed by concentration and drying. The resulting residue was again washed with a small amount of water and methanol, whereby an orange solid was obtained.

By doing this, 7 g of a compound (d) (4,7-diphenyl-benzo[1,2,5]thiadiazolo-5,6-diamine) with an HPLC purity of 80% was obtained.

Synthesis (A1-4)

In an Ar atmosphere, in a 1-L flask, 4.5 g of the compound (d) which is the obtained diamine compound, 3.7 g of benzil, and 300 mL of acetic acid as a solvent were placed, and a reaction was allowed to proceed at 80° C. for 2 hours. After the reaction, the reaction mixture was cooled to room temperature, and then poured into 1 L of ion exchanged water. The resulting crystal was filtered and washed with water, whereby 7 g of a black-green solid was obtained. Then, this black-green solid was purified using a silica gel column (1 kg of $SiO_2$).

By doing this, 4 g of a compound (e) (a compound represented by the above formula IRD1-2) with an HPLC purity of 99% was obtained. This compound (e) was subjected to mass analysis, and the result was as follows: M+: 492.

Further, the obtained compound (e) was purified by sublimation at a set temperature of 340° C. The HPLC purity of the compound (e) after the purification by sublimation was 99%.

2. Production of Light-Emitting Element

Example 1

<1> First, a transparent glass substrate having an average thickness of 0.5 mm was prepared. Subsequently, on this substrate, an ITO electrode (anode) having an average thickness of 100 nm was formed by a sputtering method.

Then, the substrate was subjected to ultrasonic cleaning while immersing the substrate in acetone and 2-propanol in this order, and thereafter subjected to an oxygen plasma treatment and an argon plasma treatment. Each of these plasma treatments was performed while heating the substrate to 70 to 90° C. at a plasma power of 100 W and a gas flow rate of 20 sccm for a treatment time of 5 sec.

<2> Subsequently, a compound represented by the above formula HIL-1 was deposited on the ITO electrode by a vacuum vapor deposition method, whereby a hole injection layer having an average thickness of 30 nm was formed.

Incidentally, the Tg of the compound represented by the above formula HIL-1 was 133° C.

<3> Subsequently, the constituent material of a light-emitting layer was deposited on the hole injection layer by a vacuum vapor deposition method, whereby a light-emitting layer having an average thickness of 25 nm was formed. As the constituent material of the light-emitting layer, a compound (thiadiazole-based compound) represented by the above formula IRD1-2 was used as a light-emitting material (guest material), and a compound (tetracene-based material) represented by the above formula H-1 was used as a host material. Further, the content (doping concentration) of the light-emitting material (dopant) in the light-emitting layer was set to 2.0 wt %.

Incidentally, the Tg of the compound represented by the above formula H-1 was 154° C.

<4> Subsequently, a compound (anthracene-based compound) represented by the above ETL2-30 was deposited on the light-emitting layer by a vacuum vapor deposition method, whereby a second electron transport layer having an average thickness of 55 nm was formed.

Incidentally, the compound represented by ETL2-30 had a HOMO of 6.0 eV, a LUMO of 3.0 eV, and an electron mobility of $4.5 \times 10^{-5}$ $cm^2/V \cdot s$. Further, the Tg of the compound represented by the above formula ETL2-30 was 128° C.

<5> Subsequently, a compound (azaindolizine-based compound) represented by the above ETL1-3 was deposited on the second electron transport layer by a vacuum vapor deposition method, whereby a first electron transport layer having an average thickness of 5 nm was formed.

Incidentally, the compound represented by ETL1-3 had a HOMO of 5.9 eV, a LUMO of 2.9 eV, and an electron mobility of $1.5 \times 10^{-6}$ $cm^2/V \cdot s$. Further, the Tg of the compound represented by the above formula ETL1-3 was 128° C.

<6> Subsequently, lithium fluoride (LiF) was deposited on the first electron transport layer (electron transport layer) by a vacuum vapor deposition method, whereby an electron injection layer having an average thickness of 1 nm was formed.

<7> Subsequently, Al was deposited on the electron injection layer by a vacuum vapor deposition method, whereby a cathode having an average thickness of 100 nm constituted by Al was formed.

<8> Subsequently, a protective cover (sealing member) made of glass was placed thereon so as to cover the respective formed layers, and fixed and sealed with an epoxy resin.

By the above-mentioned steps, a light-emitting element of Example 1 was produced.

Examples 2 to 5

Light-emitting elements of Examples 2 to 5 were produced in the same manner as in the above-mentioned Example 1 except that the average thickness of the first electron transport layer to be formed in the step <5> was changed as shown in Table 1.

Example 6

A light-emitting element of Example 6 was produced in the same manner as in the above-mentioned Example 1 except that the formation of the first electron transport layer was performed by the following step <2'> in place of the step <2>.

<2'> A compound (amine-based compound) represented by the above formula HIL-1 and a compound (anthracene-based compound) represented by the above ETL2-30 were co-deposited at a molar ratio of 1:1 on the ITO electrode by a vacuum vapor deposition method, whereby a hole injection layer having an average thickness of 30 nm was formed.

Comparative Example 1

A light-emitting element of Comparative Example 1 was produced in the same manner as in the above-mentioned Example 1 except that the formation of the second electron transport layer in the step <4> was omitted, and further, the average thickness of the first electron transport layer to be formed in the step <5> was changed to 60 nm.

Comparative Examples 2 to 5

Light-emitting elements of Comparative Examples 2 to 5 were produced in the same manner as in the above-mentioned Example 1 except that the average thickness of the first electron transport layer to be formed in the step <5> was changed as shown in Table 1.

3. Evaluation

With respect to each of the light-emitting elements of the respective Examples and Comparative Examples, a constant current of 100 mA/cm$^2$ was allowed to flow through each of the light-emitting elements using a constant current power supply (KEITHLEY 2400 manufactured by TOYO Corporation), and the emission intensity in a wavelength range of 650 nm to 1000 nm at that time was measured using a compact fiber optical spectrometer (S2000, manufactured by Ocean Optics, Inc.). Based on the measurement results, the external quantum efficiency (EQE (%)) in a wavelength range of 650 nm to 1000 nm was measured.

Further, a constant current of 600 mA/cm$^2$ was allowed to flow through each of the light-emitting elements, and a time until the luminance decreased to 80% of the initial luminance (LT80) was measured.

These measurement results are shown in Table 1.

TABLE 1

| | Constituent material of hole injection layer | Film thickness of electron transport layer (nm) | | Emission characteristics | | Life characteristics | |
|---|---|---|---|---|---|---|---|
| | | ETL2 | ETL1 | Current density (mA/cm$^2$) | EQE (%) | Current density (mA/cm$^2$) | LT80 (hr) |
| Example 1 | HIL-1 | 55 | 5 | 100 | 3.6 | 600 | 1300 |
| Example 2 | HIL-1 | 55 | 4 | 100 | 3.5 | 600 | 1600 |
| Example 3 | HIL-1 | 55 | 3 | 100 | 3.4 | 600 | 2000 |
| Example 4 | HIL-1 | 55 | 2 | 100 | 3.2 | 600 | 1000 |
| Example 5 | HIL-1 | 55 | 6 | 100 | 3.4 | 600 | 1100 |
| Example 6 | HIL-1 + ETL2-30 | 55 | 5 | 100 | 3.6 | 600 | 1500 |
| Comparative Example 1 | HIL-1 | — | 60 | 100 | 2.9 | 600 | 50 |
| Comparative Example 2 | HIL-1 | 55 | 15 | 100 | 3.5 | 600 | 40 |
| Comparative Example 3 | HIL-1 | 55 | 10 | 100 | 3.3 | 600 | 220 |
| Comparative Example 4 | HIL-1 | 55 | 9 | 100 | 3.3 | 600 | 350 |
| Comparative Example 5 | HIL-1 | 55 | 8 | 100 | 3.3 | 600 | 550 |

As apparent from Table 1, it was found that each of the light-emitting elements of the respective Examples emits light in a near-infrared range, and also the life thereof is extended as compared with the light-emitting elements of Comparative Examples.

Further, as shown in the light-emitting elements of Examples 2, 3, and 6, it was found that by setting the average thickness of the first electron transport layer to 3 to 4 nm, or by constituting the hole injection layer by a mixture of an amine-based compound (triarylamine-based compound) and an anthracene-based compound, the life of the light-emitting element is further extended.

Further, when comparing the light-emitting elements of the respective Examples (in particular, Examples 1 and 6) with the light-emitting element of Comparative Example 1, the light-emitting elements of the respective Examples (in particular, Examples 1 and 6) have a higher external quantum efficiency than the light-emitting element of Comparative Example 1, and the concentration quenching property can be reduced.

The invention claimed is:

1. A light-emitting element, comprising:
an anode;
a cathode;
a light-emitting layer which is provided between the anode and the cathode and emits light in a wavelength range of 700 nm or more by applying a current between the anode and the cathode;
an electron transport layer which is provided between the light-emitting layer and the cathode, and includes a first electron transport layer located on the cathode side and a second electron transport layer located on the light-emitting layer side; and
a hole injection layer provided between the light-emitting layer and the anode,
wherein the first electron transport layer contains a first anthracene-based compound, which has an anthracene skeleton and a nitrogen-containing heterocyclic skeleton, and has an average thickness of less than 8 nm,
the second electron transport layer contains a second anthracene-based compound, which has an anthracene skeleton but does not have a heterocyclic skeleton, and
the hole injection layer is constituted by including a material having a hole injection property and at least one of the first anthracene-based compound and the second anthracene-based compound.

2. The light-emitting element according to claim 1, wherein the electron mobility of the second anthracene-based compound is larger than the electron mobility of the first anthracene-based compound.

3. The light-emitting element according to claim 1, wherein the average thickness of the second electron transport layer is 25 nm or more and 200 nm or less.

4. The light-emitting element according to claim 1, wherein
the light-emitting layer is constituted by including a light-emitting material and a host material which holds the light-emitting material, and the light-emitting material, the host material, the first anthracene-based compound, and the second anthracene-based compound each have a glass transition temperature of 125° C. or higher.

5. The light-emitting element according to claim 1, wherein the light-emitting element is used by applying a current between the anode and the cathode at a current density of 500 A/cm$^2$ or more and 1000 A/cm$^2$ or less.

6. A light-emitting device, comprising the light-emitting element according to claim 1.

7. An authentication device, comprising the light-emitting element according to claim 1.

8. An electronic apparatus, comprising the light-emitting element according to claim 1.

* * * * *

UNITED STATES PATENT AND TRADEMARK OFFICE
CERTIFICATE OF CORRECTION

PATENT NO. : 10,431,761 B2
APPLICATION NO. : 15/322999
DATED : October 1, 2019
INVENTOR(S) : Yuiga Hamade et al.

Page 1 of 1

It is certified that error appears in the above-identified patent and that said Letters Patent is hereby corrected as shown below:

In the Specification

Column 2, Lines 62-63, "500 A/cm² or more and 1000 A/cm² or less" should read --500 mA/cm² or more and 1000 mA/cm² or less--.
Column 3, Lines 19-20, "500 A/cm² or more and 1000 A/cm² or less" should read --500 mA/cm² or more and 1000 mA/cm² or less--.
Column 17, Lines 48-49, "500 A/cm² or more and 1000 A/cm² or less" should read --500 mA/cm² or more and 1000 mA/cm² or less--.
Column 46, Line 11, "500 A/cm² or more and 1000 A/cm² or less" should read --500 mA/cm² or more and 1000 mA/cm² or less--.
Column 46, Lines 63-64, "500 A/cm² or more and 1000 A/cm² or less" should read --500 mA/cm² or more and 1000 mA/cm² or less--.
Column 91, Lines 33-34, "500 A/cm² or more and 1000 A/cm² or less" should read --500 mA/cm² or more and 1000 mA/cm² or less--.
Column 95, Line 6, "500 A/cm² or more and 1000 A/cm² or less" should read --500 mA/cm² or more and 1000 mA/cm² or less--.

In the Claims

Column 103, Line 8, "500 A/cm² or more and 1000 A/cm² or less" should read --500 mA/cm² or more and 1000 mA/cm² or less--.

Signed and Sealed this
Eighth Day of June, 2021

Drew Hirshfeld
*Performing the Functions and Duties of the
Under Secretary of Commerce for Intellectual Property and
Director of the United States Patent and Trademark Office*